US009451775B2

(12) United States Patent
Bretschneider et al.

(10) Patent No.: US 9,451,775 B2
(45) Date of Patent: Sep. 27, 2016

(54) HETEROCYCLIC COMPOUNDS AS PESTICIDES

(71) Applicant: Bayer Intellectual Property GmbH

(72) Inventors: Thomas Bretschneider, Lohmar (DE);
Eva-Maria Franken, Lyons (FR);
Ulrich Görgens, Ratingen (DE);
Martin Füsslein, Düsseldorf (DE);
Achim Hense, Leverkusen (DE);
Joachim Kluth, Langenfeld (DE);
Hans-Georg Schwarz, Dorsten (DE);
Adeline Köhler, Wuppertal (DE); Olga Malsam, Rösrath (DE); Arnd Voerste, Köln (DE); Angela Becker, Düsseldorf (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/327,144

(22) Filed: Jul. 9, 2014

(65) Prior Publication Data

US 2014/0336186 A1 Nov. 13, 2014

Related U.S. Application Data

(62) Division of application No. 13/054,401, filed as application No. PCT/EP2009/004832 on Jul. 4, 2009, now Pat. No. 8,809,547.

(30) Foreign Application Priority Data

Jul. 17, 2008 (EP) .................................... 08012898

(51) Int. Cl.

| | | |
|---|---|---|
| C07D 417/14 | (2006.01) |
| A01N 43/82 | (2006.01) |
| A01N 43/78 | (2006.01) |
| A01N 43/56 | (2006.01) |
| A01N 43/88 | (2006.01) |
| A01N 47/38 | (2006.01) |
| C07D 401/14 | (2006.01) |
| C07D 413/14 | (2006.01) |
| A01N 43/84 | (2006.01) |

(52) U.S. Cl.
CPC ............ *A01N 43/78* (2013.01); *A01N 43/56* (2013.01); *A01N 43/82* (2013.01); *A01N 43/84* (2013.01); *A01N 43/88* (2013.01); *A01N 47/38* (2013.01); *C07D 401/14* (2013.01); *C07D 413/14* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 3,178,338 A | 4/1965 | Siegrist et al. |
| 3,178,440 A | 4/1965 | Siegrist et al. |
| 4,080,457 A | 3/1978 | Harrison et al. |
| 4,508,717 A | 4/1985 | Berger et al. |
| 4,853,396 A | 8/1989 | Farooq |
| 6,087,371 A * | 7/2000 | Mantegani ........... C07D 457/02 514/286 |
| 9,233,951 B2 | 1/2016 | Mühlthau et al. |
| 2008/0182837 A1 | 7/2008 | Steurer et al. |
| 2011/0098287 A1 | 4/2011 | Bretschneider et al. |
| 2011/0166143 A1 | 7/2011 | Bretschneider et al. |
| 2012/0094837 A1 | 4/2012 | Muhlthau et al. |
| 2012/0095023 A1 | 4/2012 | Bretschneider et al. |
| 2012/0165345 A1 | 6/2012 | Bretschneider et al. |

FOREIGN PATENT DOCUMENTS

| | | |
|---|---|---|
| CA | 2 290 379 A1 | 11/1998 |
| CA | 2 730 844 A1 | 1/2010 |
| CH | 409 511 A | 12/1961 |
| DE | 36 41 184 A1 | 6/1987 |
| DE | 197 21 031 A1 | 11/1998 |
| EP | 0 288 432 A1 | 10/1988 |
| GB | 1 101 333 A | 1/1968 |
| WO | WO 96/32938 A1 | 10/1996 |
| WO | WO 97/30050 A1 | 8/1997 |
| WO | WO98/56785 A1 | 12/1998 |
| WO | WO 03/015776 A1 | 2/2003 |
| WO | WO 2004/050024 A2 | 6/2004 |
| WO | WO 2005/005435 A1 | 1/2005 |
| WO | WO 2005/118535 A1 | 12/2005 |
| WO | WO 2006/066172 A1 | 6/2006 |
| WO | WO 2006/135627 | 12/2006 |
| WO | WO 2007/061923 A2 | 5/2007 |
| WO | WO 2008/003770 A1 | 1/2008 |

(Continued)

OTHER PUBLICATIONS

Ahmad, A., et al., "Polyaza Heterocycles. Part 2.[1] Nucleophilic Substitution of Halogens in Halogenoquinoxalino[2,3-c]cinnolines," *Journal of the Chemical Society, Perkin Transactions I* 1994:2751-2758, Chemical Society, England (1994).

Antilla, J.C., et al., "Copper-Diamine-Catalyzed N-Arylation of Pyrroles, Pyrazoles, Indazoles, Imidazoles, and Triazoles," *Journal of Organic Chemistry* 69:5578-5587, American Chemical Society, United States (2004).

Bradley, P., et al., "Preliminary communication: The synthesis of new mesogenic 1,3,4-thiadiazole-2-carboxylase esters via a novel ring-closure," *Liquid Crystal Today* 14:15-18, Taylor & Francis Group Ltd., United Kingdom (2005).

Cai, D., et al., "A Study of the Lithiation of 2,6-Dibromopyridine with Butyllithium, and its Application to Synthesis of L-739,010," *Tetrahedron Letters* 37:2537-2540, Elsevier Science Ltd., Great Britain (1996).

(Continued)

*Primary Examiner* — Emily Bernhardt
(74) *Attorney, Agent, or Firm* — Sterne, Kessler, Goldstein, Fox P.L.L.C.

(57) ABSTRACT

The present application relates to the use of heterocyclic compounds, some of which are known, for controlling animal pests, including arthropods and in particular insects, furthermore to novel heterocyclic compounds and to processes for their preparation.

6 Claims, No Drawings

(56) References Cited

FOREIGN PATENT DOCUMENTS

| WO | WO 2008/049864 A1 | 5/2008 |
|----|-------------------|--------|
| WO | WO 2008/103351 A2 | 8/2008 |
| WO | WO 2009/003998 A2 | 1/2009 |

OTHER PUBLICATIONS

Hearn, M.J., et al,, "A Convenient Method for the Preparation of Tuberculostatic Diacylhydrazines," *Bulletin des Sociétés Chimiques Belges* 106:109-114, Comité van Beheer van het Bulletin v.z.w., Belgium (1997).
Kahnt, F.W. and Neher, R., "Modifikationen der Nebennierenrindenfunktion in vitro durch 3- und 4-Pyridinderivate," *Experientia* 27:959-961, Birkhäuser Verlag, Switzerland (1971).
Kaneko, K., et al., "Preparation of 2-Aryl-4a,5-Dihydro-4H[1,3,4]Oxadiazino[4,5-a]Indoles As a [a] -Fused Indole Derivatives," *Heterocycles* 37:1645-1656, Elsevier, Netherlands (1994).
Kerr, V.N., et al., "Liquid Scintillators. VII. 2,5-Diaryl Substituted Thiazoles as Liquid Scintillator Solutes," *Journal of Organic Chemistry* 24:1861-1864, American Chemical Society, United States (1959).
Mane, A.S., et al., "Synthesis of New Organophosphorous Compounds: Their Pesticidal and Nematicidal Activity," *Oriental Journal of Chemistry* 16:475-478, Oriental Scientific Publishing Co., India (2000).
Fernández-Megia, E., et al., "Enantiomerically Pure Highly Functionalized α-Amino Ketones from the Reaction of Chiral Cyclic N-(9-Phenylfluoren-9-yl) α-Amido Esters with Organolithium Reagents," *Journal of Organic Chemistry* 62:4770-4779, American Chemical Society, United States (1997).
Moyroud, J., et al., "Synthesis of Pyrazolo[1,5-b][1,2]Benzisothiazoles," *Heterocycles* 43:221-228, Elsevier, Netherlands (1996).
Nishikawa, Y., et al., "Acrylamide Derivatives as Antiallergic Agents. 2.[1] Synthesis and Structure-Activity Relationships of N-[4-[4-(Diphenylmethyl)-1-piperazinyl]butyl]-3-(3-pyridyl)acrylamides," *Journal of Medicinal Chemistry* 32:583-593, American Chemical Society, United States (1989).
Nuriev, V.N., et al., "Synthetic pathways to a family of pyridine-containing azoles—promising ligands for coordination chemistry," *ARKIVOC* 2005(iv):208-224, ARKAT USA, Inc., United States (2005).
Price, C.C. and Schlling, G.H., "6-Chloro-2-naphthylmethylcarbinol, 6-Chloro-2-vinyl-naphthalene and Related Compounds," *Journal of the American Chemical Society* 70:4265-4266, American Chemical Society, United States (1948).
Rao, V.R. and Srinivasan, V.R., "1,3,4-Oxa(thia)diazoles: Part V—2-Amino-5-aryl-1,3,4-thiadiazoles," *Indian Journal of Chemistry* 8:509-513, Council of Scientific & Industrial Research, India (1970).
Seijas, J.A., et al., "Straightforward microwave-assisted synthesis of 2-thiazolines using Lawesson's reagent under solvent-free conditions," *Tetrahedron* 64:9280-9285, Elsevier Ltd., England (2008).
Tseng, S.-S., et al., "A Simple Regioselective Synthesis of Pyrimido[1,2- a]benzimidazoles," *Journal of Heterocyclic Chemistry* 24:837-843, Journal of Heterocyclic Chemistry, United States (1987).
Wang, F. and Schwabacher, A.W., "A Convenient Set of Bidentate Pyridine Ligands for Combinatorial Synthesis," *Tetrahedron Letters* 40:4779-4782, Elsevier Science Ltd., England (1999).
Zelenin, K.N., et al., "Synthesis of Pyrazole, 1,3,4-Thiadiazole, and 1,2,4-Triazole Derivatives by Condensatoin of 1,3-Dioxo Compounds With Thiosemicarbazide Derivatives," *Chemistry of Heterocyclic Compounds* 26:1051-1060, Plenum Publishing Corporation, United States (1990).
Database CAPLUS on STN, Accession No. 1971:505619, English language abstract for Kahnt, F.W. and Neher, R., "Modifikationen der Nebennierenrindenfunktion in vitro durch 3- und 4-Pyridinderivate," *Experientia* 27:959-961, Birkhäuser Verlag, Switzerland (1971).

English language Abstract of German Patent Publication No. DE 36 41 184 A1, European Patent Office, Espacenet database—Worldwide (1986).
English language Abstract of WIPO Patent Publication No. WO 98/56785 A1, European Patent Office, Espacenet database—Worldwide (1998).
English language translation of the International Search Report for International Application No. PCT/EP2009/004832, European Patent Office, Rijswijk, Netherlands, mailed on Feb. 22, 2011.
English language translation of the International Preliminary Report on Patentability for International Application No. PCT/EP2009/004832, International Bureau of WIPO, Geneva, Switzerland, issued May 3, 2011.
English language translation of the Written Opinion of the International Searching Authority for International Application No. PCT/EP2009/004832, European Patent Office, Munich, Germany, mailed on May 3, 2011.
von Erlenmeyer, H., et al., "Über Derivate von Thiazolearbonsäuren," *Helvetica Chimica Acta.* 27:1432-1436, Verlag Helvetica Chimica Acta, Switzerland (1944).
von Karrer, P. and Schukri, J., "Über einige Verbindungen mit verketteten Thiazol-, Penyl- und Pyridinringen," *Helvetica Chimica Acta.* 28:820-824, Verlag Helvetica Chimica Acta, Switzerland (1945).
von Menassé, R., et al., "Über einige Dipyridyl- und Terpyridyl-Analoge," *Helvetica Chimica Acta.* 40:554-560, Verlag Helvetica Chimica Acta, Switzerland (1957).
Wislicenus, W., "Über Ester-Kondensationen mit Chlor-essigester," *Chemische Berichte* 43:3528-3533, VCH Verlagsgesellschaft mbH, Germany (1910).
Office Action mailed Dec. 24, 2013, in U.S. Appl. No. 13/183,709, inventors Mühlthau et al., filed Jul. 15, 2011.
Office Action mailed May 23, 2014, in U.S. Appl. No. 12/997,803, inventors Bretschneider et al., filed Dec. 13, 2010.
Office Action mailed Jun. 17, 2014, in U.S. Appl. No. 13/183,709, inventors Mühlthau et al., filed Jul. 15, 2011.
Office Action mailed Sep. 24, 2013, in U.S. Appl. No. 12/997,803, inventors Bretschneider et al., filed Dec. 13, 2010.
Advisory Action mailed Jul. 18, 2013, in U.S. Appl. No. 12/997,803, inventors Bretschneider et al., filed Dec. 13, 2010.
Office Action mailed Apr. 11, 2013, in U.S. Appl. No. 12/997,803, inventors Bretschneider et al., filed Dec. 13, 2010.
Office Action mailed Aug. 9, 2012, in U.S. Appl. No. 12/997,803, inventors Bretschneider et al., filed Dec. 13, 2010.
Office Action mailed Sep. 18, 2013, in U.S. Appl. No. 13/183,709, inventors Mühlthau et al., filed Jul. 15, 2011.
Office Action mailed May 22, 2013, in U.S. Appl. No. 13/183,709, inventors Mühlthau et al., filed Jul. 15, 2011.
Office Action mailed Apr. 22, 2013, in U.S. Appl. No. 13/088,026, inventors Bretschneider et al., filed Apr. 15, 2011.
Notice of Allowance mailed Oct. 16, 2013, in U.S. Appl. No. 13/088,026, inventors Bretschneider et al., filed Apr. 15, 2011.
Notice of Allowance mailed Nov. 6, 2013, in U.S. Appl. No. 13/171,030, inventors Bretschneider et al., filed Jun. 28, 2011.
Office Action mailed Jun. 10, 2013, in U.S. Appl. No. 13/171,030, inventors Bretschneider et al., filed Jun. 28, 2011.
Aggarwal, V.K., et al., "A Novel One-Pot Method for the Preparation of Pyrazoles by 1,3-Dipolar Cycloadditions of Diazo Compounds Generated in Situ," *J Org Chem* 68(13):5381-5383, American Chemical Society, United States (2003).
Bilodeau, M.T., et al., "Allosteric inhibitors of Aktl and Akt2: a naphthyridinone with efficacy in an A2780 tumor xenograft model," *Bioorg Med Chem Lett* 18(11):3178-3182, Elsevier Ltd., England (2008).
Ferles, M., et al., "Synthesis and Reactions of novel 1,3-dipyridinyl-1,3- propanediones," *Collect Czech Chem Commun* 55:1228-1233, Nakladatelstvi Ceskoslovenski Akademie Ved, Czech Republic (1990).
Office Action mailed Oct. 3, 2012, in U.S. Appl. No. 13/183,709, inventors Muhlthau et al., filed Jul. 15, 2011.

(56) References Cited

OTHER PUBLICATIONS

Brunner, H. and Scheck, T., "Neue optisch aktive Pyrazolderivate für die enantioselektive Katalysc," *Chem. Ber.* 125:701-709, VCH Verlagsgesellschaft mbH, Germany (1992).

Notice of Allowance mailed Oct. 1, 2015, in U.S. Appl. No. 13/183,709, Mühlthau, F.A., et al., filed Jul. 15, 2011.

Office Action mailed Jul. 9, 2015 in U.S. Appl. No. 12/997,803, Bretschneider, T., et al., filed Dec. 13, 2010.

Office Action mailed Jul. 29, 2015 in U.S. Appl. No. 14/156,897, Bretschneider, T., et al., filed Jan. 16, 2014.

Office Action mailed Jan. 11, 2016 in U.S. Appl. No. 12/997,803, Bretschneider, T., et al., filed Dec. 13, 2010.

Notice of Allowance mailed Jun. 16, 2015, in U.S. Appl. No. 13/183,709, Mühlthau, F.A., et al., filed Jul. 15, 2011.

Notice of Allowance mailed Feb. 23, 2016, in U.S. Appl. No. 14/156,897, Bretschneider, T., et al., filed Jan. 16, 2014.

Office Action mailed Feb. 18, 2015, in U.S. Appl. No. 13/183,709, Mühlthau, F.A., et al., filed Jul. 15, 2011.

Office Action mailed Dec. 30, 2014, in U.S. Appl. No. 12/997,803, Bretschneider, T., et al., filed Dec. 13, 2010.

\* cited by examiner

HETEROCYCLIC COMPOUNDS AS PESTICIDES

This application is a divisional of U.S. application Ser. No. 13/054,401, 371(c) date of May 17, 2011, which is a National Stage of international application number PCT/EP2009/004832, filed on Jul. 4, 2009, which claims priority to EP Application No. 08012898.6, filed Jul. 17, 2008. The disclosures of which are incorporated by reference in their entirety.

The present application relates to the use of heterocyclic compounds, some of which are known, for controlling animal pests including arthropods and in particular insects, furthermore to novel heterocyclic compounds and to processes for their preparation.

Certain thiazolyl compounds are already known; however, a use for controlling animal pests has hitherto not been described (cf. WO 2003/015776).

Also known are thiadiazole compounds. CH 411 906 and EP 0 288 432 A1 describe the use of such compounds as optical brighteners. CH 409 511 discloses thiadiazoles suitable for controlling nematodes. DE 3641184 describes certain phenyl-substituted thiadiazoles for controlling pests.

WO 1998/056785 and WO 1996/032938 disclose pyrazole compounds, for which pharmaceutical applications are stated.

Modern crop protection agents have to satisfy many demands, for example with respect to efficacy, persistence and spectrum of their action and possible use. Questions of toxicity, the combinability with other active compounds or formulation auxiliaries play a role, as well as the question of the expense that the synthesis of an active compound requires. Furthermore, resistances may occur. For all these reasons, the search for novel crop protection agents cannot be considered as having been concluded, and there is a constant need for novel compounds having properties which, compared to the known compounds, are improved at least in respect of individual aspects.

It was an object of the present invention to provide compounds which widen the spectrum of the pesticides under various aspects.

This object and further objects not explicitly mentioned which can be derived or deduced from the context discussed here are, in part, achieved by novel compounds of the formula (I),

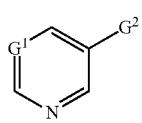
(I)

in which
(Ia)
$G^1$ represents N, CH or C-halogen,
$G^2$ represents

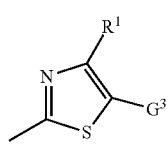
(A)

in which
$R^1$ represents hydrogen or alkyl and
$G^3$ represents optionally substituted heterocyclyl, represents optionally substituted heteroaryl or represents optionally substituted aryl or
(Ib)
$G^1$ represents N or C-halogen,
$G^2$ represents

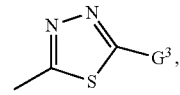
(B)

in which
$G^3$ represents optionally substituted heterocyclyl, represents optionally substituted heteroaryl or represents optionally substituted aryl or
(Ic)
$G^1$ represents CH,
$G^2$ represents

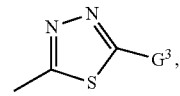
(B)

in which
$G^3$ represents optionally substituted heterocyclyl or represents substituted furanyl or represents thienyl which is substituted by halogen, nitro, amino, alkylamino, dialkylamino, haloalkyl, cycloalkylalkyl, alkoxy, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, C(X)NR²R³, (in which X represents oxygen or sulphur, R² represents hydrogen or alkyl and R³ represents alkyl, haloalkyl, alkoxy, cyanoalkyl, alkynyl, cycloalkyl, cycloalkylalkyl, alkoxyalkyl, alkylthioalkyl or arylalkyl or R² and R³ together with the nitrogen atom to which they are attached form a ring), alkylsulphinyl, alkylsulphonyl, heterocyclyl, aryl (which for its part may be substituted by halogen, cyano, nitro, alkyl or haloalkyl), heteroaryl (which for its part may be substituted by halogen, nitro, alkyl, haloalkyl, alkoxy, haloalkoxy, alkoxyalkyl, alkylthio, alkylthioalkyl or cycloalkyl), heteroarylalkyl (which for its part may be substituted by halogen, nitro, alkyl, haloalkyl, alkoxy, haloalkoxy, alkoxyalkyl, alkylthio, alkylthioalkyl or cycloalkyl) or represents in each case optionally substituted hetaryl from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl or represents cyano-, nitro-, haloalkoxy- or heterocyclyl-substituted aryl or (Id)
G¹ represents N, CH or C-halogen,
G² represents

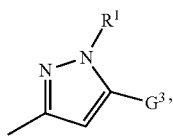

(C)

in which
R¹ represents hydrogen or alkyl and
G³ represents optionally substituted heterocyclyl or represents optionally substituted heteroaryl or represents optionally substituted aryl,
and also salts, metal complexes and N-oxides of the compounds of the formula (I), which can be used for controlling pests.

It has been found that the compounds of the formula (I) have pronounced biological properties and are suitable especially for controlling animal pests, in particular insects, arachnids and nematodes, encountered in agriculture, in forests, in the protection of stored products and materials and in the hygiene sector.

The known compounds of the formula (I) can be obtained by the preparation processes described in the publications mentioned above.

Preferred substituents or ranges of the radicals cited in the compounds (Ia), (Ib), (Ic) and (Id) mentioned above are illustrated below.

Preference is given to using compounds of the formula (I),

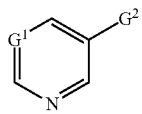

(I)

in which
(Ia)
G¹ represents N, CH or C-halogen,
G² represents

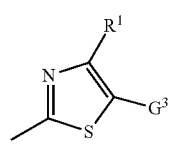

(A)

in which
R¹ represents hydrogen or alkyl and
G³ represents in each case optionally halogen-, cyano-, nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, alkylcycloalkyl-, alkylcarbonyl-, alkoxycarbonyl-, aminocarbonyl-, pyridyl- or pyrimidyl-substituted oxazolinyl, dihydrooxadiazinyl, dihydrodioxazinyl or hydroxypyridyl, represents hetaryl from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, in particular pyridyl, pyrimidyl, imidazolyl, pyrazolyl, triazinyl, thiazolyl, thiadiazolyl, oxadiazolyl and oxazolyl, optionally substituted by halogen, nitro, amino, alkylamino, dialkylamino, alkyl, haloalkyl, cycloalkylalkyl, alkoxy, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, C(X)NR²R³, (in which X represents oxygen or sulphur, R² represents hydrogen or alkyl and R³ represents alkyl, haloalkyl, alkoxy, cyanoalkyl, alkynyl, cycloalkyl, cycloalkylalkyl, alkoxyalkyl, alkylthioalkyl or arylalkyl or R² and R³ together with the nitrogen atom to which they are attached form a ring), alkylthio, alkylsulphinyl, alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by alkyl or haloalkyl), phenyl (which for its part may be substituted by halogen, cyano, nitro, alkyl or haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkanediyl, alkoxy, haloalkoxy, alkoxyalkyl, alkylthio, alkylthioalkyl and cycloalkyl), the heteroarylalkyl radicals triazolylalkyl, pyridylalkyl, pyrimidylalkyl or oxadiazolylalkyl (which for their part may be substituted by alkyl) or represents optionally halogen-, cyano-, alkyl-, haloalkyl-, alkoxy-, haloalkoxy-, piperidinonyl-, pyrrolidinonyl-, dioxolanyl- or dihydrodioxazinyl-substituted phenyl or (Ib)
G¹ represents N or C-halogen,
G² represents

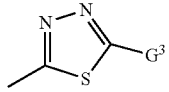

(B)

in which
G³ represents in each case optionally halogen-, cyano-, nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, alkylcycloalkyl-, alkylcarbonyl-, alkoxycarbonyl-, aminocarbonyl-, pyridyl- or pyrimidyl-substituted oxazolinyl, dihydrooxadiazinyl, dihydrodioxazinyl or hydroxypyridyl, represents hetaryl from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, in particular pyridyl, pyrimidyl, imidazolyl, pyrazolyl, triazinyl, thiazolyl, thiadiazolyl, oxadiazolyl and oxazolyl, optionally substituted by halogen, nitro, amino, alkylamino, dialkylamino, alkyl, haloalkyl, cycloalkylalkyl, alkoxy, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, C(X)NR$^2$R$^3$, (in which X represents oxygen or sulphur, R$^2$ represents hydrogen or alkyl and R$^3$ represents alkyl, haloalkyl, alkoxy, cyanoalkyl, alkynyl, cycloalkyl, cycloalkylalkyl, alkoxyalkyl, alkylthioalkyl or arylalkyl or R$^2$ and R$^3$ together with the nitrogen atom to which they are attached form a ring), alkylthio, alkylsulphinyl, alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by alkyl or haloalkyl), phenyl (which for its part may be substituted by halogen, cyano, nitro, alkyl or haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl), the heteroarylalkyl radicals triazolylalkyl, pyridylalkyl, pyrimidylalkyl or oxadiazolylalkyl (which for their part may be substituted by alkyl) or represents optionally halogen-, cyano-, alkyl-, haloalkyl-, alkoxy-, haloalkoxy-, piperidinonyl-, pyrrolidinonyl-, dioxolanyl- or dihydrodioxazinyl-substituted phenyl or (Ic)
G$^1$ represents CH,
G$^2$ represents

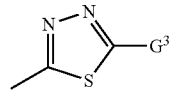

(B)

in which
G$^3$ represents in each case optionally halogen-, cyano-, nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, alkylcycloalkyl-, alkylcarbonyl-, alkoxycarbonyl-, aminocarbonyl-, pyridyl- or pyrimidyl-substituted oxazolinyl, dihydrooxadiazinyl, dihydrodioxazinyl or hydroxypyridyl or represents furanyl which is substituted by halogen, nitro, amino, alkylamino, dialkylamino, alkyl, haloalkyl, cycloalkylalkyl, alkoxy, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, C(X)NR$^2$R$^3$, (in which X represents oxygen or sulphur, R$^2$ represents hydrogen or alkyl and R$^3$ represents alkyl, haloalkyl, alkoxy, cyanoalkyl, alkynyl, cycloalkyl, cycloalkylalkyl, alkoxyalkyl, alkylthioalkyl or arylalkyl or R$^2$ and R$^3$ together with the nitrogen atom to which they are attached form a ring), alkylsulphinyl, alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by alkyl or haloalkyl), phenyl (which for its part may be substituted by halogen, cyano, litro, alkyl or haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl), the heteroarylalkyl radicals triazolylalkyl, pyridylalkyl, pyrimidylalkyl or oxadiazolylalkyl (which for their part may be substituted by alkyl) or represents thienyl which is substituted by halogen, nitro, amino, alkylamino, dialkylamino, haloalkyl, cycloalkylalkyl, alkoxy, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, C(X)NR$^2$R$^3$, (in which X represents oxygen or sulphur, R$^2$ represents hydrogen or alkyl and R$^3$ represents alkyl, haloalkyl, alkoxy, cyanoalkyl, alkynyl, cycloalkyl, cycloalkylalkyl, alkoxyalkyl, alkylthioalkyl or arylalkyl or R$^2$ and R$^3$ together with the nitrogen atom to which they are attached form a ring), alkylsulphinyl, alkylsulphonyl, the heterocyclyl radicals morpholinyl, triazolinonyl, piperidinonyl, pyrrolidinonyl and pyrazolinonyl (which for their part may be substituted by alkyl or haloalkyl), phenyl (which for its part may be substituted by halogen, cyano, nitro, alkyl or haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl), the heteroarylalkyl radicals triazolylalkyl, pyridylalkyl, pyrimidylalkyl or oxadiazolylalkyl (which for their part may be substituted by alkyl) or represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl, each of which is optionally substituted by halogen, nitro, amino, alkylamino, dialkylamino, alkyl, haloalkyl, cycloalkylalkyl, alkoxy, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, C(X)NR²R³, (in which X represents oxygen or sulphur, R² represents hydrogen or alkyl and R³ represents alkyl, haloalkyl, alkoxy, cyanoalkyl, alkynyl, cycloalkyl, cycloalkylalkyl, alkoxyalkyl, alkylthioalkyl or arylalkyl or R² and R³ together with the nitrogen atom to which they are attached form a ring), alkylsulphinyl, alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by alkyl or haloalkyl), phenyl (which for its part may be substituted by halogen, cyano, nitro, alkyl or haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl), the heteroarylalkyl radicals triazolylalkyl, pyridylalkyl, pyrimidylalkyl or oxadiazolylalkyl (which for their part may be substituted by alkyl) or represents cyano-, nitro-, haloalkoxy-, dioxolanyl- or dihydrodioxazinyl-substituted phenyl or (Id)

G¹ represents N, CH or C-halogen,

G² represents

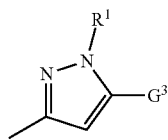
(C)

in which

R¹ represents hydrogen or alkyl and

G³ represents in each case optionally halogen-, cyano-, nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, alkylcycloalkyl-, alkylcarbonyl-, alkoxycarbonyl-, aminocarbonyl-, pyridyl- or pyrimidyl-substituted oxazolinyl, dihydrooxadiazinyl, dihydrodioxazinyl or hydroxypyridyl, represents hetaryl from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, in particular pyridyl, pyrimidyl, imidazolyl, pyrazolyl, triazinyl, thiazolyl, thiadiazolyl, oxadiazolyl and oxazolyl, optionally substituted by halogen, nitro, amino, alkylamino, dialkylamino, alkyl, haloalkyl, cycloalkylalkyl, alkoxy, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, C(X)NR²R³, (in which X represents oxygen or sulphur, R² represents hydrogen or alkyl and R³ represents alkyl, haloalkyl, alkoxy, cyanoalkyl, alkynyl, cycloalkyl, cycloalkylalkyl, alkoxyalkyl, alkylthioalkyl or arylalkyl or R² and R³ together with the nitrogen atom to which they are attached form a ring), alkylthio, alkylsulphinyl, alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by alkyl or haloalkyl), phenyl (which for its part may be substituted by halogen, cyano, nitro, alkyl or haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl), the heteroarylalkyl radicals triazolylalkyl, pyridylalkyl, pyrimidylalkyl or oxadiazolylalkyl (which for their part may be substituted by alkyl) or represents optionally halogen-, cyano-, alkyl-, haloalkyl-, alkoxy-, haloalkoxy-, piperidinonyl-, pyrrolidinonyl-, dioxolanyl- or dihydrodioxazinyl-substituted phenyl and also salts and N-oxides of the compounds of the formula (I).

Particular preference is given to using compounds of the formula (I),

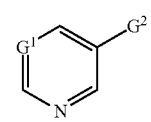
(I)

in which (Ia)

G¹ represents N, CH or C-halogen,

G² represents

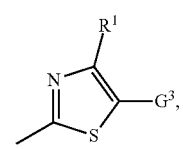
(A)

in which

R¹ represents hydrogen or $C_1$-$C_6$-alkyl and

G³ represents in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl-$C_3$-$C_6$-cycloalkyl-, $C_1$-$C_6$-alkylcarbonyl-, $C_1$-$C_6$-alkoxycarbonyl-, aminocarbonyl-, pyridyl- or pyrimidyl-substituted oxazolinyl, dihydrooxadiazinyl, dihydrodioxazinyl or hydroxypyridyl, represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, $C_1$-$C_6$-alkylamino, di($C_1$-$C_6$-alkyl)amino, $C_1$-$C_6$-alkyl, $C_1$-$C_6$-haloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkylthio, $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_1$-$C_6$-alkoxyimino-$C_1$-$C_6$-alkoxycarbonylmethyl, $C(X)NR^2R^3$, (in which X represents oxygen or sulphur, R² represents hydrogen or $C_1$-$C_6$-alkyl and R³ represents $C_1$-$C_6$-alkyl, $C_1$-$C_6$-haloalkyl, $C_1$-$C_6$-alkoxy, cyano-$C_1$-$C_6$-alkyl, $C_2$-$C_6$-alkynyl, $C_3$-$C_6$-cycloalkyl, —$C_1$-$C_6$-alkyl, $C_1$-$C_6$-alkoxy-$C_1$-$C_6$-alkyl, $C_1$-$C_6$-alkylthio-$C_1$-$C_6$-alkyl or phenyl-$C_1$-$C_6$-alkyl), $C_1$-$C_6$-alkylsulphinyl, $C_1$-$C_6$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_6$-alkyl or $C_1$-$C_6$-haloalkyl), phenyl (which for its part may be substituted by halogen, cyano, nitro, $C_1$-$C_6$-alkyl or $C_1$-$C_6$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_3$-$C_5$-alkanediyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl or $C_3$-$C_6$-cycloalkyl), the heteroarylalkyl radicals triazolyl-$C_1$-$C_6$-alkyl, pyridyl-$C_1$-$C_6$-alkyl, pyrimidyl-$C_1$-$C_6$-alkyl or oxadiazolyl-$C_1$-$C_6$-alkyl (which for their part may be substituted by $C_1$-$C_6$-alkyl) or represents optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, dioxolanyl-, piperidinonyl-, pyrrolidinonyl- or dihydrodioxazinyl-substituted phenyl or (Ib)

G¹ represents N or C-halogen,

G² represents

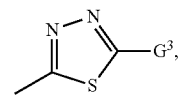

(B)

in which

G³ represents in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl-$C_3$-$C_6$-cycloalkyl-, $C_1$-$C_6$-alkylcarbonyl-, $C_1$-$C_6$-alkoxycarbonyl-, aminocarbonyl-, pyridyl- or pyrimidyl-substituted oxazolinyl, dihydrooxadiazinyl, dihydrodioxazinyl or hydroxypyridyl, represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, $C_1$-$C_6$-alkylamino, di($C_1$-$C_6$-alkyl)amino, $C_1$-$C_6$-alkyl, $C_1$-$C_6$-haloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkylthio, $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_6$-alkoxyimino-$C_1$-$C_6$-alkoxycarbonylmethyl, $C(X)NR^2R^3$, (in which X represents oxygen or sulphur, R² represents hydrogen or $C_1$-$C_6$-alkyl and R³ represents $C_1$-$C_6$-alkyl, $C_1$-$C_6$-haloalkyl, $C_1$-$C_6$-alkoxy, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkylthio-$C_1$-$C_6$-alkyl or phenyl-$C_1$-$C_6$-alkyl), $C_1$-$C_6$-alkylsulphinyl, $C_1$-$C_6$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_6$-alkyl or $C_1$-$C_6$-haloalkyl), phenyl (which for its part may be substituted by halogen, cyano, nitro, $C_1$-$C_6$-alkyl or $C_1$-$C_6$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl or $C_3$-$C_6$-cycloalkyl), the heteroarylalkyl radicals triazolyl-$C_1$-$C_6$-alkyl, pyridyl-$C_1$-$C_6$-alkyl, pyrimidyl-$C_1$-$C_6$-alkyl or oxadiazolyl-$C_1$-$C_6$-alkyl (which for their part may be substituted by $C_1$-$C_6$-alkyl) or represents optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, dioxolanyl-, piperidinonyl-, pyrrolidinonyl- or dihydrodioxazinyl-substituted phenyl or (Ic)
$G^1$ represents CH,
$G^2$ represents

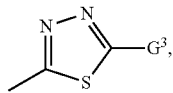
(B)

in which
$G^3$ represents in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl-$C_3$-$C_6$-cycloalkyl-, $C_1$-$C_6$-alkylcarbonyl-, $C_1$-$C_6$-alkoxycarbonyl-, aminocarbonyl-, pyridyl- or pyrimidyl-substituted oxazolinyl, dihydrooxadiazinyl, dihydrodioxazinyl or hydroxypyridyl or represents furanyl which is substituted by halogen, nitro, amino, $C_1$-$C_6$-alkylamino, di-$C_1$-$C_6$-alkylamino, $C_1$-$C_6$-alkyl, $C_1$-$C_6$-haloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkylthio, $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_1$-$C_6$-alkoxyimino-$C_1$-$C_6$-alkoxycarbonylmethyl, $C(X)NR^2R^3$, (in which X represents oxygen or sulphur, $R^2$ represents hydrogen or $C_1$-$C_6$-alkyl and $R^3$ represents $C_1$-$C_6$-alkyl, $C_1$-$C_6$-haloalkyl, $C_1$-$C_6$-alkoxy, $C_1$-$C_6$-cyanoalkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkylthio-$C_1$-$C_6$-alkyl or phenyl-$C_1$-$C_6$-alkyl), $C_1$-$C_6$-alkylsulphinyl, $C_1$-$C_6$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_6$-alkyl or $C_1$-$C_6$-haloalkyl), phenyl (which for its part may be substituted by halogen, cyano, nitro, $C_1$-$C_6$-alkyl or $C_1$-$C_6$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl and $C_3$-$C_6$-cycloalkyl), the heteroarylalkyl radicals triazolylalkyl, pyridylalkyl, pyrimidylalkyl or oxadiazolylalkyl (which for their part may be substituted by $C_1$-$C_6$-alkyl) or represents thienyl which is substituted by halogen, nitro, amino, $C_1$-$C_6$-alkylamino, di-$C_1$-$C_6$-alkylamino, $C_1$-$C_6$-haloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkylthio, $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_1$-$C_6$-alkoxyimino-$C_1$-$C_6$-alkoxycarbonylmethyl, $C(X)NR^2R^3$, (in which X represents oxygen or sulphur, $R^2$ represents hydrogen or $C_1$-$C_6$-alkyl and $R^3$ represents $C_1$-$C_6$-alkyl, $C_1$-$C_6$-haloalkyl, $C_1$-$C_6$-alkoxy, $C_1$-$C_6$-cyanoalkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkylthio-$C_1$-$C_6$-alkyl or phenyl-$C_1$-$C_6$-alkyl), $C_1$-$C_6$-alkylsulphinyl, $C_1$-$C_6$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_6$-alkyl or $C_1$-$C_6$-haloalkyl), phenyl (which for its part may be substituted by halogen, cyano, nitro, $C_1$-$C_6$-alkyl or $C_1$-$C_6$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl or $C_3$-$C_6$-cycloalkyl), the heteroarylalkyl radicals triazolylalkyl, pyridylalkyl, pyrimidylalkyl or oxadiazolylalkyl (which for their part may be substituted by $C_1$-$C_6$-alkyl) or represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, $C_1$-$C_6$-alkylamino, di($C_1$-$C_6$-alkyl)amino, $C_1$-$C_6$-alkyl, $C_1$-$C_6$-haloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkylthio, $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_6$-$C_6$-alkoxyimino-$C_1$-$C_6$-alkoxycarbonylmethyl, $C(X)NR^2R^3$, (in which X represents oxygen or sulphur, $R^2$ represents hydrogen or $C_1$-$C_6$-alkyl and $R^3$ represents $C_1$-$C_6$-alkyl, $C_1$-$C_6$-haloalkyl, $C_1$-$C_6$-alkoxy, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkylthio-$C_1$-$C_6$-alkyl or phenyl-$C_1$-$C_6$-alkyl), $C_1$-$C_6$-alkylthio, $C_1$-$C_6$-alkylsulphinyl, $C_1$-$C_6$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_6$-alkyl or $C_1$-$C_6$-haloalkyl), phenyl (which for its part may be substituted by halogen, cyano, nitro, $C_1$-$C_6$-alkyl or $C_1$-$C_6$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl or $C_3$-$C_6$-cycloalkyl), the heteroarylalkyl radicals triazolyl-$C_1$-$C_6$-alkyl, pyridyl-$C_1$-$C_6$-alkyl, pyrimidyl-$C_1$-$C_6$-alkyl or oxadiazolyl-$C_1$-$C_6$-alkyl (which for their part may be substituted by $C_1$-$C_6$-alkyl) or represents cyano-, nitro-, $C_1$-$C_6$-haloalkoxy-, dioxolanyl-, piperidinonyl-, pyrrolidinonyl- or dihydrodioxazinyl-substituted phenyl or
(Id)
$G^1$ represents N, CH or C-halogen,
$G^2$ represents

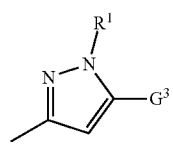

(C)

in which
$R^1$ represents hydrogen or $C_1$-$C_6$-alkyl and
$G^3$ represents in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl-$C_3$-$C_6$-cycloalkyl-, $C_1$-$C_6$-alkylcarbonyl-, $C_1$-$C_6$-alkoxycarbonyl-, aminocarbonyl-, pyridyl- or pyrimidyl-substituted oxazolinyl, dihydrooxadiazinyl, dihydrodioxazinyl or hydroxypyridyl, represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, $C_1$-$C_6$-alkylamino, di($C_1$-$C_6$-alkyl)amino, $C_1$-$C_6$-alkyl, $C_1$-$C_6$-haloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkylthio, $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_1$-$C_6$-alkoxyimino-$C_1$-$C_6$-alkoxycarbonylmethyl, $C(X)NR^2R^3$, (in which X represents oxygen or sulphur, $R^2$ represents hydrogen or $C_1$-$C_6$-alkyl and $R^3$ represents $C_1$-$C_6$-alkyl, $C_1$-$C_6$-haloalkyl, $C_1$-$C_6$-alkoxy, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkylthio-$C_1$-$C_6$-alkyl or phenyl-$C_1$-$C_6$-alkyl), $C_1$-$C_6$-alkylsulphinyl, $C_1$-$C_6$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_6$-alkyl or $C_1$-$C_6$-haloalkyl), phenyl (which for its part may be substituted by halogen, cyano, nitro, $C_1$-$C_6$-alkyl or $C_1$-$C_6$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl or $C_3$-$C_6$-cycloalkyl), the heteroarylalkyl radicals triazolyl-$C_1$-$C_6$-alkyl, pyridyl-$C_1$-$C_6$-alkyl, pyrimidyl-$C_1$-$C_6$-alkyl or oxadiazolyl-$C_1$-$C_6$-alkyl (which for their part may be substituted by $C_1$-$C_6$-alkyl) or represents optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, dioxolanyl-, piperidinonyl-, pyrrolidinonyl- or dihydrodioxazinyl-substituted phenyl and also salts and N-oxides of the compounds of the formula (I).

Very particular preference is given to using compounds of the formula (I), (I)

in which
(Ia)
$G^1$ represents N, CH or C-halogen,
$G^2$ represents (A)

in which

R$^1$ represents hydrogen or C$_1$-C$_4$-alkyl (in particular methyl) and

G$^3$ represents in each case optionally halogen-, cyano-, nitro-, C$_1$-C$_4$-alkyl-, C$_1$-C$_4$-haloalkyl-, C$_3$-C$_6$-cycloalkyl-, C$_1$-C$_4$-alkoxy-, C$_1$-C$_4$-haloalkoxy-, C$_1$-C$_4$-alkylthio-, C$_1$-C$_4$-haloalkylthio-, C$_1$-C$_4$-alkylsulphinyl-, C$_1$-C$_4$-alkylsulphonyl-, C$_1$-C$_4$-haloalkylsulphinyl-, C$_1$-C$_4$-haloalkylsulphonyl-, amino-, C$_1$-C$_4$-alkylamino-, di(C$_1$-C$_4$-alkyl)amino-, C$_1$-C$_4$-alkylcarbonylamino-, C$_1$-C$_4$-alkoxycarbonylamino-, C$_1$-C$_4$-alkoxy-C$_1$-C$_4$-alkyl-, C$_1$-C$_4$-haloalkoxy-C$_1$-C$_4$-alkyl-, C$_2$-C$_4$-alkenyl-, C$_2$-C$_4$-alkynyl-, C$_1$-C$_4$-alkyl-C$_3$-C$_6$-cycloalkyl-, C$_1$-C$_4$-alkylcarbonyl-, C$_1$-C$_4$-alkoxycarbonyl-, aminocarbonyl-, pyridyl- or pyrimidyl-substituted oxazolinyl, dihydrooxadiazinyl, dihydrodioxazinyl or hydroxypyridyl, represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, C$_1$-C$_4$-alkylamino, di(C$_1$-C$_4$-alkyl)amino, C$_1$-C$_4$-alkyl, C$_1$-C$_4$-haloalkyl, C$_3$-C$_6$-cycloalkyl-C$_1$-C$_4$-alkyl, C$_1$-C$_4$-alkoxy, C$_1$-C$_4$-haloalkoxy, C$_1$-C$_4$-alkylthio, C$_1$-C$_4$-alkoxy-C$_1$-C$_4$-alkyl, bis(C$_1$-C$_4$-alkoxy)-C$_1$-C$_4$-alkyl, C$_1$-C$_4$-alkoxycarbonyl, alpha-hydroxyimino-C$_1$-C$_4$-alkoxycarbonylmethyl, alpha-C$_1$-C$_4$-alkoxyimino-C$_1$-C$_4$-alkoxycarbonylmethyl, C(X)NR$^2$R$^3$, (in which X represents oxygen or sulphur, R$^2$ represents hydrogen or C$_1$-C$_4$-alkyl and R$^3$ represents C$_1$-C$_5$-alkyl, C$_1$-C$_4$-haloalkyl, C$_1$-C$_6$-alkoxy, cyano-C$_1$-C$_4$-alkyl, C$_2$-C$_4$-alkynyl, C$_3$-C$_6$-cycloalkyl, C$_3$-C$_6$-cycloalkyl-C$_1$-C$_4$-alkyl, C$_1$-C$_4$-alkoxy-C$_1$-C$_4$-alkyl, C$_1$-C$_4$-alkylthio-C$_1$-C$_4$-alkyl or phenyl-C$_1$-C$_4$-alkyl), C$_1$-C$_4$-alkylsulphinyl, C$_1$-C$_4$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by C$_1$-C$_4$-alkyl or C$_1$-C$_4$-haloalkyl), phenyl (which for its part may be substituted by halogen, cyano, nitro, C$_1$-C$_4$-alkyl or C$_1$-C$_4$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, C$_1$-C$_4$-alkyl, C$_1$-C$_4$-haloalkyl, C$_3$-C$_4$-alkanediyl, C$_1$-C$_4$-alkoxy, C$_1$-C$_4$-haloalkoxy, C$_1$-C$_4$-alkoxy-C$_1$-C$_4$-alkyl, C$_1$-C$_4$-alkylthio, C$_1$-C$_4$-alkylthio-C$_1$-C$_4$-alkyl or C$_3$-C$_6$-cycloalkyl), the heteroarylalkyl radicals triazolyl-C$_1$-C$_4$-alkyl, pyridyl-C$_1$-C$_4$-alkyl, pyrimidyl-C$_1$-C$_4$-alkyl or oxadiazolyl-C$_1$-C$_4$-alkyl (which for their part may be substituted by C$_1$-C$_4$-alkyl) or represents optionally halogen-, cyano-, C$_1$-C$_4$-alkyl-, C$_1$-C$_4$-haloalkyl-, C$_1$-C$_4$-alkoxy-, C$_1$-C$_4$-haloalkoxy-, dioxolanyl-, piperidinonyl-, pyrrolidinonyl- or dihydrodioxazinyl-substituted phenyl or (Ib)

G$^1$ represents N or C-halogen,

G$^2$ represents

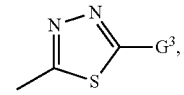

(B)

in which

G$^3$ represents in each case optionally halogen-, cyano-, nitro-, C$_1$-C$_4$-alkyl-, C$_1$-C$_4$-haloalkyl-, C$_3$-C$_6$-cycloalkyl-, C$_1$-C$_4$-alkoxy-, C$_1$-C$_4$-haloalkoxy-, C$_1$-C$_4$-alkylthio-, C$_1$-C$_4$-haloalkylthio-, C$_1$-C$_4$-alkylsulphinyl-, C$_1$-C$_4$-alkylsulphonyl-, C$_1$-C$_4$-haloalkylsulphinyl-, C$_1$-C$_4$-haloalkylsulphonyl-, amino-, C$_1$-C$_4$-alkylamino-, di(C$_1$-C$_4$-alkyl)amino-, C$_1$-C$_4$-alkylcarbonylamino-, C$_1$-C$_4$-alkoxycarbonylamino-, C$_1$-C$_4$-alkoxy-C$_1$-C$_4$-alkyl-, C$_1$-C$_4$-haloalkoxy-C$_1$-C$_4$-alkyl-, C$_2$-C$_4$-alkenyl-, C$_2$-C$_4$-alkynyl-, C$_1$-C$_4$-alkyl-C$_3$-C$_6$-cycloalkyl-, C$_1$-C$_4$-alkylcarbonyl-, C$_1$-C$_4$-alkoxycarbonyl-, aminocarbonyl-, pyridyl- or pyrimidyl-substituted oxazolinyl, dihydrooxadiazinyl, dihydrodioxazinyl or hydroxypyridyl, represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazoyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, C$_1$-C$_4$-alkylamino, di(C$_1$-C$_4$-alkyl)amino, C$_1$-C$_4$-alkyl, C$_1$-C$_4$-haloalkyl, C$_3$-C$_6$-cycloalkyl-C$_1$-C$_4$-alkyl, C$_1$-C$_4$-alkoxy, C$_1$-C$_4$-haloalkoxy, C$_1$-C$_4$-alkylthio, C$_1$-C$_4$-alkoxy-C$_1$-C$_4$-alkyl, bis(C$_1$-C$_4$-alkoxy)-C$_1$-C$_4$-alkyl, C$_1$-C$_4$-alkoxycarbonyl, alpha-hydroxyimino-C$_1$-C$_4$-alkoxycarbonylmethyl, alpha-C$_1$-C$_4$-alkoxyimino-C$_1$-C$_4$-alkoxycarbonylmethyl, C(X)NR$^2$R$^3$, (in which X represents oxygen or sulphur, R$^2$ represents hydrogen or C$_1$-C$_4$-alkyl and R$^3$ represents C$_1$-C$_4$-alkyl, C$_1$-C$_4$-haloalkyl, C$_1$-C$_6$-alkoxy, cyano-C$_1$-C$_4$-alkyl, C$_2$-C$_4$-alkynyl, C$_3$-C$_6$-cycloalkyl, C$_3$-C$_6$-cycloalkyl-C$_1$-C$_4$-alkyl, C$_1$-C$_4$-alkoxy-C$_1$-C$_4$-alkyl, C$_1$-C$_4$-alkylthio-C$_1$-C$_4$-alkyl or phenyl-C$_1$-C$_4$-alkyl), C$_1$-C$_4$-alkylsulphinyl, C$_1$-C$_4$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by C$_1$-C$_4$-alkyl or C$_1$-C$_4$-haloalkyl), phenyl (which for its part may be substituted by halogen, cyano, nitro, C$_1$-C$_4$-alkyl or C$_1$-C$_4$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl or $C_3$-$C_6$-cycloalkyl), the heteroarylalkyl radicals triazolyl-$C_1$-$C_4$-alkyl, pyridyl-$C_1$-$C_4$-alkyl, pyrimidyl-$C_1$-$C_4$-alkyl or oxadiazolyl-$C_1$-$C_4$-alkyl (which for their part may be substituted by $C_1$-$C_4$-alkyl) or represents optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, dioxolanyl-, piperidinonyl-, pyrrolidinonyl- or dihydrodioxazinyl-substituted phenyl or (Ic)
$G^1$ represents CH,
$G^2$ represents

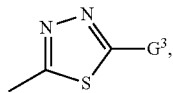
(B)

in which
$G^3$ represents in each case optionally halogen-, cyano-, nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_1$-$C_4$-alkyl-$C_3$-$C_6$-cycloalkyl-, $C_1$-$C_4$-alkylcarbonyl-, $C_1$-$C_4$-alkoxycarbonyl-, aminocarbonyl-, pyridyl- or pyrimidyl-substituted oxazolinyl, dihydrooxadiazinyl, dihydrodioxazinyl or hydroxypyridyl or represents furanyl which is substituted by halogen, nitro, amino, $C_1$-$C_4$-alkylamino, di-$C_1$-$C_4$-alkylamino, $C_1$-$C_4$-haloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkylthio, $C_1$-$C_4$-alkoxy-$C_1$-$C_4$-alkyl, bis($C_1$-$C_4$-alkoxy)-$C_1$-$C_4$-alkyl, $C_1$-$C_4$-alkoxycarbonyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, $C(X)NR^2R^3$, (in which X represents oxygen or sulphur, $R^2$ represents hydrogen or $C_1$-$C_4$-alkyl and $R^3$ represents $C_1$-$C_4$-alkyl, $C_1$-$C_4$-haloalkyl, $C_1$-$C_6$-alkoxy, $C_1$-$C_4$-cyanoalkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl or phenyl-$C_1$-$C_4$-alkyl), $C_1$-$C_4$-alkylsulphinyl, $C_1$-$C_4$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_4$-alkyl or $C_1$-$C_4$-haloalkyl), phenyl (which for its part may be substituted by halogen, cyano, nitro, $C_1$-$C_4$-alkyl or $C_1$-$C_4$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl or $C_3$-$C_6$-cycloalkyl), the heteroarylalkyl radicals triazolylalkyl, pyridylalkyl, pyrimidylalkyl or oxadiazolylalkyl (which for their part may be substituted by $C_1$-$C_4$-alkyl) or represents thienyl which is substituted by halogen, nitro, amino, $C_1$-$C_4$-alkylamino, di-$C_1$-$C_4$-alkylamino, $C_1$-$C_4$-haloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkylthio, $C_1$-$C_4$-alkoxy-$C_1$-$C_4$-alkyl, bis($C_1$-$C_4$-alkoxy)-$C_1$-$C_4$-alkyl, $C_1$-$C_4$-alkoxycarbonyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, $C(X)NR^2R^3$, (in which X represents oxygen or sulphur, $R^2$ represents hydrogen or $C_1$-$C_4$-alkyl and $R^3$ represents $C_1$-$C_4$-alkyl, $C_1$-$C_4$-haloalkyl, $C_1$-$C_6$-alkoxy, $C_1$-$C_4$-cyanoalkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl or phenyl-$C_1$-$C_4$-alkyl), $C_1$-$C_4$-alkylsulphinyl, $C_1$-$C_4$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_4$-alkyl or $C_1$-$C_4$-haloalkyl), phenyl (which for its part may be substituted by halogen, cyano, nitro, $C_1$-$C_4$-alkyl or $C_1$-$C_4$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl or $C_3$-$C_6$-cycloalkyl), the heteroarylalkyl radicals triazolylalkyl, pyridylalkyl, pyrimidylalkyl or oxadiazolylalkyl (which for their part may be substituted by $C_1$-$C_4$-alkyl) or represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, $C_1$-$C_4$-alkylamino, di($C_1$-$C_4$-alkyl)amino, $C_1$-$C_4$-alkyl, $C_1$-$C_4$-haloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkylthio, $C_1$-$C_4$-alkoxy-$C_1$-$C_4$-alkyl, bis($C_1$-$C_4$-alkoxy)-$C_1$-$C_4$-alkyl, $C_1$-$C_4$-alkoxycarbonyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, $C(X)NR^2R^3$, (in which X represents oxygen or sulphur, $R^2$ represents hydrogen or $C_1$-$C_4$-alkyl and $R^3$ represents $C_1$-$C_4$-alkyl, $C_1$-$C_4$-haloalkyl, $C_1$-$C_6$-alkoxy, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl or phenyl-$C_1$-$C_4$-alkyl), $C_1$-$C_4$-alkylthio, $C_1$-$C_4$-alkylsulphinyl, $C_1$-$C_4$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_4$-alkyl or $C_1$-$C_4$-haloalkyl), phenyl (which for its part may be substituted by halogen, cyano, nitro, $C_1$-$C_4$-alkyl or $C_1$-$C_4$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl or $C_3$-$C_6$-cycloalkyl), the heteroarylalkyl radicals triazolyl-$C_1$-$C_4$-alkyl, pyridyl-$C_1$-$C_4$-alkyl, pyrimidyl-$C_1$-$C_4$-alkyl or oxadiazolyl-$C_1$-$C_4$-alkyl (which for their part may be substituted by $C_1$-$C_4$-alkyl) or represents cyano-, nitro-, $C_1$-$C_4$-haloalkoxy-, dioxolanyl- or dihydrodioxazinyl-substituted phenyl or
(Id)
$G^1$ represents N, CH or C-halogen,
$G^2$ represents

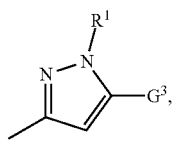

(C)

in which
$R^1$ represents hydrogen or $C_1$-$C_4$-alkyl (in particular methyl) and
$G^3$ represents in each case optionally halogen-, cyano-, nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_1$-$C_4$-alkyl-$C_3$-$C_6$-cycloalkyl-, $C_1$-$C_4$-alkylcarbonyl-, $C_1$-$C_4$-alkoxycarbonyl-, aminocarbonyl-, pyridyl- or pyrimidyl-substituted oxazolinyl, dihydrooxadiazinyl, dihydrodioxazinyl or hydroxypyridyl,
represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl (in particular pyridyl, pyrimidinyl, imidazolyl, pyrazolyl, triazinyl, thiazolyl, thiadiazolyl, oxadiazolyl or oxazolyl), each of which is optionally substituted by halogen, nitro, amino, $C_1$-$C_4$-alkylamino, di($C_1$-$C_4$-alkyl)amino, $C_1$-$C_4$-alkyl, $C_1$-$C_4$-haloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkylthio, $C_1$-$C_4$-alkoxy-$C_1$-$C_4$-alkyl, bis($C_1$-$C_4$-alkoxy)-$C_1$-$C_4$-alkyl, $C_1$-$C_4$-alkoxycarbonyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, $C(X)NR^2R^3$, (in which X represents oxygen or sulphur, $R^2$ represents hydrogen or $C_1$-$C_4$-alkyl and $R^3$ represents $C_1$-$C_4$-alkyl, $C_1$-$C_4$-haloalkyl, $C_1$-$C_6$-alkoxy, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl or phenyl-$C_1$-$C_4$-alkyl), $C_1$-$C_4$-alkylsulphinyl, $C_1$-$C_4$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_4$-alkyl or $C_1$-$C_4$-haloalkyl), phenyl (which for its part may be substituted by halogen, cyano, nitro, $C_1$-$C_4$-alkyl or $C_1$-$C_4$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl or $C_3$-$C_6$-cycloalkyl), the heteroarylalkyl radicals triazolyl-$C_1$-$C_4$-alkyl, pyridyl-$C_1$-$C_4$-alkyl, pyrimidyl-$C_1$-$C_4$-alkyl or oxadiazolyl-$C_1$-$C_4$-alkyl (which for their part may be substituted by $C_1$-$C_4$-alkyl) or
represents optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, dioxolanyl-, piperidinonyl-, pyrrolidinonyl- or dihydrodioxazinyl-substituted phenyl
and also salts and N-oxides of the compounds of the formula (I).

With very particular emphasis, use is made of compounds of the formula (I),

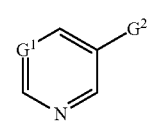

(I)

in which
(Ia)
$G^1$ represents N, CH or C-halogen (in particular CF),
$G^2$ represents

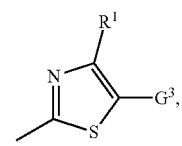

(A)

in which
$R^1$ represents hydrogen or methyl and
$G^3$ represents in each case optionally pyridyl- or pyrimidinyl-substituted oxazolinyl, dihydrooxadiazinyl or hydroxypyridyl, represents pyrazolyl, 1,2,4-oxadiazolyl, pyridyl, pyrimidinyl, 1,3,5-triazinyl, triazinyl or oxadiazolyl, each of which is optionally substituted by halogen (in particular chlorine, bromine), nitro, amino, $C_1$-$C_4$-haloalkyl (in particular $CF_3$, $CF_3CH_2$, $CF_3CF_2$, $CF_2Cl$, $CF_3CF_2CF_2$, $CH_3CHF$), $C_3$-$C_6$-cycloalkyl-$C_1$-$C_4$-alkyl (in particular cyclopropylmethyl), $C_1$-$C_4$-alkoxy-$C_1$-$C_4$-alkyl (in particular methoxymethyl), bis($C_1$-$C_4$-alkoxy)-$C_1$-$C_4$-alkyl (in particular $(CH_3O)_2CH_1$, $C_1$-$C_4$-alkoxycarbonyl (in particular methoxycarbonyl), alpha-hydroxyimino-$C_1$-$C_4$-alkoxycarbonylmethyl, $C(X)NR^2R^3$, (in which X represents oxygen or sulphur, $R^2$ represents hydrogen and $R^3$ represents $C_1$-$C_5$-alkyl (in particular methyl, ethyl, n-propyl, isopropyl, isobutyl, tert-butyl, $(CH_3)_2C(CH_3)_2)$, $C_1$-$C_4$-haloalkyl (in particular $CF_3CH_2$), $C_1$-$C_4$-alkoxy (in particular methoxy, ethoxy, propyloxy) cyano-$C_1$-$C_4$-alkyl (in particular $NCCH_2CH(C_2H_5)$), $C_3$-$C_6$-cycloalkyl (in particular cyclopropyl, cyclopentyl, cyclohexyl), $C_3$-$C_6$-cycloalkyl-$C_1$-$C_4$-alkyl (in particular cyclopropylmethyl), $C_1$-$C_4$-alkoxy-$C_1$-$C_4$-alkyl (in particular $CH_3OCH_2$, $CH_3OCH_2CH(CH_3)$, $CH_3CH_2CH_2OCH_2CH(CH_3)$, $CH_3CH_2OCH_2CH_2$, $CH_3OCH_2CH_2CH_2$, $CH_3OCH_2CHC_2H_5$, $CH_3CH_2OCH_2CH(CH_3)$, $CH_3CH_2OCH_2CH_2CH_2$, $CH_3OC(CH_3)_2$), $C_1$-$C_4$-alkylthio-$C_1$-$C_4$-alkyl (in particular $CH_3SCH_2CH_2$) or phenyl-$C_1$-$C_4$-alkyl (in particular $C_6H_5CH(CH_3)$), $C_1$-$C_4$-alkylthio (in particular methylthio), $C_1$-$C_4$-alkylsulphonyl (in particular $CH_3SO_2$), the heterocyclyl radicals morpholinyl, triazolinonyl, dihydrodioxazinyl, dihydrooxadiazinyl, piperidinonyl, pyrrolidinonyl and pyrazolinonyl (which for their part may be substituted by $C_1$-$C_4$-alkyl (in particular methyl) or $C_1$-$C_4$-haloalkyl (in particular $CF_3$)), phenyl (which for its part may be substituted by halogen (in particular fluorine, chlorine)), the heteroaryl radicals pyrrolyl, pyridyl, pyridyl N-oxide, pyrimidinyl, pyrazolyl, thiazolyl, furanyl, thienyl, triazolyl, oxadiazolyl, thiadiazolyl, pyrazinyl, triazinyl and isoquinolinyl (which for their part may be substituted by halogen (in particular fluorine, chlorine), nitro, $C_1$-$C_4$-alkyl (in particular methyl, ethyl, n-propyl, isopropyl, tert-butyl), $C_1$-$C_4$-haloalkyl (in particular $CF_3$, $CHF_2$, $CFClH$), $C_3$-$C_4$-alkanediyl, (in particular $CH_2CH_2CH_2$), $C_1$-$C_4$-alkoxy (in particular methoxy, ethoxy), $C_3$-$C_6$-cycloalkyl (in particular cyclopropyl, cyclobutyl, cyclopentyl)), the heteroarylalkyl radicals triazolyl-$C_1$-$C_4$-alkyl (in particular triazolylmethyl), pyridyl-$C_1$-$C_4$-alkyl (in particular pyridylmethyl), pyrimidinyl-$C_1$-$C_4$-alkyl (in particular primidinylmethyl) or oxadiazolyl-$C_1$-$C_4$-alkyl (in particular oxadiazolylmethyl (which for their part may be substituted by $C_1$-$C_4$-alkyl (in particular methyl)) or represents optionally halogen- (in particular chlorine-), $C_1$-$C_4$-haloalkyl- (in particular $CF_3$—), dioxolanyl-, piperidinonyl-, pyrrolidinonyl- or dihydrodioxazinyl- substituted phenyl or (Ib)
$G^1$ represents N or C-halogen (in particular CF),
$G^2$ represents

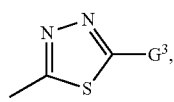
(B)

in which
$G^3$ represents optionally pyrrolyl- or pyrimidinyl-substituted pyridyl or (Ic)
$G^1$ represents CH,
$G^2$ represents

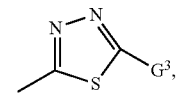
(B)

in which
$G^3$ represents in each case optionally pyrrolyl- or pyrimidinyl-substituted pyrazolyl, pyridyl or pyrimidinyl, or represents $C_1$-$C_4$-haloalkoxy- (in particular $CF_3O$—) substituted phenyl (Id)
$G^1$ represents CH,
$G^2$ represents

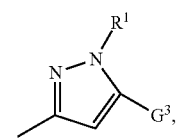
(C)

in which
$R^1$ represents $C_1$-$C_4$-alkyl (in particular methyl) and
$G^3$ represents optionally pyrimidyl-substituted dihydrooxadiazinyl or
represents in each case optionally $C_1$-$C_4$-alkoxy-$C_1$-$C_4$-alkyl- (in particular methoxymethyl-), pyridyl- or pyridyl-$C_1$-$C_4$-alkyl- (in particular pyridylmethyl-) substituted pyrazolyl or pyrimidinyl,
and also salts and N-oxides of the compounds of formula (I).

Radicals substituted by halogen (also abbreviated as "halo"), for example haloalkyl, are mono- or polysubstituted up to the maximum possible number of substituents. In the case of polyhalogenation, the halogen atoms can be identical or different. Here, halogen represents fluorine, chlorine, bromine and iodine, in particular fluorine, chlorine and bromine, with emphasis given to fluorine and chlorine.

The radical "pyrimidyl" is also referred to as "pyrimidinyl".

Preference, particular preference or very particular preference is given to using compounds carrying the substituents listed in each case as being preferred, particularly preferred or very particularly preferred.

Saturated or unsaturated hydrocarbon radicals, such as alkyl or alkenyl, can in each case be straight-chain or branched as far as is possible, including in combination with heteroatoms, such as, for example, in alkoxy.

Optionally substituted radicals can be mono- or polysubstituted, where in the case of polysubstitution the substituents can be identical or different.

The general or preferred radical definitions or illustrations listed above apply to the end products, and, correspondingly, to the starting materials and intermediates. These radical definitions can be combined with one another as desired, i.e. including combinations between the respective preferred ranges.

Preference according to the invention is given to using compounds of the formula (I) which contain a combination of the meanings listed above as being preferred.

Particular preference according to the invention is given to using compounds of the formula (I) which contain a combination of the meanings listed above as being particularly preferred.

Very particular preference according to the invention is given to using compounds of the formula (I) which contain a combination of the meanings listed above as being very particularly preferred.

A group of compounds emphasized for the use according to the invention are the compounds defined under (Ia).

A further group of compounds emphasized for the use according to the invention are the compounds defined under (Ib).

A further group of compounds emphasized for the use according to the invention are the compounds defined under (Ic).

A further group of compounds emphasized for the use according to the invention are the compounds defined under (Id).

In a further emphasized group of compounds (Ia) to be used according to the invention, $G^1$ represents CH.

In a further emphasized group of compounds (Ia) to be used according to the invention, $G^1$ represents N.

In a further emphasized group of compounds (Ia) to be used according to the invention, $G^1$ represents C-halogen.

In a further emphasized group of compounds (Ib) to be used according to the invention, $G^1$ represents N.

In a further emphasized group of compounds (Ib) to be used according to the invention, $G^1$ represents C-halogen.

In a further emphasized group of compounds (Id) to be used according to the invention, $G^1$ represents CH.

In a further emphasized group of compounds (Id) to be used according to the invention, $G^1$ represents N.

In a further emphasized group of compounds (Id) to be used according to the invention, $G^1$ represents C-halogen.

In a further emphasized group of compounds (Ia) to be used according to the invention, $G^1$ represents CH and $R^1$ represents hydrogen.

In a further emphasized group of compounds (Ia) to be used according to the invention, $G^1$ represents N and $R^1$ represents hydrogen.

In a further emphasized group of compounds (Ia) to be used according to the invention, $G^1$ represents C-halogen and $R^1$ represents hydrogen.

In a further emphasized group of compounds (Ia) to be used according to the invention, $G^1$ represents CH and $R^1$ represents methyl.

In a further emphasized group of compounds (Ia) to be used according to the invention, $G^1$ represents N and $R^1$ represents methyl.

In a further emphasized group of compounds (Ia) to be used according to the invention, $G^1$ represents C-halogen and $R^1$ represents methyl.

In a further emphasized group of compounds (Id) to be used according to the invention, $G^1$ represents CH and $R^1$ represents hydrogen.

In a further emphasized group of compounds (Id) to be used according to the invention, $G^1$ represents N and $R^1$ represents hydrogen.

In a further emphasized group of compounds (Id) to be used according to the invention, $G^1$ represents C-halogen and $R^1$ represents hydrogen.

In a further emphasized group of compounds (Id) to be used according to the invention, $G^1$ represents CH and $R^1$ represents methyl.

In a further emphasized group of compounds (Id) to be used according to the invention, $G^1$ represents N and $R^1$ represents methyl.

In a further emphasized group of compounds (Id) to be used according to the invention, $G^1$ represents C-halogen and $R^1$ represents methyl.

If appropriate, the compounds of the formula (I) can be present in different polymorphic forms or as a mixture of different polymorphic forms. The invention provides both the pure polymorphs and the polymorph mixtures, and both can be used according to the invention.

The present invention furthermore relates to novel compounds of the formula (IA)

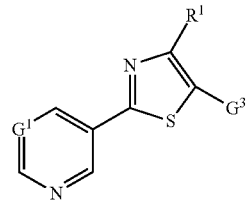

(IA)

in which
$G^1$ represents N, CH or C-halogen,
$R^1$ represents hydrogen and
$G^3$ represents optionally substituted heterocyclyl, represents optionally substituted heteroaryl or represents optionally substituted aryl.

Preference is given to novel compounds of the formula (IA), in which
$G^1$ represents N, CH or C-halogen,
$R^1$ represents hydrogen and
$G^3$ represents in each case optionally halogen-, cyano-, nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, alkylcycloalkyl-, alkylcarbonyl-, alkoxycarbonyl-, aminocarbonyl-, pyridyl- or pyrimidyl-substituted oxazolinyl, dihydrooxadiazinyl, dihydrodioxazinyl or hydroxypyridyl, represents hetaryl from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, in particular pyridyl, pyrimidyl, imidazolyl, pyrazolyl, triazinyl, thiazolyl, thiadiazolyl, oxadiazolyl or oxazolyl, each of which is optionally substituted by halogen, nitro, amino, alkylamino, dialkylamino, alkyl, haloalkyl, cycloalkylalkyl, alkoxy, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, $C(X)NR^2R^3$, (in which X represents oxygen or sulphur, $R^2$ represents hydrogen or alkyl and $R^3$ represents alkyl, haloalkyl, alkoxy, cyanoalkyl, alkynyl, cycloalkyl, cycloalkylalkyl, alkoxyalkyl, alkylthioalkyl or arylalkyl), alkylsulphinyl, alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by alkyl or haloalkyl), phenyl (which for its part may be substituted by halogen, cyano, nitro, alkyl or haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl or cycloalkyl), the heteroarylalkyl radicals triazolylalkyl, pyridylalkyl, pyrimidylalkyl or oxadiazolylalkyl (which for their part may be substituted by alkyl) or represents optionally halogen-, cyano-, alkyl-, haloalkyl-, alkoxy-, haloalkoxy-, dioxolanyl-, piperidinonyl-, pyrrolidinonyl- or dihydrodioxazinyl-substituted phenyl.

Particular preference is given to novel compounds of the formula (IA) in which $G^1$ represents N, CH or C-halogen, $R^1$ represents hydrogen and $G^3$ represents in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl-$C_3$-$C_6$-cycloalkyl-, $C_1$-$C_6$-alkylcarbonyl-, $C_1$-$C_6$-alkoxycarbonyl-, aminocarbonyl-, pyridyl- or pyrimidyl-substituted oxazolinyl, dihydrooxadiazinyl, dihydrodioxazinyl or hydroxypyridyl, represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, $C_1$-$C_6$-alkylamino, di($C_1$-$C_6$-alkyl)amino, $C_1$-$C_6$-alkyl, $C_1$-$C_6$-haloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkylthio, $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_1$-$C_6$-alkoxyimino-$C_1$-$C_6$-alkoxycarbonylmethyl, $C(X)NR^2R^3$, (in which X represents oxygen or sulphur, $R^2$ represents hydrogen or $C_1$-$C_6$-alkyl and $R^3$ represents $C_1$-$C_6$-alkyl, $C_1$-$C_6$-haloalkyl, $C_1$-$C_6$-alkoxy, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkylthio-$C_1$-$C_6$-alkyl or phenyl-$C_1$-$C_6$-alkyl), $C_1$-$C_6$-alkylsulphinyl, $C_1$-$C_6$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_6$-alkyl or $C_1$-$C_6$-haloalkyl), phenyl (which for its part may be substituted by halogen, cyano, nitro, $C_1$-$C_6$-alkyl or $C_1$-$C_6$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl or $C_3$-$C_6$-cycloalkyl), the heteroarylalkyl radicals triazolyl-$C_1$-$C_6$-alkyl, pyridyl-$C_1$-$C_6$-alkyl, pyrimidyl-$C_1$-$C_6$-alkyl or oxadiazolyl-$C_1$-$C_6$-alkyl (which for their part may be substituted by $C_1$-$C_6$-alkyl) or represents optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, dioxolanyl-, piperidinonyl-, pyrrolidinonyl- or dihydrodioxazinyl-substituted phenyl.

Very particular preference is given to novel compounds of the formula (IA) in which $G^1$ represents N, CH or C-halogen, $R^1$ represents hydrogen and $G^3$ represents in each case optionally halogen-, cyano-, nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_1$-$C_4$-alkyl-$C_3$-$C_6$-cycloalkyl-, $C_1$-$C_4$-alkylcarbonyl-, $C_1$-$C_4$-alkoxycarbonyl-, aminocarbonyl-, pyridyl- or pyrimidyl-substituted oxazolinyl, dihydrooxadiazinyl, dihydrodioxazinyl or hydroxypyridyl, represents pyrrolyl, pyrazoyl, imidazolyl, 1,2,3-triazolyl, 1,2,4-triazolyl, oxazolyl, isoxazoyl, thiazolyl, isothiazolyl, 1,2,3-oxadiazolyl, 1,2,4-oxadiazoyl, 1,3,4-oxadiazoyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, $C_1$-$C_4$-alkylamino, di($C_1$-$C_4$-alkyl)amino, $C_1$-$C_4$-alkyl, $C_1$-$C_4$-haloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkylthio, $C_1$-$C_4$-alkoxy-$C_1$-$C_4$-alkyl, bis($C_1$-$C_4$-alkoxy)-$C_1$-$C_4$-alkyl, $C_1$-$C_4$-alkoxycarbonyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, C(X)NR$^2$R$^3$, (in which X represents oxygen or sulphur, R$^2$ represents hydrogen or $C_1$-$C_4$-alkyl and R$^3$ represents $C_1$-$C_5$-alkyl, $C_1$-$C_4$-haloalkyl, $C_1$-$C_4$-alkoxy, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl or phenyl-$C_1$-$C_4$-alkyl), $C_1$-$C_4$-alkylsulphinyl, $C_1$-$C_4$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_4$-alkyl or $C_1$-$C_4$-haloalkyl), phenyl (which for its part may be substituted by halogen, cyano, nitro, $C_1$-$C_4$-alkyl or $C_1$-$C_4$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl or $C_3$-$C_6$-cycloalkyl), the heteroarylalkyl radicals triazolyl-$C_1$-$C_4$-alkyl, pyridyl-$C_1$-$C_4$-alkyl, pyrimidyl-$C_1$-$C_4$-alkyl or oxadiazolyl-$C_1$-$C_4$-alkyl (which for their part may be substituted by $C_1$-$C_4$-alkyl) or represents optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, dioxolanyl-, piperidinonyl-, pyrrolidinonyl- or dihydrodioxazinyl-substituted phenyl.

Very particular emphasis is given to novel compounds of the formula (IA) in which G$^1$ represents N, CH or C-halogen (in particular CF), R$^1$ represents hydrogen and G$^3$ represents in each case optionally pyridyl- or pyrimidinyl-substituted oxazolinyl, dihydrooxadiazinyl or hydroxypyridyl, represents pyrazolyl, 1,2,4-oxadiazolyl, pyridyl, pyrimidinyl, 1,3,5-triazinyl, triazinyl or oxadiazolyl, each of which is optionally substituted by halogen (in particular chlorine, bromine), nitro, amino, $C_1$-$C_4$-haloalkyl (in particular CF$_3$, CF$_3$CH$_2$, CF$_3$CF$_2$, CF$_2$Cl, CF$_3$CF$_2$CF$_2$, CH$_3$CHF), $C_3$-$C_6$-cycloalkyl-$C_1$-$C_4$-alkyl (in particular cyclopropylmethyl), $C_1$-$C_4$-alkoxy-$C_1$-$C_4$-alkyl (in particular methoxymethyl), bis($C_1$-$C_4$-alkoxy)-$C_1$-$C_4$-alkyl (in particular (CH$_3$O)$_2$CH), $C_1$-$C_4$-alkoxycarbonyl (in particular methoxycarbonyl), alpha-hydroxyimino-$C_1$-$C_4$-alkoxycarbonylmethyl, C(X)NR$^2$R$^3$, (in which X represents oxygen or sulphur, R$^2$ represents hydrogen and R$^3$ represents $C_1$-$C_6$-alkyl (in particular methyl, ethyl, n-propyl, isopropyl, isobutyl, tert-butyl, (CH$_3$)$_2$C(CH$_3$)$_2$), $C_1$-$C_4$-haloalkyl (in particular CF$_3$CH$_2$), $C_1$-$C_4$-alkoxy (in particular methoxy, ethoxy, propyloxy) cyano-$C_1$-$C_4$-alkyl (in particular NCCH$_2$CH(C$_2$H$_5$)), $C_3$-$C_6$-cycloalkyl (in particular cyclopropyl, cyclopentyl, cyclohexyl), $C_3$-$C_6$-cycloalkyl-$C_1$-$C_4$-alkyl (in particular cyclopropylmethyl), $C_1$-$C_4$-alkoxy-$C_1$-$C_4$-alkyl (in particular CH$_3$OCH$_2$CH(CH$_3$), CH$_3$CH$_2$CH$_2$OCH$_2$CH(CH$_3$), CH$_3$CH$_2$OCH$_2$CH$_2$, CH$_3$OCH$_2$CH$_2$CH$_2$, CH$_3$OCH$_2$CHC$_2$H$_5$, CH$_3$CH$_2$OCH$_2$CH(CH$_3$), CH$_3$CH$_2$OCH$_2$CH$_2$CH$_2$, CH$_3$OC(CH$_3$)$_2$), $C_1$-$C_4$-alkylthio-$C_1$-$C_4$-alkyl (in particular CH$_3$SCH$_2$CH$_2$) or phenyl-$C_1$-$C_4$-alkyl (in particular C$_6$H$_5$CH(CH$_3$)), $C_1$-$C_4$-alkylthio (in particular methylthio), $C_1$-$C_4$-alkylsulphonyl (in particular CH$_3$SO$_2$), the heterocyclyl radicals morpholinyl, triazolinonyl, dihydrodioxazinyl, dihydrooxadiazinyl, piperidinonyl, pyrrolidinonyl and pyrazolinonyl (which for their part may be substituted by $C_1$-$C_4$-alkyl (in particular methyl) or $C_1$-$C_4$-haloalkyl (in particular CF$_3$)), phenyl (which for its part may be substituted by halogen (in particular fluorine, chlorine)), the heteroaryl radicals pyrrolyl, pyridyl, pyridyl N-oxide, pyrimidinyl, pyrazolyl, thiazolyl, furanyl, thienyl, triazolyl, oxadiazolyl, thiadiazolyl, pyrazinyl, triazinyl and isoquinolinyl (which for their part may be substituted by halogen (in particular fluorine, chlorine), nitro, $C_1$-$C_4$-alkyl (in particular methyl, ethyl, n-propyl, isopropyl, tert-butyl), $C_1$-$C_4$-haloalkyl (in particular CF$_3$, CHF$_2$, CFClH), $C_3$-$C_4$-alkanediyl, (in particular CH$_2$CH$_2$CH$_2$), $C_1$-$C_4$-alkoxy (in particular methoxy, ethoxy), $C_3$-$C_6$-cycloalkyl (in particular cyclopropyl, cyclobutyl, cyclopentyl)), the heteroarylalkyl radicals triazolyl-$C_1$-$C_4$-alkyl (in particular triazolylmethyl), pyridyl-$C_1$-$C_4$-alkyl (in particular pyridylmethyl), pyrimidinyl-$C_1$-$C_4$-alkyl (in particular primidinylmethyl) or oxadiazolyl-$C_1$-$C_4$-alkyl (in particular oxadiazolylmethyl (which for their part may be substituted by $C_1$-$C_4$-alkyl (in particular methyl)) or represents optionally halogen- (in particular chlorine-), $C_1$-$C_4$-haloalkyl- (in particular CF$_3$—), dioxolanyl-, piperidinonyl-, pyrrolidinonyl- or dihydrodioxazinyl-substituted phenyl.

The invention also relates to novel compounds of the formula (IB-1)

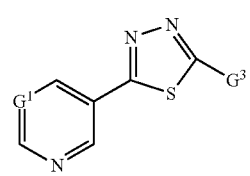

(IB-1)

in which

G$^1$ represents N or C-halogen,

G$^3$ represents optionally substituted heterocyclyl, represents optionally substituted heteroaryl or represents optionally substituted phenyl.

Preference is given to novel compounds of the formula (IB-1), in which

G$^1$ represents N or C-halogen,

G$^3$ represents in each case optionally halogen-, cyano-, nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, alkylcycloalkyl-, alkylcarbonyl-, alkoxycarbonyl-, aminocarbonyl-, pyridyl- or pyrimidyl-substituted oxazolinyl, dihydrooxadiazinyl, dihydrodioxazinyl or hydroxypyridyl, represents hetaryl from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, in particular pyridyl, pyrimidyl, imidazolyl, pyrazolyl, triazinyl, thiazolyl, thiadiazolyl, oxadiazolyl or oxazolyl, each of which is optionally substituted by halogen, nitro, amino, alkylamino, dialkylamino, alkyl, haloalkyl, cycloalkylalkyl, alkoxy, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, C(X)NR$^2$R$^3$, (in which X represents oxygen or sulphur, R$^2$ represents hydrogen or alkyl and R$^3$ represents alkyl, haloalkyl, alkoxy, cyanoalkyl, alkynyl, cycloalkyl, cycloalkylalkyl, alkoxyalkyl, alkylthioalkyl or arylalkyl), alkylthio, alkylsulphinyl, alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by alkyl or haloalkyl), phenyl (which for its part may be substituted by halogen, cyano, nitro, alkyl or haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl or cycloalkyl), the heteroarylalkyl radicals triazolylalkyl, pyridylalkyl, pyrimidylalkyl or oxadiazolylalkyl (which for their part may be substituted by alkyl) or represents optionally halogen-, cyano-, alkyl-, haloalkyl-, alkoxy-, haloalkoxy-, dioxolanyl-, piperidinonyl-, pyrrolidinonyl- or dihydrodioxazinyl-substituted phenyl.

Particular preference is given to novel compounds of the formula (IB-1) in which G$^1$ represents N or C-halogen, G$^3$ represents in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl-$C_3$-$C_6$-cycloalkyl-, $C_1$-$C_6$-alkylcarbonyl-, $C_1$-$C_6$-alkoxycarbonyl-, aminocarbonyl-, pyridyl- or pyrimidyl-substituted oxazolinyl, dihydrooxadiazinyl, dihydrodioxazinyl or hydroxypyridyl, represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, $C_1$-$C_6$-alkylamino, di($C_1$-$C_6$-alkyl)amino, $C_1$-$C_6$-alkyl, $C_1$-$C_6$-haloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkylthio, $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_6$-$C_6$-alkoxyimino-$C_1$-$C_6$-alkoxycarbonylmethyl, C(X)NR$^2$R$^3$, (in which X represents oxygen or sulphur, R$^2$ represents hydrogen or $C_1$-$C_6$-alkyl and R$^3$ represents $C_1$-$C_6$-alkyl, $C_1$-$C_6$-haloalkyl, $C_1$-$C_6$-alkoxy, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkylthio-$C_1$-$C_6$-alkyl or phenyl-$C_1$-$C_6$-alkyl), $C_1$-$C_6$-alkylsulphinyl, $C_1$-$C_6$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_6$-alkyl or $C_1$-$C_1$-haloalkyl), phenyl (which for its part may be substituted by halogen, cyano, nitro, $C_1$-$C_6$-alkyl or $C_1$-$C_6$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl or $C_3$-$C_6$-cycloalkyl), the heteroarylalkyl radicals triazolyl-$C_1$-$C_6$-alkyl, pyridyl-$C_1$-$C_6$-alkyl pyrimidyl-$C_1$-$C_6$-alkyl or oxadiazolyl-$C_1$-$C_6$-alkyl (which for their part may be substituted by $C_1$-$C_6$-alkyl) or represents optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, dioxolanyl-, piperidinonyl-, pyrrolidinonyl- or dihydrodioxazinyl-substituted phenyl.

Very particular preference is given to novel compounds of the formula (IB-1) in which G$^1$ represents N or C-halogen, G$^3$ represents in each case optionally halogen-, cyano-, nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_1$-$C_4$-alkyl-$C_3$-$C_6$-cycloalkyl-, $C_1$-$C_4$-alkylcarbonyl-, $C_1$-$C_4$-alkoxycarbonyl-, aminocarbonyl-, pyridyl- or pyrimidyl-substituted oxazolinyl, dihydrooxadiazinyl, dihydrodioxazinyl or hydroxypyridyl, represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, $C_1$-$C_4$-alkylamino, di($C_1$-$C_4$-alkyl)amino, $C_1$-$C_4$-alkyl, $C_1$-$C_4$-haloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkylthio, $C_1$-$C_4$-alkoxy-$C_1$-$C_4$-alkyl, bis($C_1$-$C_4$-alkoxy)-$C_1$-$C_4$-alkyl, $C_1$-$C_4$-alkoxycarbonyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, $C(X)NR^2R^3$, (in which X represents oxygen or sulphur, $R^2$ represents hydrogen or $C_1$-$C_4$-alkyl and $R^3$ represents $C_1$-$C_4$-alkyl, $C_1$-$C_4$-haloalkyl, $C_1$-$C_4$-alkoxy, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl or phenyl-$C_1$-$C_4$-alkyl), $C_1$-$C_4$-alkylsulphinyl, $C_1$-$C_4$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_4$-alkyl or $C_1$-$C_4$-haloalkyl), phenyl (which for its part may be substituted by halogen, cyano, nitro, $C_1$-$C_4$-alkyl or $C_1$-$C_4$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl or $C_3$-$C_6$-cycloalkyl), the heteroarylalkyl radicals triazolyl-$C_1$-$C_4$-alkyl, pyridyl-$C_1$-$C_4$-alkyl, pyrimidyl-$C_1$-$C_4$-alkyl or oxadiazolyl-$C_1$-$C_4$-alkyl (which for their part may be substituted by $C_1$-$C_4$-alkyl) or represents optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, dioxolanyl-, piperidinonyl-, pyrrolidinonyl- or dihydrodioxazinyl-substituted phenyl.

Very particular emphasis is given to novel compounds of the formula (IB-1) in which $G^1$ represents N or C-halogen (in particular CF), and $G^3$ represents optionally pyrimidinyl-substituted pyridyl.

The invention furthermore also relates to novel compounds of the formula (IB-2)

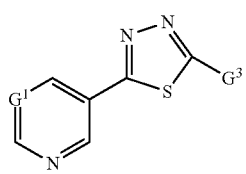

(IB-2)

in which $G^1$ represents C—H and $G^3$ represents in each case optionally halogen-, cyano-, nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, alkylcycloalkyl-, alkylcarbonyl-, alkoxycarbonyl-, aminocarbonyl-, pyridyl- or pyrimidyl-substituted oxazolinyl, dihydrooxadiazinyl, dihydrodioxazinyl or hydroxypyridyl or represents furanyl, thienyl or pyridyl, each of which is substituted by fluorine, nitro, amino, alkylamino, dialkylamino, haloalkyl, cycloalkylalkyl, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, $C(X)NR^2R^3$, (in which X represents oxygen or sulphur, $R^2$ represents hydrogen or alkyl and $R^3$ represents alkyl, haloalkyl, alkoxy, cyanoalkyl, alkynyl, cycloalkyl, cycloalkylalkyl, alkoxyalkyl, alkylthioalkyl or arylalkyl), alkylsulphinyl, alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by alkyl or haloalkyl), phenyl (which for its part may be substituted by halogen, cyano, nitro, alkyl or haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl), the heteroarylalkyl radicals triazolylalkyl, pyridylalkyl, pyrimidylalkyl or oxadiazolylalkyl (which for their part may be substituted by alkyl) or represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl, each of which is optionally substituted by halogen, nitro, amino, alkylamino, dialkylamino, alkyl, haloalkyl, cycloalkylalkyl, alkoxy, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, $C(X)NR^2R^3$, (in which X represents oxygen or sulphur, $R^2$ represents hydrogen or alkyl and $R^3$ represents alkyl, haloalkyl, alkoxy, cyanoalkyl, alkynyl, cycloalkyl, cycloalkylalkyl, alkoxyalkyl, alkylthioalkyl or arylalkyl), alkylsulphinyl, alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by alkyl or haloalkyl), phenyl (which for its part may be substituted by halogen, cyano, nitro, alkyl or haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl or cycloalkyl), the heteroarylalkyl radicals triazolylalkyl, pyridylalkyl, pyrimidylalkyl or oxadiazolylalkyl (which for their part may be substituted by alkyl) or represents cyano-, nitro-, haloalkoxy-, dioxolanyl-, piperidinonyl-, pyrrolidinonyl- or dihydrodioxazinyl-substituted phenyl.

Particular preference is given to compounds of the formula (IB-2) in which $G^3$ represents in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl-$C_3$-$C_6$-cycloalkyl-, $C_1$-$C_6$-alkylcarbonyl-, $C_1$-$C_6$-alkoxycarbonyl-, aminocarbonyl-, pyridyl- or pyrimidyl-substituted oxazolinyl, dihydrooxadiazinyl, dihydrodioxazinyl or hydroxypyridyl or represents furanyl, thienyl or pyridyl, each of which is substituted by fluorine, nitro, amino, $C_1$-$C_6$-alkylamino, di-$C_1$-$C_6$-alkylamino, $C_1$-$C_6$-haloalkyl, $C_3$-$C_6$-cycloalkyl-$C_1$-$C_6$-alkyl, $C_1$-$C_6$-haloalkoxy, $C_1$-$C_6$-alkylthio, $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_1$-$C_6$-alkoxyimino-$C_1$-$C_6$-alkoxycarbonylmethyl, $C(X)NR^2R^3$, (in which X represents oxygen or sulphur, $R^2$ represents hydrogen or $C_1$-$C_6$-alkyl and $R^3$ represents $C_1$-$C_6$-alkyl, $C_1$-$C_6$-haloalkyl, $C_1$-$C_6$-alkoxy, $C_1$-$C_6$-cyanoalkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkylthio-$C_1$-$C_6$-alkyl or phenyl-$C_1$-$C_6$-alkyl), $C_1$-$C_6$-alkylsulphinyl, $C_1$-$C_6$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_6$-alkyl or $C_1$-$C_6$-haloalkyl), phenyl (which for its part may be substituted by halogen, cyano, nitro, $C_1$-$C_6$-alkyl or $C_1$-$C_6$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl or $C_3$-$C_6$-cycloalkyl), the heteroarylalkyl radicals triazolylalkyl, pyridylalkyl, pyrimidylalkyl or oxadiazolylalkyl (which for their part may be substituted by $C_1$-$C_6$-alkyl) or represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl (in particular pyridyl, pyrimidyl, imidazolyl, pyrazolyl, triazolyl, thiazolyl, thiadiazolyl, oxadiazolyl or oxazolyl), each of which is optionally substituted by halogen, nitro, amino, $C_1$-$C_6$-alkylamino, di($C_1$-$C_6$-alkyl)amino, $C_1$-$C_6$-alkyl, $C_1$-$C_6$-haloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkylthio, $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_6$-$C_6$-alkoxyimino-$C_1$-$C_6$-alkoxycarbonylmethyl, $C(X)NR^2R^3$, (in which X represents oxygen or sulphur, $R^2$ represents hydrogen or $C_1$-$C_6$-alkyl and $R^3$ represents $C_1$-$C_6$-alkyl, $C_1$-$C_6$-haloalkyl, $C_1$-$C_6$-alkoxy, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkylthio-$C_1$-$C_6$-alkyl or phenyl-$C_1$-$C_6$-alkyl), $C_1$-$C_6$-alkylthio, $C_1$-$C_6$-alkylsulphinyl, $C_1$-$C_6$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_6$-alkyl or $C_1$-$C_6$-haloalkyl), phenyl (which for its part may be substituted by halogen, cyano, nitro, $C_1$-$C_6$-alkyl or $C_1$-$C_6$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl or $C_3$-$C_6$-cycloalkyl), the heteroarylalkyl radicals triazolyl-$C_1$-$C_6$-alkyl, pyridyl-$C_1$-$C_6$-alkyl, pyrimidyl-$C_1$-$C_6$-alkyl or oxadiazolyl-$C_1$-$C_6$-alkyl (which for their part may be substituted by $C_1$-$C_6$-alkyl) or represents cyano-, nitro-, $C_1$-$C_6$-haloalkoxy-, dioxolanyl-, piperidinonyl-, pyrrolidinonyl- or dihydrodioxazinyl-substituted phenyl.

Very particular preference is given to compounds of the formula (IB-2) in which $G^3$ represents in each case optionally halogen-, cyano-, nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_1$-$C_4$-alkyl-$C_3$-$C_6$-cycloalkyl-, $C_1$-$C_4$-alkylcarbonyl-, $C_1$-$C_4$-alkoxycarbonyl-, aminocarbonyl-, pyridyl- or pyrimidyl-substituted oxazolinyl, dihydrooxadiazinyl, dihydrodioxazinyl or hydroxypyridyl, or represents furanyl, thienyl or pyridyl, each of which is substituted by fluorine, nitro, amino, $C_1$-$C_4$-alkylamino, di-$C_1$-$C_4$-alkylamino, $C_1$-$C_4$-haloalkyl, $C_3$-$C_6$-cycloalkylalkyl, $C_1$-$C_4$-haloalkoxy, $C_1$-$C_4$-alkylthio, $C_1$-$C_4$-alkoxy-$C_1$-$C_4$-alkyl, bis($C_1$-$C_4$-alkoxy)-$C_1$-$C_4$-alkyl, $C_1$-$C_4$-alkoxycarbonyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, $C(X)NR^2R^3$, (in which X represents oxygen or sulphur, $R^2$ represents hydrogen or $C_1$-$C_4$-alkyl and $R^3$ represents $C_1$-$C_4$-alkyl, $C_1$-$C_4$-haloalkyl, $C_1$-$C_4$-alkoxy, cyano-$C_1$-$C_4$-alkyl, $C_2$-$C_4$- alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl or phenyl-$C_1$-$C_4$-alkyl), $C_1$-$C_4$-alkylsulphinyl, $C_1$-$C_4$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_4$-alkyl or $C_1$-$C_4$-haloalkyl), phenyl (which for its part may be substituted by halogen, cyano, nitro, $C_1$-$C_4$-alkyl or $C_1$-$C_4$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl or $C_3$-$C_6$-cycloalkyl), the heteroarylalkyl radicals triazolyl-$C_1$-$C_4$-alkyl, pyridyl-$C_1$-$C_4$-alkyl, pyrimidyl-$C_1$-$C_4$-alkyl or oxadiazolyl $C_1$-$C_4$-alkyl (which for their part may be substituted by $C_1$-$C_4$-alkyl) or represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl (in particular, pyrimidyl, imidazolyl, pyrazolyl, triazinyl, thiazolyl, thiadiazolyl, oxadiazolyl or oxazolyl), each of which is optionally substituted by halogen, nitro, amino, $C_1$-$C_4$-alkylamino, di($C_1$-$C_4$-alkyl)amino, $C_1$-$C_4$-alkyl, $C_1$-$C_4$-haloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkylthio, $C_1$-$C_4$-alkoxy-$C_1$-$C_4$-alkyl, bis($C_1$-$C_4$-alkoxy)-$C_1$-$C_4$-alkyl, $C_1$-$C_4$-alkoxycarbonyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, $C(X)NR^2R^3$, (in which X represents oxygen or sulphur, $R^2$ represents hydrogen or $C_1$-$C_4$-alkyl and $R^3$ represents $C_1$-$C_4$-alkyl, $C_1$-$C_4$-haloalkyl, $C_1$-$C_4$-alkoxy, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl or phenyl-$C_1$-$C_4$-alkyl), $C_1$-$C_4$-alkylsulphinyl, $C_1$-$C_4$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_4$-alkyl or $C_1$-$C_4$-haloalkyl), phenyl (which for its part may be substituted by halogen, cyano, nitro, $C_1$-$C_4$-alkyl or $C_1$-$C_4$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl or $C_3$-$C_6$-cycloalkyl), the heteroarylalkyl radicals triazolyl-$C_1$-$C_4$-alkyl, pyridyl-$C_1$-$C_4$-alkyl, pyrimidyl-$C_1$-$C_4$-alkyl or oxadiazolyl-$C_1$-$C_4$-alkyl (which for their part may be substituted by $C_1$-$C_4$-alkyl) or represents cyano-, nitro-, $C_1$-$C_4$-haloalkoxy-, dioxolanyl-, piperidinonyl-, pyrrolidinonyl- or dihydrodioxazinyl-substituted phenyl.

Very particular emphasis is given to novel compounds of the formula (I-B-2) in which $G^1$ represents CH, and $G^3$ represents in each case optionally pyrrolyl- or pyrimidinyl-substituted pyrazolyl, pyridyl or pyrimidinyl, or represents $C_1$-$C_4$-haloalkoxy- (in particular $CF_3O$—) substituted phenyl.

The invention also relates to novel compounds of the formula (IC-1)

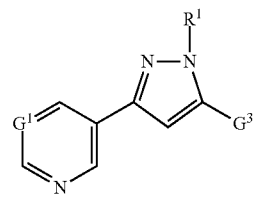

(IC-1)

in which $G^1$ represents C—H, $R^1$ represents alkyl (in particular methyl) and $G^3$ represents optionally substituted heterocyclyl, represents optionally substituted heteroaryl or represents optionally substituted phenyl.

Preference is given to novel compounds of the formula (IC-1) in which $G^1$ represents C—H, $R^1$ represents alkyl (in particular methyl) and $G^3$ represents in each case optionally halogen-, cyano-, nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, alkylcycloalkyl-, alkylcarbonyl-, alkoxycarbonyl-, aminocarbonyl-, pyridyl- or pyrimidyl-substituted oxazolinyl, dihydrooxadiazinyl, dihydrodioxazinyl or hydroxypyridyl, represents hetaryl from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, in particular pyridyl, pyrimidyl, imidazolyl, pyrazolyl, triazinyl, thiazolyl, thiadiazolyl, oxadiazolyl or oxazolyl, each of which is optionally substituted by halogen, nitro, amino, alkylamino, dialkylamino, alkyl, haloalkyl, cycloalkylalkyl, alkoxy, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, $C(X)NR^2R^3$, (in which X represents oxygen or sulphur, $R^2$ represents hydrogen or alkyl and $R^3$ represents alkyl, haloalkyl, alkoxy, cyanoalkyl, alkynyl, cycloalkyl, cycloalkylalkyl, alkoxyalkyl, alkylthioalkyl or arylalkyl), alkylthio, alkylsulphinyl, alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by alkyl or haloalkyl), phenyl (which for its part may be substituted by halogen, cyano, nitro, alkyl or haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl or cycloalkyl), the heteroarylalkyl radicals triazolylalkyl, pyridylalkyl, pyrimidylalkyl or oxadiazolylalkyl (which for their part may be substituted by alkyl) or represents optionally halogen-, cyano-, alkyl-, haloalkyl-, alkoxy-, haloalkoxy-, dioxolanyl-, piperidinonyl-, pyrrolidinonyl- or dihydrodioxazinyl-substituted phenyl.

Particular preference is given to novel compounds of the formula (IC-1) in which $G^1$ represents C—H, $R^1$ represents methyl and $G^3$ represents in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl-$C_3$-$C_6$-cycloalkyl-, $C_1$-$C_6$-alkylcarbonyl-, $C_1$-$C_6$-alkoxycarbonyl-, aminocarbonyl-, pyridyl- or pyrimidyl-substituted oxazolinyl, dihydrooxadiazinyl, dihydrodioxazinyl or hydroxypyridyl, represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, $C_1$-$C_6$-alkylamino, di($C_1$-$C_6$-alkyl)amino, $C_1$-$C_6$-alkyl, $C_1$-$C_6$-haloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkylthio, $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_6$-$C_6$-alkoxyimino-$C_1$-$C_6$-alkoxycarbonylmethyl, $C(X)NR^2R^3$, (in which X represents oxygen or sulphur, $R^2$ represents hydrogen or $C_1$-$C_6$-alkyl and $R^3$ represents $C_1$-$C_6$-alkyl, $C_1$-$C_6$-haloalkyl, $C_1$-$C_6$-alkoxy, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkylthio-$C_1$-$C_6$-alkyl or phenyl-$C_1$-$C_6$-alkyl), $C_1$-$C_6$-alkylsulphinyl, $C_1$-$C_6$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_6$-alkyl or $C_1$-$C_6$-haloalkyl), phenyl (which for its part may be substituted by halogen, cyano, nitro, $C_1$-$C_6$-alkyl or $C_1$-$C_6$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl or $C_3$-$C_6$-cycloalkyl), the heteroarylalkyl radicals triazolyl-$C_1$-$C_6$-alkyl, pyridyl-$C_1$-$C_6$-alkyl, pyrimidyl-$C_1$-$C_6$-alkyl or oxadiazolyl-$C_1$-$C_6$-alkyl (which for their part may be substituted by $C_1$-$C_6$-alkyl) or represents optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, dioxolanyl-, piperidinonyl-, pyrrolidinonyl- or dihydrodioxazinyl-substituted phenyl.

Very particular preference is given to novel compounds of the formula (IC-1) in which $G^1$ represents C—H, $R^1$ represents methyl and $G^3$ represents in each case optionally halogen-, cyano-, nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_1$-$C_4$-alkyl-$C_3$-$C_6$-cycloalkyl-, $C_1$-$C_4$-alkylcarbonyl-, $C_1$-$C_4$-alkoxycarbonyl-, aminocarbonyl-, pyridyl- or pyrimidyl-substituted oxazolinyl, dihydrooxadiazinyl, dihydrodioxazinyl or hydroxypyridyl, represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, $C_1$-$C_4$-alkylamino, di($C_1$-$C_4$-alkyl)amino, $C_1$-$C_4$-alkyl, $C_1$-$C_4$-haloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkylthio, $C_1$-$C_4$-alkoxy-$C_1$-$C_4$-alkyl, bis($C_1$-$C_4$-alkoxy)-$C_1$-$C_4$-alkyl, $C_1$-$C_4$-alkoxycarbonyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, C(X)NR$^2$R$^3$, (in which X represents oxygen or sulphur, R$^2$ represents hydrogen or $C_1$-$C_4$-alkyl and R$^3$ represents $C_1$-$C_5$-alkyl, $C_1$-$C_4$-haloalkyl, $C_1$-$C_4$-alkoxy, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl or phenyl-$C_1$-$C_4$-alkyl), $C_1$-$C_4$-alkylsulphinyl, $C_1$-$C_4$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_4$-alkyl or $C_1$-$C_4$-haloalkyl), phenyl (which for its part may be substituted by halogen, cyano, nitro, $C_1$-$C_4$-alkyl or $C_1$-$C_4$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl or $C_3$-$C_6$-cycloalkyl), the heteroarylalkyl radicals triazolyl-$C_1$-$C_4$-alkyl, pyridyl-$C_1$-$C_4$-alkyl, pyrimidyl-$C_1$-$C_4$-alkyl or oxadiazolyl-$C_1$-$C_4$-alkyl (which for their part may be substituted by $C_1$-$C_4$-alkyl) or represents optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, dioxolanyl-, piperidinonyl-, pyrrolidinonyl- or dihydrodioxazinyl-substituted phenyl.

Very particular emphasis is given to novel compounds of the formula (IC-1) in which
G$^1$ represents CH,
and
R$^1$ represents $C_1$-$C_4$-alkyl (in particular methyl) and
G$^3$ represents optionally pyrimidyl-substituted dihydrooxadiazinyl or
represents in each case optionally $C_1$-$C_4$-alkoxy-$C_1$-$C_4$-alkyl- (in particular methoxymethyl)-, pyridyl- or pyridyl-$C_1$-$C_4$-alkyl- (in particular pyridylmethyl-) substituted pyrazolyl or pyrimidinyl.

The invention furthermore also relates to novel compounds of the formula (IC-2)

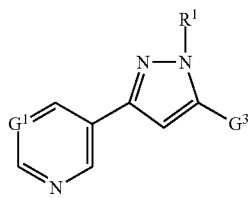

(IC-2)

in which
G$^1$ represents C—H,
R$^1$ represents hydrogen and
G$^3$ represents optionally substituted heterocyclyl, represents optionally substituted heteroaryl or represents optionally alkyl-, haloalkyl-, haloalkoxy-, dioxolanyl- or dihydrodioxazinyl-substituted phenyl.

Preference is also given to novel compounds of the formula (IC-2) in which
G$^1$ represents C—H,
R$^1$ represents hydrogen and
G$^3$ represents in each case optionally halogen-, cyano-, nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, alkylcycloalkyl-, alkylcarbonyl-, alkoxycarbonyl-, aminocarbonyl-pyridyl- or pyrimidyl-substituted oxazolinyl, dihydrooxadiazinyl, dihydrodioxazinyl or hydroxypyridyl,
represents pyridyl, pyrimidyl, imidazolyl, pyrazolyl, triazinyl, thiazolyl, thiadiazolyl, oxadiazolyl or oxazolyl, each of which is optionally substituted by halogen, nitro, amino, alkylamino, dialkylamino, alkyl, haloalkyl, cycloalkylalkyl, alkoxy, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, C(X)NR$^2$R$^3$, (in which X represents oxygen or sulphur, R$^2$ represents hydrogen or alkyl and R$^3$ represents alkyl, haloalkyl, alkoxy, cyanoalkyl, alkynyl, cycloalkyl, cycloalkylalkyl, alkoxyalkyl, alkylthioalkyl or arylalkyl), alkylsulphinyl, alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by alkyl or haloalkyl), phenyl (which for its part may be substituted by halogen, cyano, nitro, alkyl or haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl), the heteroarylalkyl radicals triazolylalkyl, pyridylalkyl, pyrimidylalkyl or oxadiazolylalkyl (which for their part may be substituted by alkyl) or represents optionally alkyl-, haloalkyl-, haloalkoxy-, dioxolanyl-, piperidinonyl-, pyrrolidinonyl- or dihydrodioxazinyl-substituted phenyl.

Particular preference is given to novel compounds of the formula (IC-2) in which
G$^1$ represents C—H,
R$^1$ represents hydrogen and
G$^3$ represents in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl-$C_3$-$C_6$-cycloalkyl-, $C_1$-$C_6$-alkylcarbonyl-, $C_1$-$C_6$-alkoxycarbonyl-, aminocarbonyl-, pyridyl- or pyrimidyl-substituted oxazolinyl, dihydrooxadiazinyl, dihydrodioxazinyl or hydroxypyridyl,
represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl (in particular pyridyl, pyrimidyl, imidazolyl, pyrazolyl, triazinyl, thiazolyl, thiadiazolyl, oxadiazolyl or oxazolyl), each of which is optionally substituted by halogen, nitro, amino, $C_1$-$C_6$-alkylamino, di($C_1$-$C_6$-alkyl)amino, $C_1$-$C_6$-alkyl, $C_1$-$C_6$-haloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkylthio, $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_1$-$C_6$-alkoxyimino-$C_1$-$C_6$-alkoxycarbonylmethyl. $C(X)NR^2R^3$, (in which X represents oxygen or sulphur, $R^2$ represents hydrogen or $C_1$-$C_6$-alkyl and $R^3$ represents $C_1$-$C_6$-alkyl, $C_1$-$C_6$-haloalkyl, $C_1$-$C_6$-alkoxy, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkylthio-$C_1$-$C_6$-alkyl or phenyl-$C_1$-$C_6$-alkyl), $C_1$-$C_6$-alkylsulphinyl, $C_1$-$C_6$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_6$-alkyl or $C_1$-$C_6$-haloalkyl), phenyl (which for its part may be substituted by halogen, cyano, nitro, $C_1$-$C_6$-alkyl or $C_1$-$C_6$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl or $C_3$-$C_6$-cycloalkyl), the heteroarylalkyl radicals triazolyl-$C_1$-$C_6$-alkyl, pyridyl-$C_1$-$C_6$-alkyl, pyrimidyl-$C_1$-$C_6$-alkyl or oxadiazolyl-$C_1$-$C_6$-alkyl (which for their part may be substituted by $C_1$-$C_6$-alkyl) or represents optionally $C_1$-$C_6$-alkyl-, $C_1$-$C_6$-haloalkyl-, $C_1$-$C_6$-haloalkoxy-, dioxolanyl-, piperidinonyl-, pyrrolidinonyl- or dihydrodioxazinyl-substituted phenyl.

Very particular preference is given to novel compounds of the formula (IC-2) in which $G^1$ represents C—H, $R^1$ represents hydrogen and $G^3$ represents in each case optionally halogen-, cyano-, nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_1$-$C_4$-alkyl-$C_3$-$C_6$-cycloalkyl-, $C_1$-$C_4$-alkylcarbonyl-, $C_1$-$C_4$-alkoxycarbonyl-, aminocarbonyl-, pyridyl- or pyrimidyl-substituted oxazolinyl, dihydrooxadiazinyl, dihydrodioxazinyl or hydroxypyridyl, represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyridyl, pyrimidyl, imidazolyl, pyrazolyl, triazinyl, thiazolyl, thiadiazolyl, oxadiazolyl or oxazolyl) each of which is optionally substituted by halogen, nitro, amino, $C_1$-$C_4$-alkylamino, di($C_1$-$C_4$-alkyl)amino, $C_1$-$C_4$-alkyl, $C_1$-$C_4$-haloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkylthio, $C_1$-$C_4$-alkoxy-$C_1$-$C_4$-alkyl, bis($C_1$-$C_4$-alkoxy)-$C_1$-$C_4$-alkyl, $C_1$-$C_4$-alkoxycarbonyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, $C(X)NR^2R^3$, (in which X represents oxygen or sulphur, $R^2$ represents hydrogen or $C_1$-$C_4$-alkyl and $R^3$ represents $C_1$-$C_5$-alkyl, $C_1$-$C_4$-haloalkyl, $C_1$-$C_4$-alkoxy, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl or phenyl-$C_1$-$C_4$-alkyl), $C_1$-$C_4$-alkylsulphinyl, $C_1$-$C_4$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_4$-alkyl or $C_1$-$C_4$-haloalkyl), phenyl (which for its part may be substituted by halogen, cyano, nitro, $C_1$-$C_4$-alkyl or $C_1$-$C_4$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl), the heteroarylalkyl radicals triazolyl-$C_1$-$C_4$-alkyl, pyridyl-$C_1$-$C_4$-alkyl, pyrimidyl-$C_1$-$C_4$-alkyl or oxadiazolyl-$C_1$-$C_4$-alkyl (which for their part may be substituted by $C_1$-$C_4$-alkyl) or represents optionally $C_1$-$C_4$-alkyl-, $C_1$-$C_4$-haloalkyl-, $C_1$-$C_4$-haloalkoxy-, dioxolanyl-, piperidinonyl-, pyrrolidinonyl- or dihydrodioxazinyl-substituted phenyl.

The invention furthermore also relates to novel compounds of the formula (IC-3)

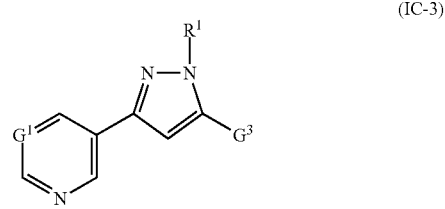

(IC-3)

in which $G^1$ represents N or C-halogen, $R^1$ represents hydrogen or alkyl (in particular methyl) and $G^3$ represents optionally substituted heterocyclyl, represents optionally substituted heteroaryl or represents optionally substituted phenyl.

Preference is given to novel compounds of the formula (IC-3) in which
$G^1$ represents N or C-halogen,
$R^1$ represents hydrogen or alkyl (in particular methyl) and
$G^3$ represents in each case optionally halogen-, cyano-, nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, alkylcycloalkyl-, alkylcarbonyl-, alkoxycarbonyl-, aminocarbonyl-, pyridyl- or pyrimidyl-substituted oxazolinyl, dihydrooxadiazinyl, dihydrodioxazinyl or hydroxypyridyl,
represents pyridyl, pyrimidyl, imidazolyl, pyrazolyl, triazinyl, thiazolyl, thiadiazolyl, oxadiazolyl or oxazolyl, each of which is optionally substituted by halogen, nitro, amino, alkylamino, dialkylamino, alkyl, haloalkyl, cycloalkylalkyl, alkoxy, haloalkoxy, alkylthio, alkoxyalkyl, bis(alkoxy)alkyl, alkoxycarbonyl, alpha-hydroxyiminoalkoxycarbonylmethyl, alpha-alkoxyiminoalkoxycarbonylmethyl, $C(X)NR^2R^3$, (in which X represents oxygen or sulphur, $R^2$ represents hydrogen or alkyl and $R^3$ represents alkyl, haloalkyl, alkoxy, cyanoalkyl, alkynyl, cycloalkyl, cycloalkylalkyl, alkoxyalkyl, alkylthioalkyl or arylalkyl), alkylsulphinyl, alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by alkyl or haloalkyl), phenyl (which for its part may be substituted by halogen, cyano, nitro, alkyl or haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl), the heteroarylalkyl radicals triazolylalkyl, pyridylalkyl, pyrimidylalkyl or oxadiazolylalkyl (which for their part may be substituted by alkyl) or
represents optionally halogen-, cyano-, alkyl-, haloalkyl-, alkoxy-, haloalkoxy-, dioxolanyl-, piperidinonyl-, pyrrolidinonyl- or dihydrodioxazinyl-substituted phenyl, Particular preference is given to novel compounds of the formula (IC-3), in which
$G^1$ represents N or C-halogen,
$R^1$ represents hydrogen or methyl and
$G^3$ represents in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl-$C_3$-$C_6$-cycloalkyl-, $C_1$-$C_6$-alkylcarbonyl-, $C_1$-$C_6$-alkoxycarbonyl-, aminocarbonyl-, pyridyl- or pyrimidyl-substituted oxazolinyl, dihydrooxadiazinyl, dihydrodioxazinyl or hydroxypyridyl,
represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyridyl, pyrimidyl, imidazolyl, pyrazolyl, triazinyl, thiazolyl, thiadiazolyl, oxadiazolyl or oxazolyl) each of which is optionally substituted by halogen, nitro, amino, $C_1$-$C_6$-alkylamino, di($C_1$-$C_6$-alkyl)amino, $C_1$-$C_6$-alkyl, $C_1$-$C_6$-haloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkylthio, $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_6$-$C_6$-alkoxyimino-$C_1$-$C_6$-alkoxycarbonylmethyl, $C(X)NR^2R^3$, (in which X represents oxygen or sulphur, $R^2$ represents hydrogen or $C_1$-$C_6$-alkyl and $R^3$ represents $C_1$-$C_6$-alkyl, $C_1$-$C_6$-haloalkyl, $C_1$-$C_6$-alkoxy, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkylthio-$C_1$-$C_6$-alkyl or phenyl-$C_1$-$C_6$-alkyl), $C_1$-$C_6$-alkylsulphinyl, $C_1$-$C_6$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_6$-alkyl or $C_1$-$C_6$-haloalkyl), phenyl (which for its part may be substituted by halogen, cyano, nitro, $C_1$-$C_6$-alkyl or $C_1$-$C_6$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl and $C_3$-$C_6$-cycloalkyl), the heteroarylalkyl radicals triazolyl-$C_1$-$C_6$-alkyl, pyridyl-$C_1$-$C_6$-alkyl, pyrimidyl-$C_1$-$C_6$-alkyl or oxadiazolyl-$C_1$-$C_6$-alkyl (which for their part may be substituted by $C_1$-$C_6$-alkyl) or
represents optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, dioxolanyl-, piperidinonyl-, pyrrolidinonyl- or dihydrodioxazinyl-substituted phenyl.

Very particular preference is given to novel compounds of the formula (IC-3) in which
$G^1$ represents N or C-halogen,
$R^1$ represents hydrogen or methyl and
$G^3$ represents in each case optionally halogen-, cyano-, nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_1$-$C_4$-alkyl-$C_3$-$C_6$-cycloalkyl-, $C_1$-$C_4$-alkylcarbonyl-, $C_1$-$C_4$-alkoxycarbonyl-, aminocarbonyl-, pyridyl- or pyrimidyl-substituted oxazolinyl, dihydrooxadiazinyl, dihydrodioxazinyl or hydroxypyridyl, represents pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyridyl, pyrimidyl, imidazolyl, pyrazolyl, triazinyl, thiazolyl, thiadiazolyl, oxadiazolyl or oxazolyl) each of which is optionally substituted by halogen, nitro, amino, $C_1$-$C_4$-alkylamino, di($C_1$-$C_4$-alkyl)amino, $C_1$-$C_4$-alkyl, $C_1$-$C_4$-haloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkylthio, $C_1$-$C_4$-alkoxy-$C_1$-$C_4$-alkyl, bis($C_1$-$C_4$-alkoxy)-$C_1$-$C_4$-alkyl, $C_1$-$C_4$-alkoxycarbonyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, C(X)NR$^2$R$^3$, (in which X represents oxygen or sulphur, R$^2$ represents hydrogen or $C_1$-$C_4$-alkyl and R$^3$ represents $C_1$-$C_5$-alkyl, $C_1$-$C_4$-haloalkyl, $C_1$-$C_4$-alkoxy, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl or phenyl-$C_1$-$C_4$-alkyl), $C_1$-$C_4$-alkylsulphinyl, $C_1$-$C_4$-alkylsulphonyl, the heterocyclyl radicals morpholinyl, triazolinonyl, dihydrodioxazinyl, dihydrooxadiazinyl, dioxolanyl, dioxanyl, piperidinonyl, pyrrolidinonyl and pyrazolinonyl (which for their part may be substituted by $C_1$-$C_4$-alkyl or $C_1$-$C_4$-haloalkyl), phenyl (which for its part may be substituted by halogen, cyano, nitro, $C_1$-$C_4$-alkyl or $C_1$-$C_4$-haloalkyl), the heteroaryl radicals pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl), the heteroarylalkyl radicals triazolyl-$C_1$-$C_4$-alkyl, pyridyl-$C_1$-$C_4$-alkyl, pyrimidyl-$C_1$-$C_4$-alkyl or oxadiazolyl-$C_1$-$C_4$-alkyl (which for their part may be substituted by $C_1$-$C_4$-alkyl) or represents optionally halogen-, cyano-, $C_1$-$C_4$-alkyl-, $C_1$-$C_4$-haloalkyl-, $C_1$-$C_4$-alkoxy, $C_1$-$C_4$-haloalkoxy-, dioxolanyl-, piperidinonyl-, pyrrolidinonyl- or dihydrodioxazinyl-substituted phenyl.

Radicals substituted by halogen (also abbreviated as "halo"), for example haloalkyl, are mono- or polysubstituted up to the maximum possible number of substituents. In the case of polyhalogenation, the halogen atoms can be identical or different. Here, halogen represents fluorine, chlorine, bromine and iodine, in particular fluorine, chlorine and bromine, with emphasis given to fluorine and chlorine.

The radical "pyrimidyl" is also referred to as "pyrimidinyl".

Preference, particular preference or very particular preference is given to using compounds carrying the substituents listed in each case as being preferred, particularly preferred or very particularly preferred.

Saturated or unsaturated hydrocarbon radicals, such as alkyl or alkenyl, can in each case be straight-chain or branched as far as is possible, including in combination with heteroatoms, such as, for example, in alkoxy.

Optionally substituted radicals can be mono- or polysubstituted, where in the case of polysubstitution the substituents can be identical or different.

The general or preferred radical definitions or illustrations listed above apply to the end products, and, correspondingly, to the starting materials and intermediates. These radical definitions can be combined with one another as desired, i.e. including combinations between the respective preferred ranges.

Preference according to the invention is given to compounds of the formula (I) which contain a combination of the meanings listed above as being preferred.

Particular preference according to the invention is given to compounds of the formula (I) which contain a combination of the meanings listed above as being particularly preferred.

Very particular preference according to the invention is given to compounds of the formula (I) which contain a combination of the meanings listed above as being very particularly preferred.

An emphasized group of compounds are the compounds of the formula (IA).

A further emphasized group of compounds are the compounds of the formula (IB-1).

A further emphasized group of compounds are the compounds of the formula (IB-2).

A further emphasized group of compounds are the compounds of the formula (IC-1).

A further emphasized group of compounds are the compounds of the formula (IC-2).

A further emphasized group of compounds are the compounds of the formula (IC-3).

In a further emphasized group of compounds of the formula (IA), G$^1$ represents CH.

In a further emphasized group of compounds of the formula (IA), G$^1$ represents N.

In a further emphasized group of compounds of the formula (IA), G$^1$ represents C-halogen.

In a further emphasized group of compounds of the formula (IB-1), G$^1$ represents N.

In a further emphasized group of compounds of the formula (IB-1), G$^1$ represents C-halogen.

In a further emphasized group of compounds of the formula (IC-3), G$^1$ represents C-halogen.

In a further emphasized group of compounds of the formula (IC-3), G$^1$ represents N.

In a further emphasized group of compounds of the formula (IA), G$^1$ represents CH and R$^1$ represents hydrogen.

In a further emphasized group of compounds of the formula (IA), G$^1$ represents N and R$^1$ represents hydrogen.

In a further emphasized group of compounds of the formula (IA), G$^1$ represents C-halogen and R$^1$ represents hydrogen.

In a further emphasized group of compounds of the formula (IB-1), G$^1$ represents N and G$^3$ represents optionally substituted heterocyclyl.

In a further emphasized group of compounds of the formula (IB-1), G$^1$ represents N and G$^3$ represents optionally substituted heteroaryl.

In a further emphasized group of compounds of the formula (IB-1), G$^1$ represents N and G$^3$ represents optionally substituted phenyl.

In a further emphasized group of compounds of the formula (IB-1), $G^1$ represents C-halogen and $G^3$ represents optionally substituted heterocyclyl.

In a further emphasized group of compounds of the formula (IB-1), $G^1$ represents C-halogen and $G^3$ represents optionally substituted heteroaryl.

In a further emphasized group of compounds of the formula (IB-1), $G^1$ represents C-halogen and $G^3$ represents optionally substituted phenyl.

Depending on the nature of the substituents, the compounds of the formulae (I), (IA), (IB) and (IC) can, if appropriate, be present as geometrical and/or as optically active isomers or corresponding isomer mixtures of varying composition. The invention relates both to the pure isomers and to the isomer mixtures.

By way of example and in a complementary manner, preparation of compounds of the formula (I) is illustrated in the formula Schemes below. Reference may also be made here to the Preparation Examples. In the schemes, the radical $G^1$ is also referred to as $G_1$.

In the formula Schemes below, the radical R may have different meanings; however, if nothing else is indicated, these meanings can be derived from the respective context.

Formula Scheme 1

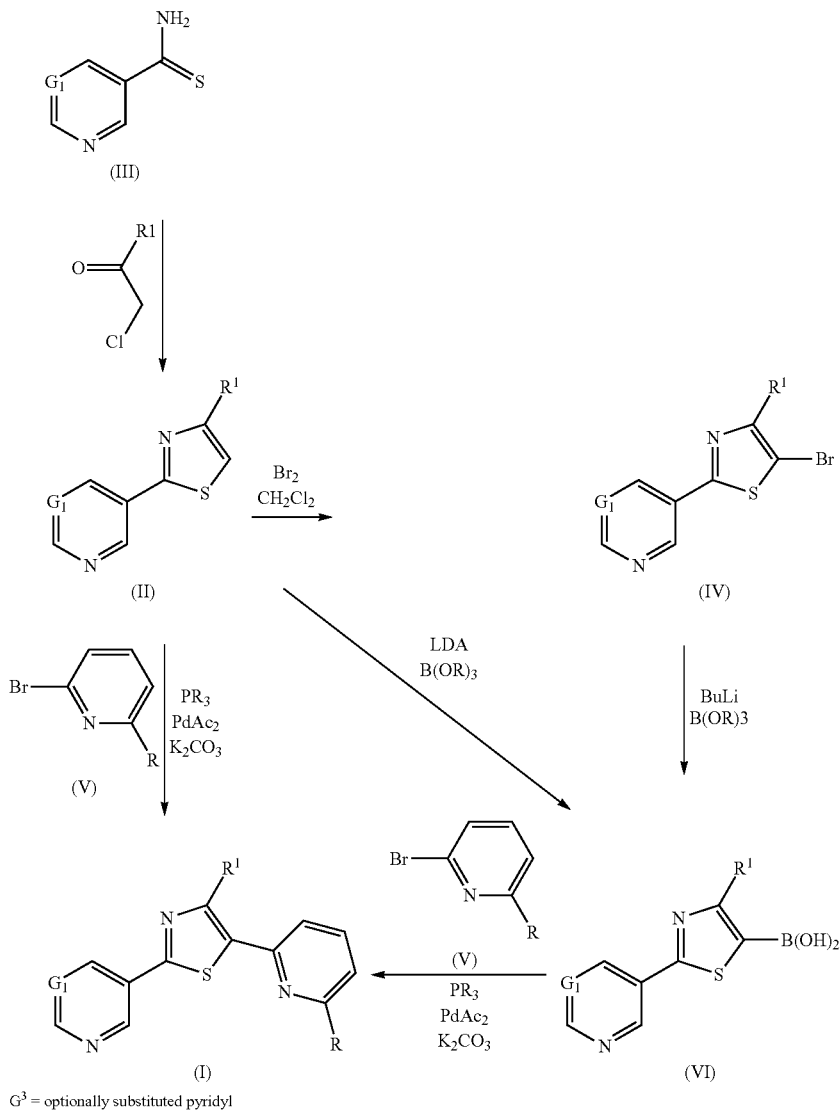

The preparation of compounds of the formula (II) where $R^1$=alkyl is carried out using methods known in principle, starting with thioamides of the formula (III) by reaction with alpha-halocarbonyl compounds; for example analogously to Helvetica Chimica Acta 1945, 820 and DE 2221647. Compounds where $R^1$ =H can be synthesized using known methods, for example analogously to Helvetica Chimica Acta 1957, 554, but preferably as described in Preparation Example 5. Compounds of the formula (IV) can be obtained from the compounds of the formula (II) by a reaction with bromine in a diluent such as dichloromethane. The boronic acids of the formula (VI) can be obtained either by deprotonation of the compounds of the formula (II) with a strong base such as LDA (lithium diisopropylamide) or by metallation of the bromides (IV), subsequent reaction with a boronic ester (R=alkyl), followed by hydrolysis. The compounds of the formula (I) according to the invention are, according to Formula Scheme 1, obtained either from the boronic acids of the formula (VI) by Suzuki reaction or directly from the thiazoles of the formula (II) by Heck reaction by transition metal-mediated coupling in the presence of complexing ligands (for example PR$_3$, R=, for example, o-tolyl) and an auxiliary base in a diluent such as, for example, palladium(II) acetate, tri-o-tolylphosphine, potassium carbonate and DMF. The bromrides of the formula (V) are known or can be obtained by methods known in principle. The preparation of the bromide of the formula (V) where R=2-pyrimidyl is described, for example, in Tetrahedron Letters, 2000, 1653; an improved preparation process results by taking into account the observations described in Tetrahedron Letters 1996, 2537, see Preparation Example 5.

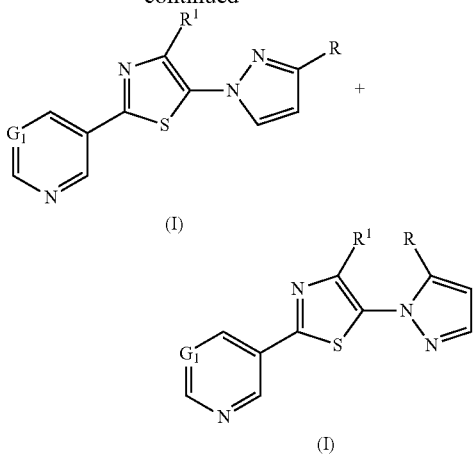

The compounds of the formula (I) according to the invention where G$^3$=N-attached pyrazole can be prepared from the bromides of the formula (IV) by transition metal-mediated reaction with pyrazoles in the presence of an auxiliary base in a diluent such as, for example, copper(I) iodide, potassium carbonate and DMF, see Journal of Organic Chemistry 2004, 5578. The appropriate pyrazoles are known or can be prepared by methods known in principle, for example analogously to Chemische Berichte, 125, 3, 1992, Chemical Communications, 24, 1994, 2751, Tetrahedron Letters, 1999, 4779.

Formula Scheme 2

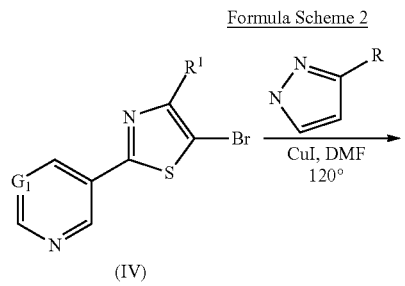

Formula Scheme 3

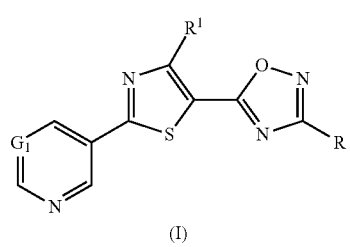
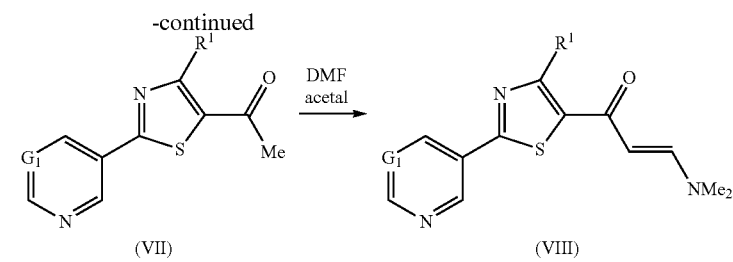

The preparation of the compounds of the formula (VII) where $R^1$=alkyl is carried out by reacting the thioamides of the formula (III) with alpha-halocarbonyl compounds to give the acetyl compounds of the formula (VII), according to DE2221647. The compounds of the formula (VII) in which $R^1$ represents hydrogen can be prepared based on the methods described in Helvetica Chimica Acta 1944, 1432-1436. The chloroformyl ester used in this reference can be prepared as described in Chemische Berichte, 1910, 3528-3533. However, preferably, the sodium salt, which can be prepared analogously to the potassium salt described in this reference, of the chloroformyl ester is used directly for the reaction with a thioamide of the formula (III), without addition of a base, giving the esters of the formula (IX). Using the standard methods indicated in Reaction Scheme 3, cf. DE 2221647, the ester of the formula (IX) can be converted initially into the acid of the formula (X) and then into the acid chloride of the formula (XI). Further reaction with O,N-dimethylhydroxylamine in a diluent such as, for example, dichloromethane or tetrahydrofuran and in the presence of a base such as, for example, triethylamine or diisopropylethylamine gives compounds of the formula (XII) which can be converted, by reaction with a methyl metal compound, such as methylmagnesium bromide, into the ketone of the formula (VII). By reacting the compounds of the formula (VII) with dimethylformamide dimethyl acetal, the enaminones of the formula (VIII) are obtained, see Heterocycles, 43, 1, 1996, 221 and Journal of Heterocyclic Chemistry 24, 1987, 837, see also Preparation Example 1. By reaction with a hydroxyamidine in the presence of an auxiliary base such as triethylamine in a diluent such as dioxane, the oxadiazoles of the formula (I) according to the invention can be obtained from the acid chloride of the formula (XI).

Formula Scheme 4

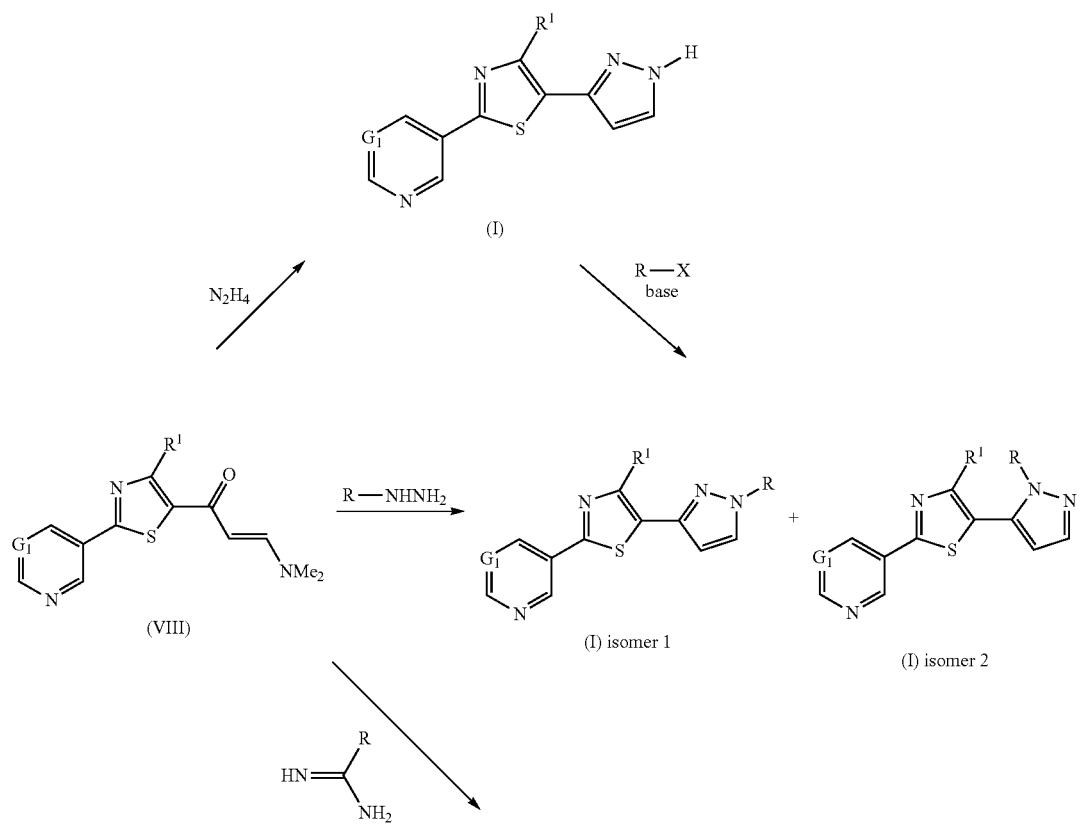

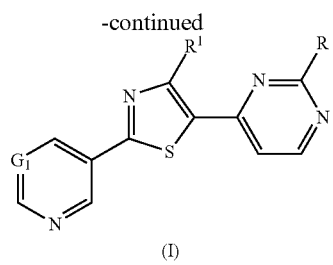

(I)

By reaction with hydrazine hydrate in a diluent such as ethanol, the enaminones of the formula (VIII) give the NH-pyrazoles of the formula (I). By reaction with an alkylating or (het-)arylating agent and an auxiliary base such as sodium hydride in a diluent such as DMF, these pyrazoles can be converted into the N-substituted pyrazoles of the formula (I) according to the invention. By reacting the enaminones of the formula (VIII) with substituted hydrazines, it is likewise possible to obtain the N-substituted pyrazoles of the formula (I). The substituted hydrazines required are known or can be prepared by methods known in principle, see, for example, Journal of Medicinal Chemistry 2005, 141. The N-substituted pyrazoles of the formula (I) according to the invention are formed in the isomeric forms isomer 1 and isomer 2, the preferred route to isomer 1 being via the NH-pyrazoles of the formula (I). By reacting the enaminones of the formula (VIII) in the presence of an auxiliary base such as sodium ethoxide in a diluent such as ethanol with amidines, the pyrimidines of the formula (I) according to the invention can be obtained of theory required amidines are known or can be prepared by methods known in principle, see also Preparation Example 1.

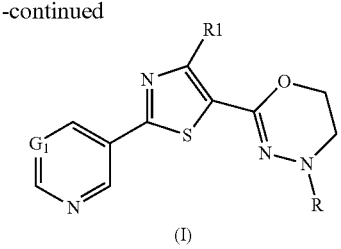

(I)

According to Formula Scheme 5 (see also Preparation Example 7), the compounds of the formula (I) according to the invention are obtained by initially reacting 2-hydrazinoethanol with an alkylating or (het-)arylating agent R—X to give compounds of the formula (XIV); a reaction of this type is described in Khim. Geterosikl. Soedin 1990, 8, 1065. From these compounds, it is possible to obtain, with acids of the formula (X) and with the aid of an activating agent such as BOP-Cl in the presence of an auxiliary base such as triethylamine in a diluent such as DMF, the hydrazides of the formula (XV) which, for example by a Mitsunobu reaction, as described in Heterocycles 37, 3, 1994, 1645, can be converted into the compounds of the formula (I) according to the invention.

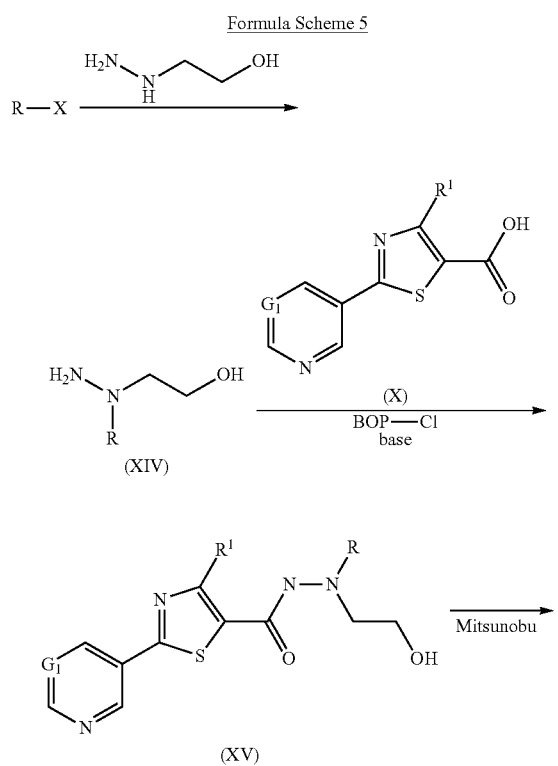

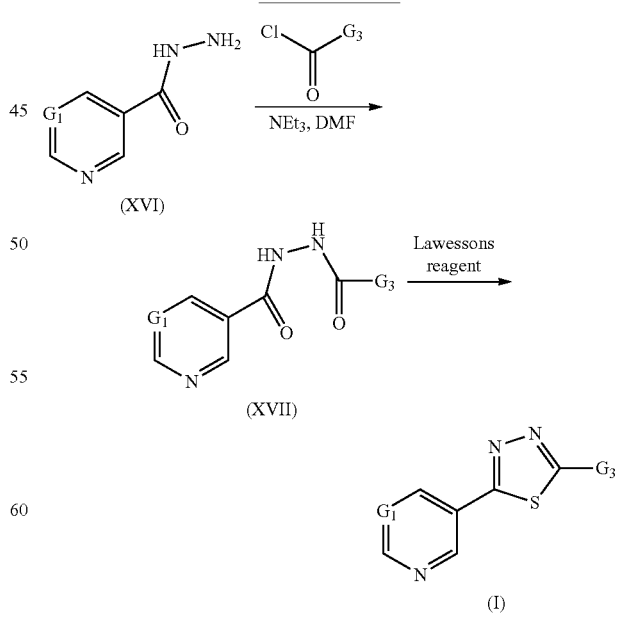

The thiadiazoles of the formula (I) according to the invention according to Formula Scheme 6 are obtained by reacting nicotinic acid hydrazides of the formula (XVI) with, for example, carbonyl chlorides to give compounds of the formula (XVII), followed by cyclization in the presence of a sulphurizing agent such as Lawessons reagent without diluent (cf. Youji Huaxue (2004), 24(5), 502) or in a diluent such as toluene or anisole. Hydrazides of the formula (XVI) have been described, for example in Journal of Medicinal Chemistry, 32, 3, 1989, 583-593, and can be obtained by hydrazinolysis of the corresponding carboxylic esters.

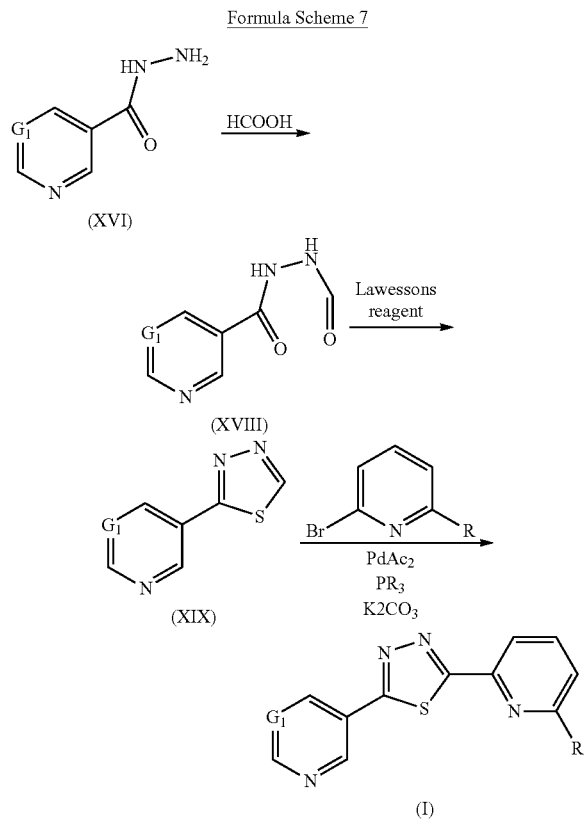

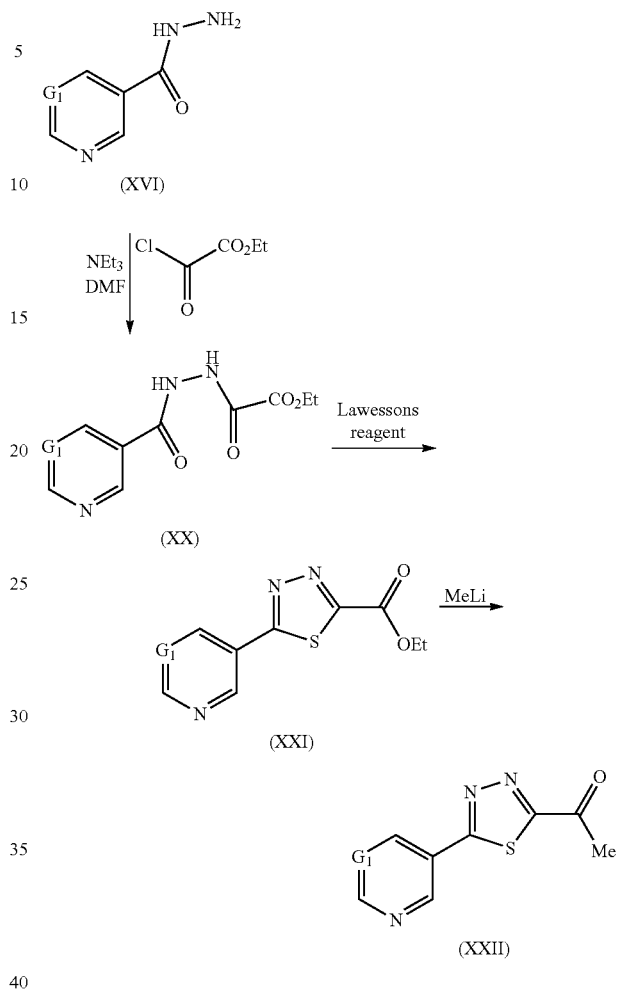

Alternatively to the process described in Formula Scheme 6, thiadiazoles of the formula (I) according to the invention can also be obtained by a Heck reaction analogously to the process described in Formula Scheme (I), see Preparation Example 10. The required thiadiazoles of the formula (XIX) can be obtained from nicotinic acid hydrazides of the formula (XVI) by reaction with formic acid analogously to Bull. Soc. Chim. Belg. Vol. 106, No 2, 1997, 109, giving the formylhydrazides of the formula (XVIII), and subsequent reaction with a sulphurizing agent such as Lawessons reagent in a diluent such as toluene or anisole, see Journal of Indian Chemistry 8, 1970, 509.

Formula Scheme 8 describes the preparation of ketones of the formula (XXII), see also Preparation Example 9. The hydrazide of the formula (XVI) is converted in the presence of a base such as, for example, triethylamine in a diluent such as, for example, dimethylformamide (DMF) with ethyl oxalyl chloride into the diacylhydrazine compound of the formula (XX), which then reacts with a sulphurizing agent such as, for example, Lawessons reagent to give the thiadiazole of the formula (XXI), see Liquid Crystals Today, Volume 14, 1, 2005, 15-18. By reaction with a metal methyl compound such as methyl lithium, the ketone (XXII) can be obtained from the ester (XXI), see Journal of Organic Chemistry 1997, 4774.

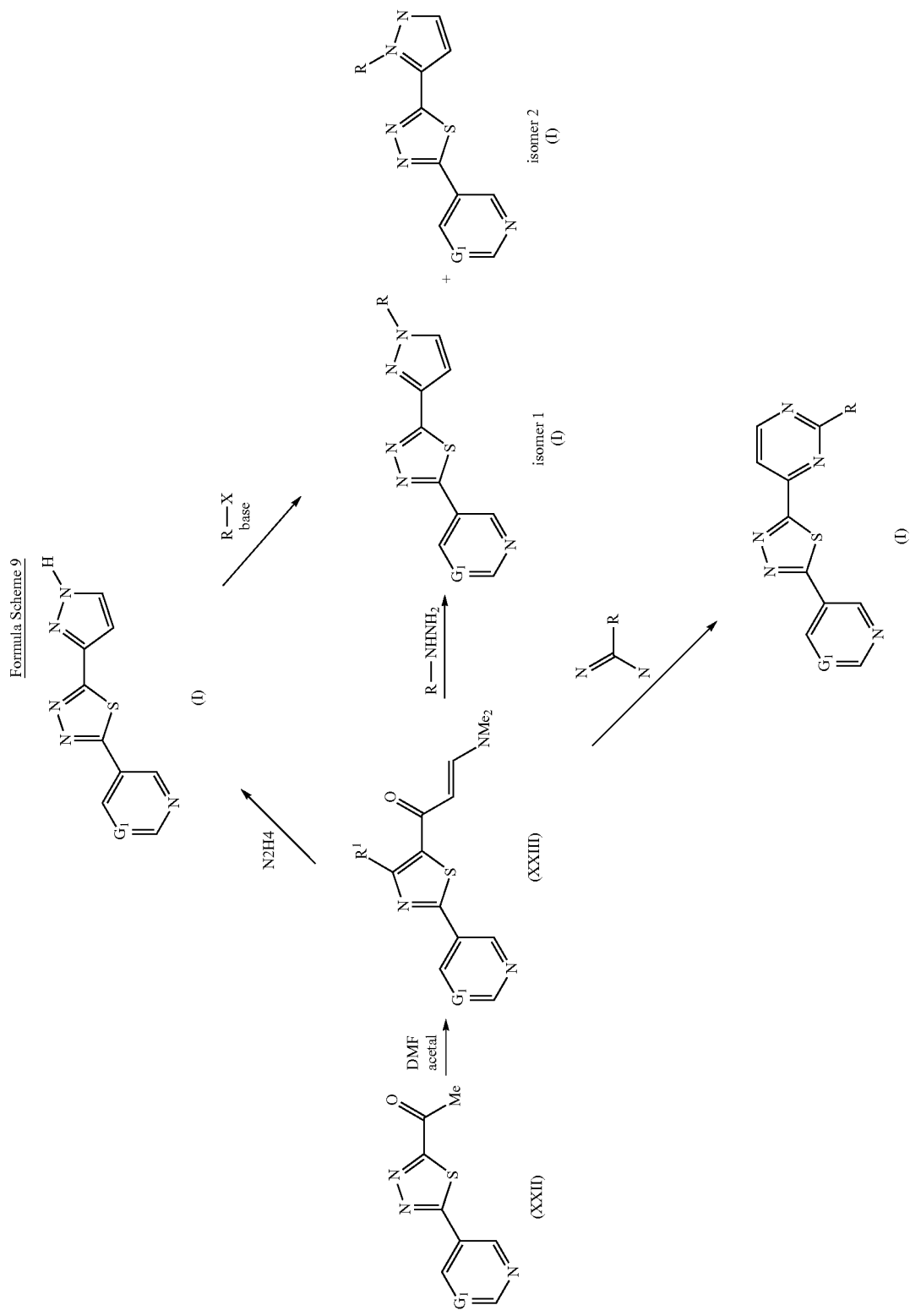

For Formula Scheme 9, see also Preparation Example 9. By reacting the ketone of the formula (XXII) with DMF acetal, the enaminones of the formula (XXIII) are obtained analogously to Formula Scheme 3. According to the process described in Formula Scheme 4, the enaminone of the formula (XXIII) gives either, by reaction with hydrazine hydrate, the NH-pyrazoles of the formula (I) which can be converted further into the N-substituted pyrazoles of the formula (I), or directly the N-substituted pyrazoles of the formula (I) by reaction with substituted hydrazine. The compounds of the formula (I) are formed in the isomeric forms isomer 1 and isomer 2, the preferred route to isomer 1 being via NH-pyrazoles of the formula (I). By reacting the enaminone of the formula (XXIII) with amidines, it is possible to obtain the pyrimidines of the formula (I) according to the invention.

For Formula Scheme 10, see also Synthesis Example 11. The acetyl compound of the formula (XXV) gives, by reaction with oxalic ester in the presence of a base such as sodium ethoxide in a diluent such as toluene or ethanol (cf. Journal of the American Chemical Society 1948, 4265), the ester of the formula (XXVI), by reaction with hydrazines, this is converted into the pyrazole of the formula (XXVII). For this and the reaction steps that follow, see also Preparation Example 11. The pyrazole of the formula (XXVII) is formed in the isomeric forms isomer 1 and isomer 2. From the isomer 1 of the pyrazole of the formula (XXVII), the acid of the formula (XXVIII) is prepared using an alkali metal hydroxide such as sodium hydroxide in a diluent such as ethanol/water. In accordance with the process described in Formula Scheme 3, this affords the amide of the formula (XXIX) and the ketone of the formula (XXX).

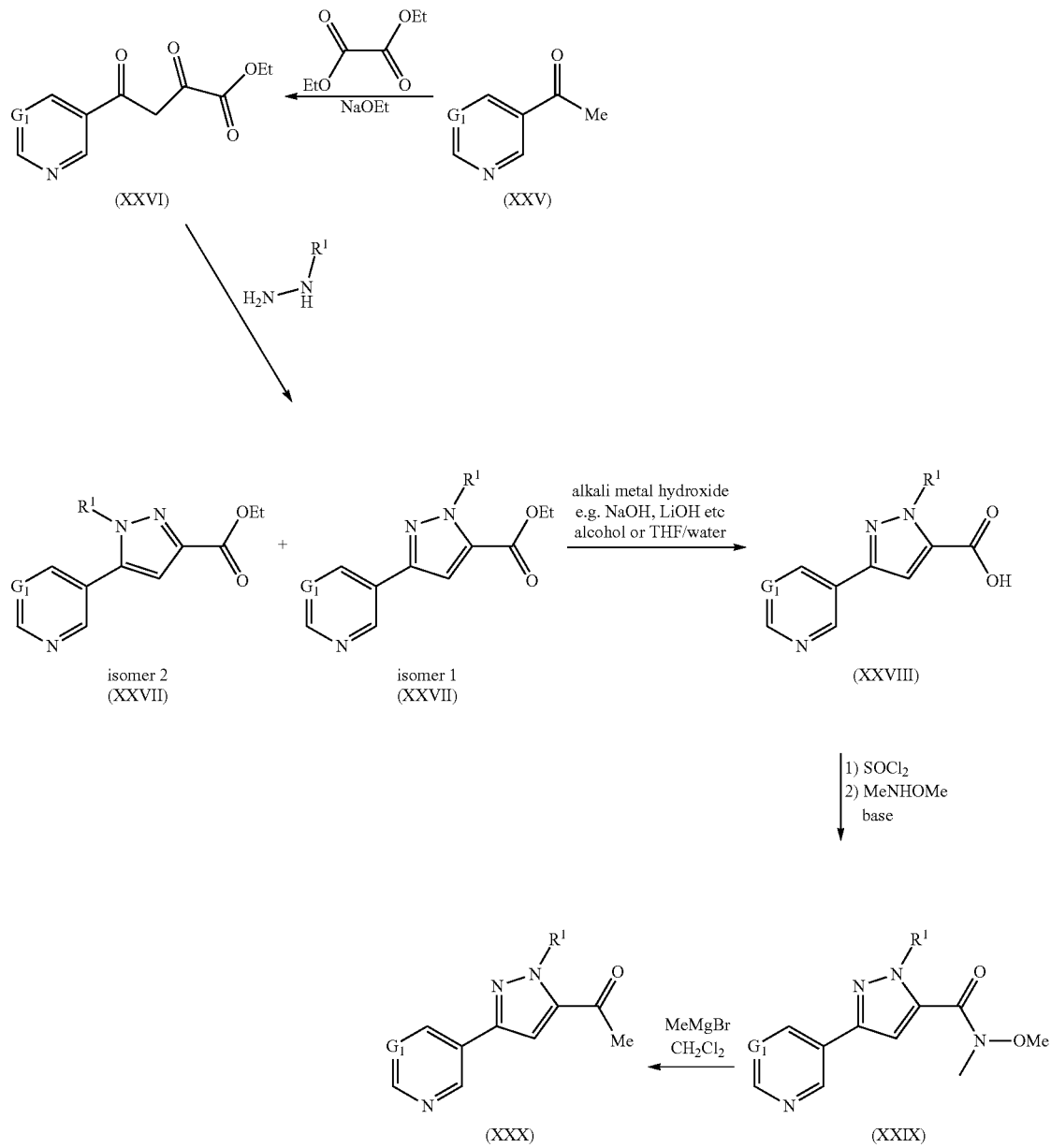

Formula Scheme 10

Formula Scheme 11

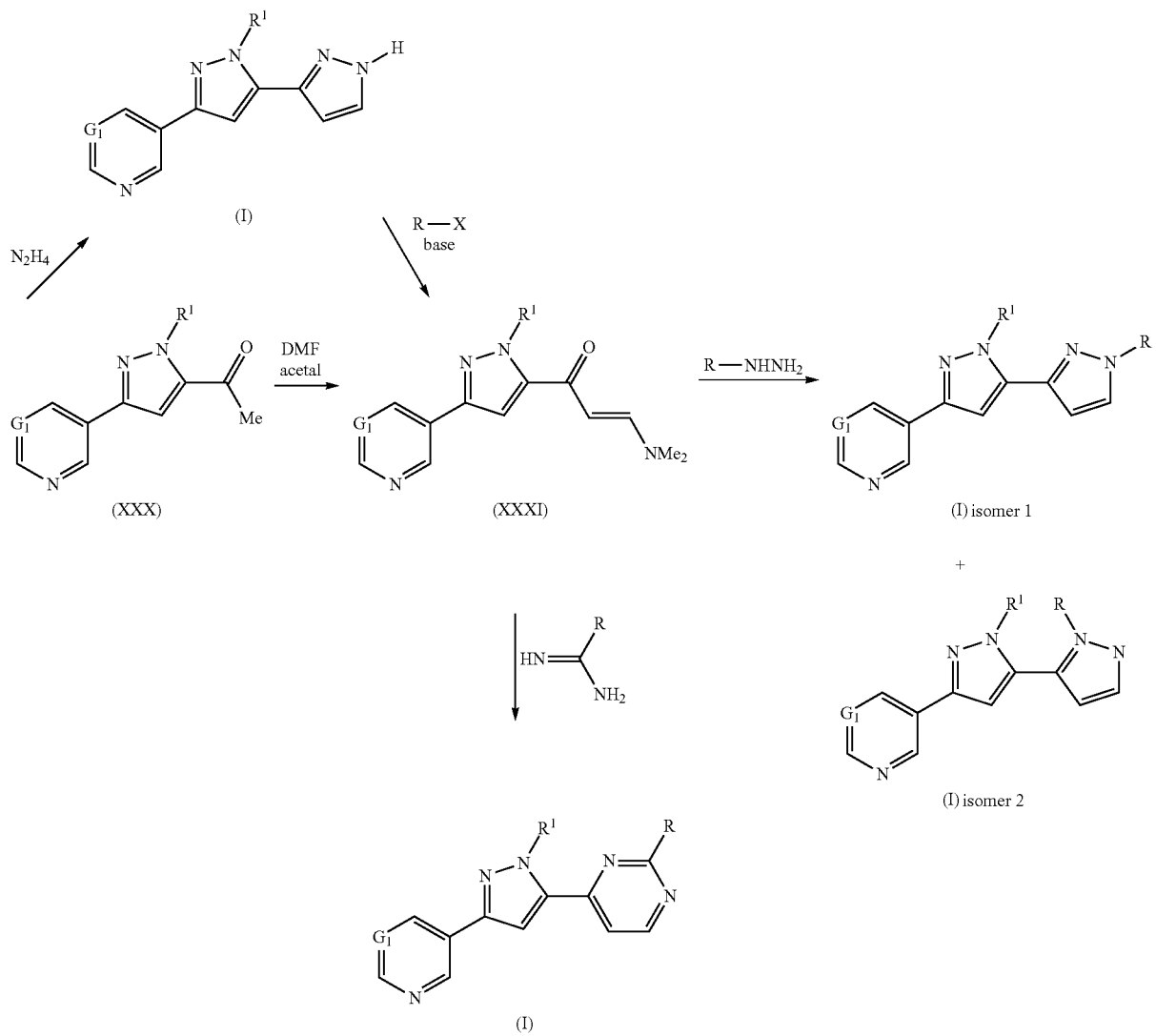

For Formula Scheme 11, see also Preparation Example 11. The preparation of the compounds of the formula (I) according to the invention corresponds to the process described in Formula Schemes 3 and 4. By reacting the ketone of the formula (XXX) with DMF acetal, the enaminone of the formula (XXXI) is obtained. From these compounds, the pyrimidines of the formula (I) according to the invention can be obtained by reaction with amidines. By reaction with hydrazine, the NH-pyrazole of the formula (I) is obtained, and from this compound the N-substituted pyrazole of the formula (I) which is formed in the isomeric forms isomer 1 and isomer 2. The preferred route to the N-substituted pyrazoles of the formula (I) according to the invention is via the N-pyrazole of the formula (I).

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni*, Aculops spp., Aculus spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., Epitrimerus pyri, Eutetranychus spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora*, Polyphagotarsonemus latus, *Psoroptes* spp., *Rhipicephalus* spp., *Rhizoglyphus* spp., *Sarcoptes* spp.,

*Scorpio maurus*, Stenotarsonemus spp., *Tarsonemus* spp., *Tetranychus* spp., *Vasates lycopersici*.

From the class of the Bivalva, for example, Dreissena spp.

From the order of the Chilopoda, for example, *Geophilus* spp., *Scutigera* spp.

From the order of the Coleoptera, for example, *Acanthoscelides obtectus*, Adoretus spp., *Agelastica alni*, *Agriotes* spp., *Amphimallon solstitialis*, *Anobium punctatum*, *Anoplophora* spp., *Anthonomus* spp., *Anthrenus* spp., *Apogonia* spp., *Atomaria* spp., *Attagenus* spp., *Bruchidius obtectus*, *Bruchus* spp., *Ceuthorhynchus* spp., *Cleonus mendicus*, *Conoderus* spp., *Cosmopolites* spp., *Costelytra zealandica*, *Curculio* spp., *Cryptorhynchus lapathi*, *Dermestes* spp., *Diabrotica* spp., *Epilachna* spp., Faustinus cubae, *Gibbium psylloides*, Heteronychus arator, *Hylamorpha elegans*, *Hylotrupes bajulus*, *Hypera postica*, *Hypothenemus* spp., Lachnosterna consanguinea, *Leptinotarsa dece mlineata*, *Lissorhoptrus oryzophilus*, *Lixus* spp., *Lyctus* spp., *Meligethes aeneus*, *Melolontha melolontha*, Migdolus spp., *Monochamus* spp., *Naupactus xanthographus*, *Niptus hololeucus*, *Oryctes rhinoceros*, *Oryzaephilus surinamensis*, *Otiorrhynchus sulcatus*, *Oxycetonia jucunda*, *Phaedon cochleariae*, *Phyllophaga* spp., *Popillia japonica*, *Premnotrypes* spp., *Psylliodes chrysocephala*, *Ptinus* spp., *Rhizobius ventralis*, *Rhizopertha dominica*, *Sitophilus* spp., *Sphenophorus* spp., *Sternechus* spp., *Symphyletes* spp., *Tenebrio molitor*, *Tribolium* spp., *Trogo-derma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., Loa Loa, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Strongyloides* spp., *Taenia saginata*, *Taenia soliurn*, *Trichinella spiralis*, *Trichinella nativa*, *Trichinella* britovi, *Trichinella nelsoni*, *Trichinella pseudopsiralis*, *Trichostrongulus* spp., *Trichuris trichuria*, *Wuchereria bancrofti*.

It is furthermore possible to control protozoa, such as Eimeria.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, Miridae, *Nezara* spp., *Oebalus* spp., Pentomidae, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus*spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp.,

*Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella inmmaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Anguina* spp., *Aphelenchoides* spp., *Belonoaimnus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose, natural and synthetic polymers in the form of powders, granules or lattices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergistic agent added to be active itself.

When used as insecticides, the active compounds according to the invention can furthermore be present in their commercially available formulations and in the use forms, prepared from these formulations, as mixtures with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treateof theorye terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula (I) and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp. (*Ctenocephalides canis*, *Ctenocephalides felis*), *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis*, *Periplaneta americana*, *Blattela germanica*, *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal application, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of from 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus*, *Chlorophorus pilosis*, *Anobium punctatum*, *Xestobium rufovillosum*, *Ptilinus pecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthes rugicollis*, *Xyleborus* spec. *Tryptodendron* spec. *Apate monachus*, *Bostrychus capucins*, *Heterobostrychus brunneus*, *Sinoxylon* spec. Dinoderus minutus;

Hymenopterons, such as Sirex juvencus, Urocerus gigas, Urocerus gigas taignus, Urocerus augur;

Termites, such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis*, *Coptotermes formosanus*;

Bristletails, such as *Lepisma saccharina*.

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins a d the like. They can be employed alone or in combination with other active compounds and auxiliaries in domestic insecticide products for controlling these pests. They are active against sensitive and resistant species and against all developmental stages. These pests include:

From the order of the Scorpionidea, for example, Buthus occitanus.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides* forinae.

From the order of the Araneae, for example, Aviculariidae, Araneidae.

From the order of the Opiliones, for example, Pseudoscorpiones chelifer, Pseudoscorpiones cheiridium, Opiliones phalangium.

From the order of the Isopoda, for example, Oniscus asellus, Porcellio scaber.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae,*
*Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola* bisselliella.

From the order of the Siphonaptera, for example, *Ctenocephalides canis, Ctenocephalides felis, Pulex irritans, Tunga penetrans, Xenopsylla* cheopis.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus* humanus capitis, *Pediculus* humanus corporis, *Pemphigus* spp., *Phylloera vastatrix, Phthirus pubis*.

From the order of the Heteroptera, for example, *Cimex* hemipterus, *Cimex* lectularius, Rhodinus prolixus, *Triatoma* infestans.

In the field of domestic insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for scattering or in bait stations.

PREPARATION EXAMPLES

Example 1

Step 1: 3-(5-Acetyl-4-methylthiazol-2-yl)pyridinium chloride

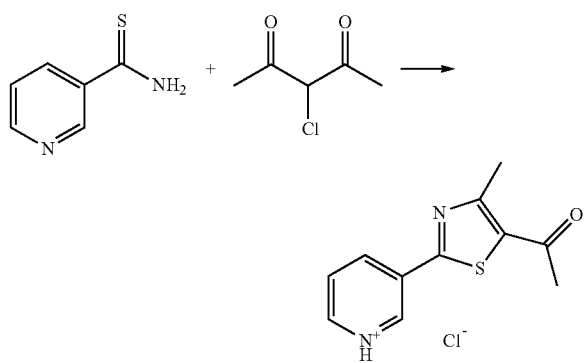

Using an overhead stirrer, 65 g (470.3 mmol) of thionicotinamide and 140 ml (1174.6 mmol) of chloroacetylacetone in 0.5 l of ethanol were heated under reflux for 8 h.

After cooling, the precipitate formed was filtered off with suction, washed with diethyl ether and dried in a rotary evaporator.

Yield: 109.2 g (91% of theory), logP (HCOOH) 1.48

1H-NMR (D6-DMSO): 2.6 (s, 3H), 2.75 (s, 3H), 7.65 (dd, 1H), 8.45 (d, 1H), 8.75 (d, 1H), 9.2 (s, 1H)

Step 2:
1-(4-Methyl-2-pyridin-3-ylthiazol-5-yl)ethanone

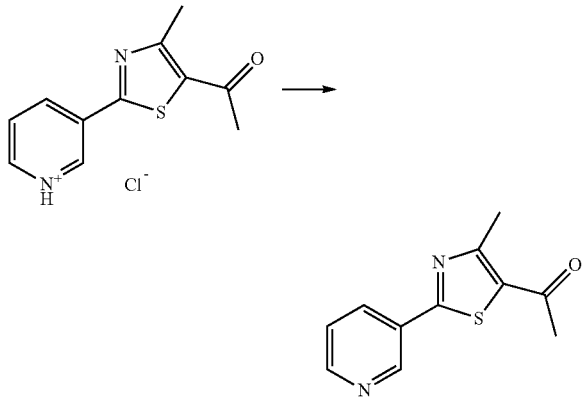

With stirring, 109.2 g (428.6 mmol) of 3-(5-acetyl-4-methylthiazol-2-yl)pyridinium chloride were dissolved in about 0.5 l of water, and 70 ml (936.7 mmol) of 25% aq. ammonia were added slowly. An oil separated off and solidified after some time of stirring. Stirring was continued in an ice bath for 10 min, the mixture was filtered off with suction and the precipitate was washed with dilute aq. ammonia and dried.

Yield 97.51 g (104% of theory), logP (HCOOH) 1.5

1H-NMR (D6-DMSO) 2.6 (s, 3H), 2.75 (s, 3H), 7.55 (dd, 1H), 8.3 (d, 1H), 8.7 (d, 1H), 9.15 (s, 1H)

Step 3: 3-Dimethylamino-1-(4-methyl-2-pyridin-3-ylthiazol-5-yl)propenone

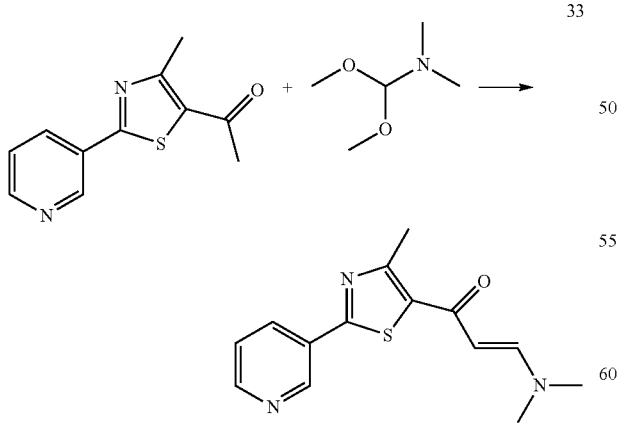

On a very short distillation bridge, 33.53 g (153.6 mmol) of 1-(4-methyl-2-pyridin-3-ylthiazol-5-yl)ethanone and 35 ml (261.4 mmol) of DMF-DMA were stirred at 95° C. for 1 h, during which time some distillate passed over. The residue was concentrated by evaporation and crystallized on cooling. It was recrystallized from benzotrifluoride.

Yield: 30.52 g (69% of theory), logP (HCOOH) 1.35

1H-NMR (D6-DMSO): 2.65 (s, 3H), 3.2 (s, 6H), 5.45 (d, 1H), 7.5 (dd, 1H), 7.65 (d, 1H), 8.25 (d, 1H), 8.65 (d, 1H), 9.1 (s, 1H)

Step 4: Pyrimidine-2-carboxamidine hydrochloride

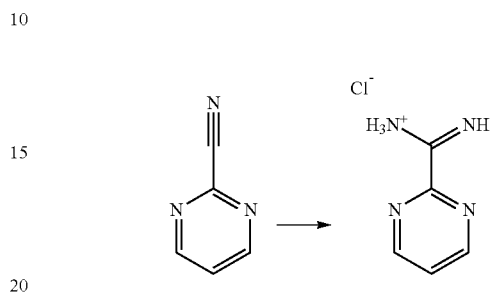

2.8 ml (15 mmol) of a 30% strength solution of sodium methoxide in methanol were added to 15.76 g (150 mmol) of 2-pyridinecarbonitrile in 80 ml of methanol. After 2 days, 8 g (150 mmol) of ammonium chloride were added, and stirring was continued for another day. The mixture was filtered, the filtrate was concentrated by evaporation and the residue was triturated with 80 ml of diethyl ether, filtered off with suction and dried.

Yield: 20.2 g (84% of theory)

1H-NMR (D6-DMSO): 7.9 (t, 1H), 9.1 (d, 2H), 9.7 (br, 4H)

Step 5: 4-(4-Methyl-2-pyridin-3-ylthiazol-5-yl)-[2,2']bipyrimidinyl

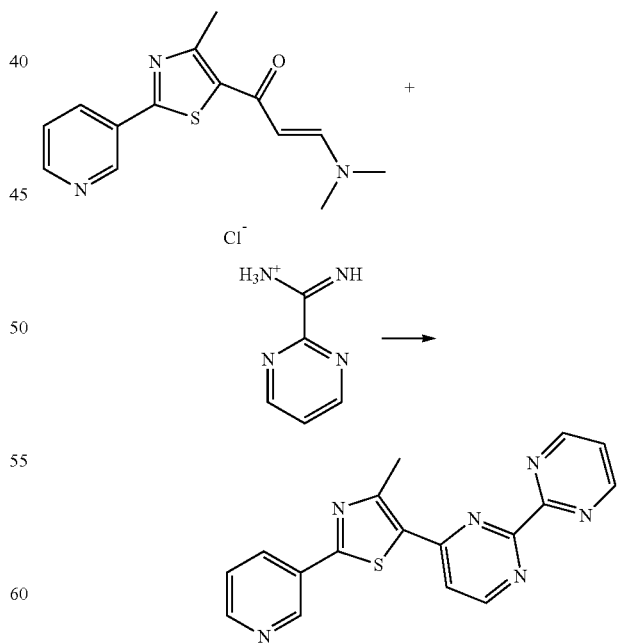

20.04 g (7.46 mmol) of 3-dimethylamino-1-(4-methyl-2-pyridin-3-ylthiazol-5-yl)propenone, 1.22 g (7.69 mmol) of pyrimidine-2-carboxamidine hydrochloride and 3 ml (7.96 mmol) of a 21% strength solution of sodium ethoxide in ethanol in 20 ml of ethanol were heated under reflux for 16 h. The mixture was concentrated by evaporation, aq. citric acid, aq. sodium chloride and dilute aqueous sodium hydroxide solution were added to pH=12, the mixture was extracted 4 times with chloroform/isopropanol and the combined organic phases were dried with sodium sulphate and concentrated by evaporation. The residue was purified by recrystallization from benzotrifluoride which involved brief heating to boiling point with activated carbon and hot filtration.

Yield: 1.91 g (75% of theory), logP (HCOOH) 1.17

1H-NMR (D6-DMSO): 2.75 (s, 3H), 7.55 (m, 1H), 7.65 (m, 1H), 7.95 (d, 1H), 8.75 (m, 1H), 8.7 (m, 1H), 9.15 (m, 3H), 9.2 (s, 1H)

Example 2

Step 1: 3-[4-Methyl-5-(1H-pyrazol-3-yl)thiazol-2-yl]pyridine

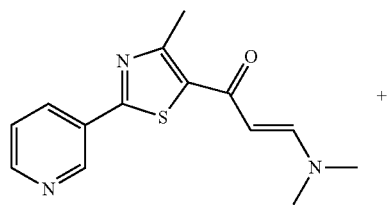

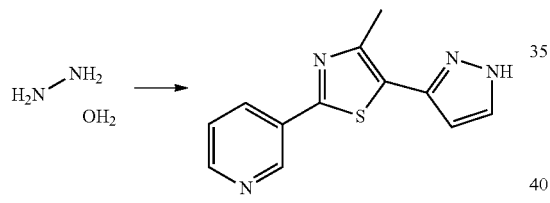

5.04 g (18.4 mmol) of 3-dimethylamino-1-(4-methyl-2-pyridin-3-ylthiazol-5-yl)propenone in 80 ml of ethanol and 2 ml (41.1 mmol) of hydrazine hydrate were heated under reflux for 0.5 h. The mixture was concentrated by evaporation and the residue was recrystallized from dioxane.

Yield: 3.75 g (83% of theory), logP (HCOOH) 1.31

1H-NMR (D6-DMSO): 2.6 (s, 3H), 6.6 (s, 1H), 7.5 (dd, 1H), 7.8 (s, 1H), 8.25 (d, 1H), 8.65 (m, 1H), 9.1 (s, 1H), 13 (s, 1H)

Step 2: 2-[3-(4-Methyl-2-pyridin-3-ylthiazol-5-yl)pyrazol-1-yl]pyrazine

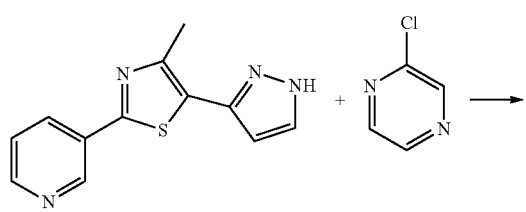

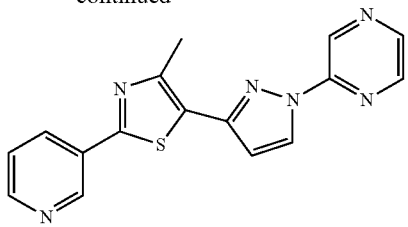

0.5 ml of 15-crown-5 and about 0.5 g of sodium hydride were added to 0.85 g (3.5 mmol) of 3-[4-methyl-5-(1H-pyrazol-3-yl)thiazol-2-yl]pyridine and 1.2 g (10.4 mmol) of 2-chloropyrazine in 50 ml of DMF, the mixture was stirred at 75° C. for 1.5 h, dilute phosphoric acid was added after cooling and the mixture was concentrated by evaporation. Aq. sodium chloride, ethyl acetate and dilute aqueous sodium hydroxide solution to pH=7 were added to the residue, and the mixture was extracted three times with ethyl acetate and two more times with isopropanol. The combined organic phases were dried with MgSO₄ and concentrated by evaporation, and the residue was recrystallized from dioxane, which involved hot filtration.

Yield: 0.87 g (77% of theory), logP (HCOOH) 2.3

1H-NMR (D6-DMSO): 2.7 (s, 3H), 7 (s, 1H), 7.55 (dd, 1H), 8.3 (d, 1H), 8.6 (m, 1H), 8.65 (m, 2H), 8.7 (m, 1H), 9.15 (m, 1H), 9.2 (s, 1H)

Example 3

Step 1: 3-(5-Bromo-4-methylthiazol-2-yl)pyridine

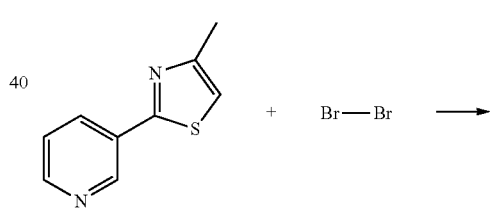

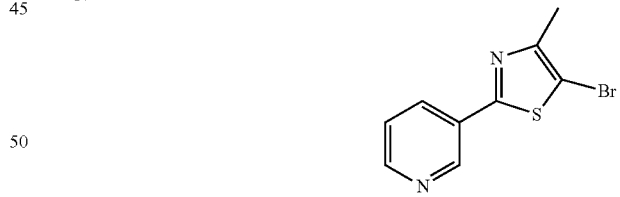

With ice bath cooling, 15 ml (292 mmol) of bromine were added to 16.8 g (95.5 mmol) of 3-(4-methylthiazol-2-yl)pyridine in 200 ml of dichloromethane. The precipitate was filtered off with suction, washed with dichloromethane and suspended in water, and aqueous potassium carbonate, dilute aqueous sodium hydroxide solution, aqueous sodium bisulphite and MTBE (methyl tert-butyl ether) were then added and the mixture was extracted three times with MTBE. The combined organic phases were dried with sodium sulphate and concentrated by evaporation.

Yield 17.35 g (71% of theory), logP (HCOOH) 2.3

1H-NMR (CD3CN) 2.45 (s, 3H), 7.45 (dd, 1H), 8.15 (d, 1H), 8.75 (d, 1H), 9 (s, 1H)

Step 2: 3-Dimethylamino-1-pyrimidin-2-ylpropenone

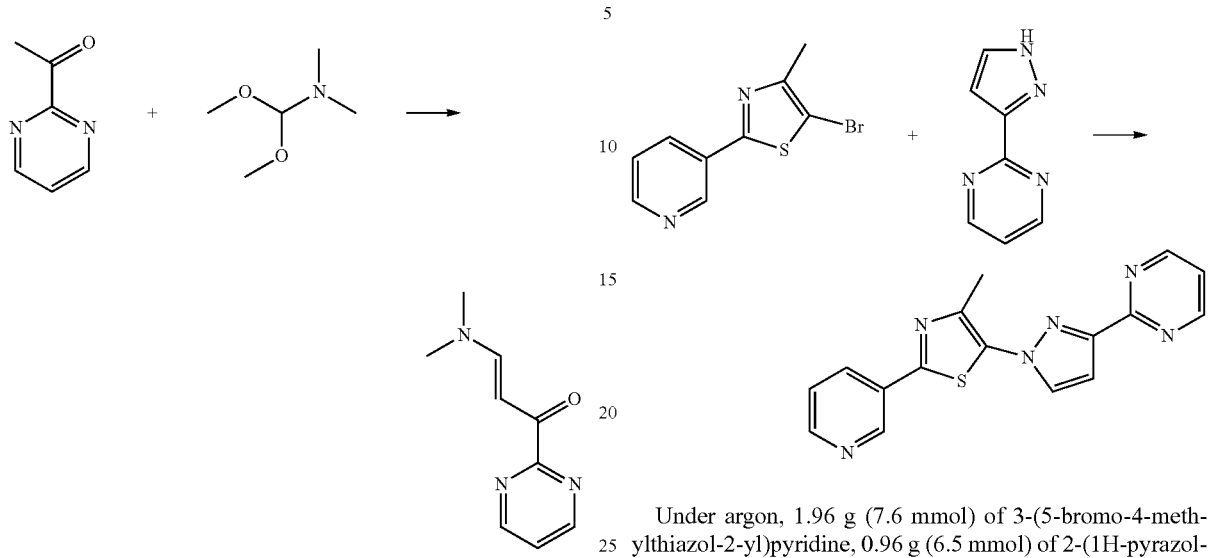

On a very short distillation bridge, 11 g (90 mmol) of 2-acetylpyrimidine and 23 g (193 mmol) of DMF-DMA were stirred at 100° C. for 1 h, during which time some distillate passed over. The mixture was concentrated by evaporation and the residue was recrystallized from benzotrifluoride.

Yield: 11.4 g (70% of theory)

1H-NMR (D6-DMSO): 3.1 (s, 6H), 6 (d, 1H), 7.5 (t, 1H), 7.7 (d, 1H), 8.9 (d, 2H)

Step 3: 2-(1H-Pyrazol-3-yl)pyrimidine

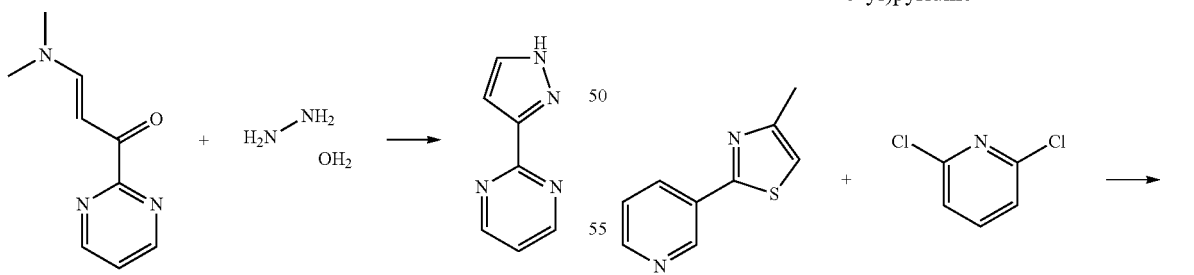

11.2 g (63.2 mmol) of 3-dimethylamino-1-pyrimidin-2-ylpropenone and 4.5 ml (92.5 mmol) of hydrazine hydrate in 200 ml of EtOH were heated under reflux for 2 h. The mixture was concentrated by evaporation and the residue was recrystallized from benzotrifluoride.

Yield: 8.72 g (94% of theory), logP (HCOOH) 0.1,

1H-NMR (D6-DMSO) 9.65 (s, 1H), 7.4 (s, 1H), 7.6-7.8 (br, 1H), 8.85 (m, 2H), 13-13.5 (br, 1H)

Step 4: 2-[1-(4-Methyl-2-pyridin-3-ylthiazol-5-yl)-1H-pyrazol-3-yl]pyrimidine Under argon, 1.96 g (7.6 mmol) of 3-(5-bromo-4-methylthiazol-2-yl)pyridine, 0.96 g (6.5 mmol) of 2-(1H-pyrazol-3-yl)pyrimidine, 0.15 g (0.78 mmol) of copper(I) iodide, 0.15 g (1 mmol) of 8-hydroxyquinoline and 3 g (21 mmol) of potassium carbonate were stirred in 20 ml of DMF and a few drops of water at 120° C. for 16 h. The mixture was concentrated by evaporation, aq. citric acid, aq. sodium chloride, phosphate buffer solution, Na EDTA and ethyl acetate were added to pH=6 and the mixture was extracted 4 times with ethyl acetate. The combined organic phases were dried with sodium sulphate and concentrated by evaporation. The residue was purified by chromatography on silica gel (cyclohexane/acetone) and then on RP-18 silica gel (water/acetonitrile).

Yield: 0.06 g (2% of theory), logP (HCOOH) 1.48,

1H-NMR (CD3CN): 2.5 (s, 3H), 7.15 (d, 1H), 7.3 (t, 1H), 7.45 (dd, 1H), 8 (d, 1H), 8.2 (d, 1H), 8.75 (m, 1H), 8.8 (d, 2H), 9.7 (s, 1H)

Example 4

Step 1: 2-Chloro-6-(4-methyl-2-pyridin-3-ylthiazol-5-yl)pyridine

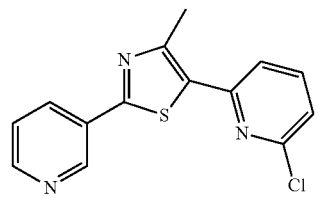

Under argon, 45 mg (0.2 mmol) of palladium(II) acetate were dissolved in 10 ml of DMF, and 2 ml (0.7 mmol) of a 10% strength solution of tri-tert-butyl phosphane in hexane were added. The hexane was removed from the mixture under reduced pressure, 2 g (13.6 mmol) of 2,6-dichloropyridine and 1.98 g (11.2 mmol) of 3-(4-methylthiazol-2-yl)pyridine and about 1 g of tetrabutylammonium bromide as a solution in DMF and 3.1 g (22.5 mmol) of potassium carbonate were added and the mixture was stirred at 135° C. for 1 h. The mixture was concentrated by evaporation, ethyl acetate, aq. citric acid, dilute aqueous sodium hydroxide solution to pH=9 and aq. sodium chloride were added to the residue and the mixture was extracted three times with ethyl acetate. The combined organic phases were dried with sodium sulphate and concentrated by evaporation, and the residue was purified by chromatography on silica gel (cyclohexane/acetone).

Yield: 0.93 g (22% of theory), logP (HCOOH) 2.66

1H-NMR (D6-DMSO) 2.7 (s, 3H), 7045 (d, 1H), 7.55 (m, 1H) 7.75 (d, 1H), 7.95 (t, 1H), 8.3 (d, 1H), 8.65 (m 1H), 9.15 (s, 1H)

Step 2: 6-(4-Methyl-2-pyridin-3-ylthiazol-5-yl)pyridine-2-carbonitrile

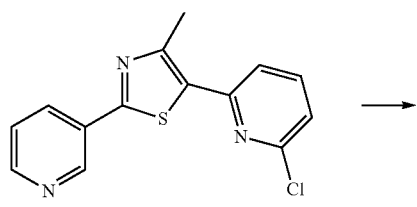

Under argon, 0.5 g (3 mmol) of palladium(II) chloride in 25 ml of DMF and 1.6 g (6.1 mmol) of triphenylphosphane were stirred at 100° C. for 10 min, a mixture of 7.5 g (15.3 mmol) of 2-chloro-6-(4-methyl-2-pyridin-3-ylthiazol-5-yl)pyridine and 33.8 g (91 mmol) of potassium hexacyanoferrate(II) was added, and the mixture was stirred at 125° C. for 16 h; undissolved material was then filtered off with suction, the filtrate was concentrated by evaporation, the residue was dissolved in ethyl acetate/water, once more undissolved material was removed by filtration with suction, the aqueous phase was extracted three times with ethyl acetate and the combined organic phases were dried with sodium sulphate and concentrated by evaporation. The residue was purified by chromatography on silica gel (cyclohexane/acetone).

Yield: 1.6 g (35% of theory), logP (HCOOH) 2.11

1H-NMR (D6-DMSO) 2.7 (s, 3H), 7.35 (m, 1H), 7.5 (m, 1H), 7.75 (m, 1H), 7.9 (m, 1H), 8.3 (m, 1H), 8.65 (m, 1H), 9.15 (s, 1H)

Step 3: 6-(4-Methyl-2-pyridin-3-ylthiazol-5-yl)pyridine-2-carbothioamide

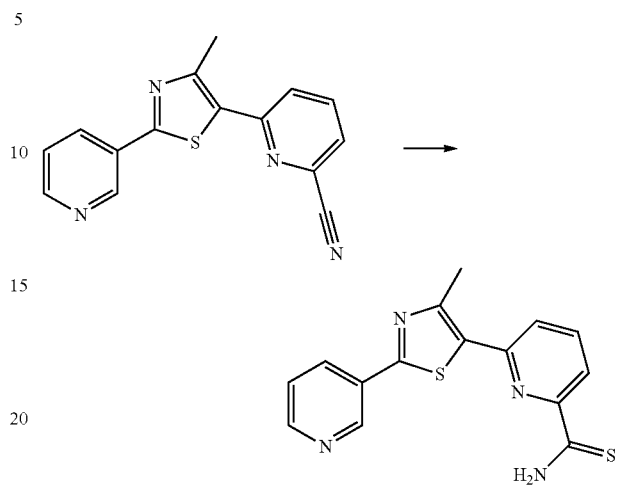

0.36 g (1.3 mmol) of 6-(4-methyl-2-pyridin-3-ylthiazol-5-yl)pyridine-2-carbonitrile in 5 ml of pyridine and 0.2 ml of triethylamine and 0.24 ml (1.4 mmol) of a 40% strength aqueous solution of ammonium sulphide were stirred at 50° C. for 3 h, the mixture was then concentrated by evaporation and stirred with 5 ml of ice-water, and the precipitate was filtered off with suction, dried, extracted with boiling ethyl acetate and, after cooling, filtered off with suction and dried.

Yield: 0.22 g (51% of theory), logP (HCOOH) 2.13

1H-NMR (D6-DMSO): 2.7 (s, 3H), 7.55 (m, 1H), 7.95 (m, 1H), 8.1 (m, 1H), 8.35 (m, 1H); 8.4 (d, 1H), 8.7 (m, 1H), 9.15 (m, 1H), 9.5 (br, 1H), 10.5 (s, 1H)

Step 4: 3-[6-(4-Methyl-2-pyridin-3-ylthiazol-5-yl)pyridin-2-yl]-[1,2,4]triazine

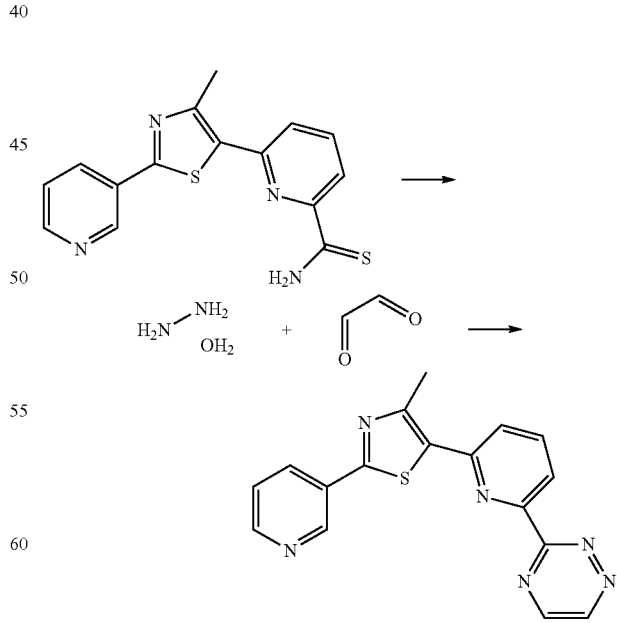

0.23 g (0.7 mmol) of 6-(4-methyl-2-pyridin-3-ylthiazol-5-yl)pyridine-2-carbothioamide in 65 ml of warm ethanol and 0.15 ml (2.9 mmol) of hydrazine hydrate were stirred at reflux for 1.5 h, 0.3 ml of a 40% strength aqueous solution of glyoxal was then added and the mixture was heated under reflux for another 15 minutes. The mixture was concentrated by evaporation and the residue was purified by chromatography on RP-18 silica gel (water/acetonitrile).

Yield: 0.043 g (17% of theory), logP (HCOOH) 1.58

1H-NMR (D6-DMSO): 2.8 (s, 3H), 7.55 (m, 1H), 8.05 (d, 1H), 8.2 (t, 1H), 8.4 (m, 2H), 8.7 (d, 1H), 9.1 (m, 1H), 9.2 (m, 1H), 9.55 (m, 1H)

Example 5

Step 1: 3-Thiazol-2-ylpyridine

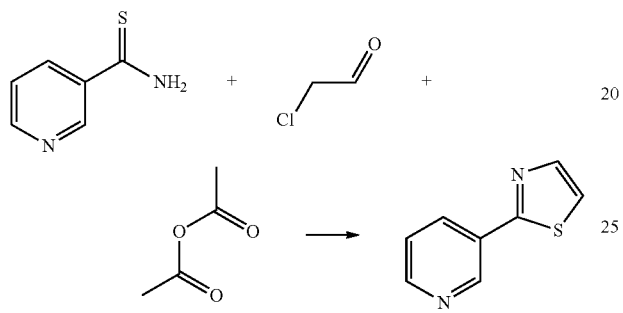

31.4 g (227 mmol) of thionicotinamide were dissolved in 150 ml of acetic acid, and 28 ml (238 mmol) of chloroacetaldehyde 55% in water and 110 ml (1171 mmol) of acetic anhydride were added. The mixture was stirred at 70° C. for about 16 h, and the cooled mixture was poured into ice/aqueous ammonia, saturated with NaCl and stirred for 3 h. Insoluble material was decanted off, and the mixture was filtered with glass wool and extracted 4 times with methyl tert-butyl ether. The combined organic phases were dried with MgSO$_4$ and concentrated by evaporation. The residue was subjected to a kugelrohr distillation under reduced pressure.

Yield (calculated proportionally for two batches) 17 g (46% of theory), logP (HCOOH) 0.62

1H-NMR (CD3CN): 7.45 (m, 1H), 7.55 (m1, H), 7.9 (m, 1H), 8.25 (m, 1H), 8.6 (m, 1H), 9.15 (m, 1H)

Step 2: 2-(6-Bromopyridin-2-yl)pyrimidine

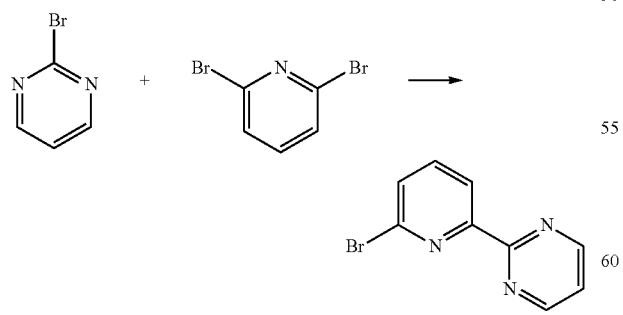

Under argon, 54.5 ml (137.1 mmol) of a 2.5 molar solution of N-BuLi in 70 ml of THF were diluted with 70 ml of THF. At <−70° C., 32.5 g (137.1 mmol) of 2,6-dibromopyridine dissolved in 150 ml of THF were added dropwise. The mixture was stirred for 15 min and, still at <−70° C., 19.2 ml (107 mmol) of a 5.6-molar solution of zinc chloride in diethyl ether were then added. The mixture was allowed to thaw, a solution of 17.4 g (109 mmol) of bromopyrimidine in 50 ml of THF and a suspension of 3.9 g (3.4 mmol) of tetrakis(triphenylphosphine)palladium in 50 ml of THF were added. The mixture was boiled at reflux for 4 h and, after cooling, Na EDTA in water and dilute aqueous sodium hydroxide solution to pH=10 were added. The mixture was filtered off with suction to remove undissolved material, the aqueous phase was extracted three times with ethyl acetate and the combined organic phases were dried with MgSO$_4$ and concentrated by evaporation. The residue was recrystallized from 60 ml of benzotrifluoride which involved brief heating to boiling point with activated carbon and hot filtration.

Yield: 14.82 g (52% of theory), logP (HCOOH) 1.3

1H-NMR (CD3CN): 7.4 (t, 1H), 7.65 (d, 1H), 7.8 (dd, 1H), 8.4 (d, 1H), 8.9 (m, 2H)

Step 3: 2-[6-(2-Pyridin-3-ylthiazol-5-yl)pyridin-2-yl]pyrimidine

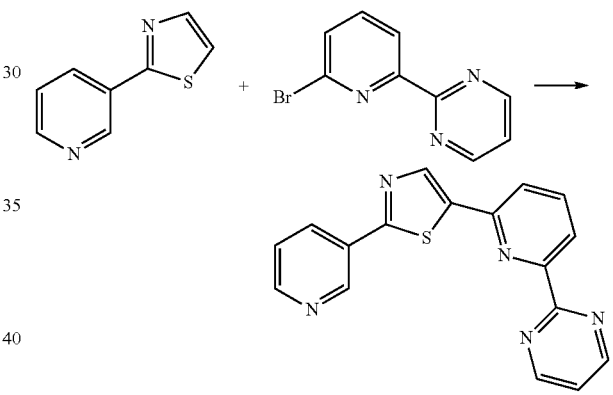

Under argon, 0.53 g (3 mmol) of palladium(II) chloride and 1.88 g (6 mmol) of tri-o-tolylphosphine and 1.87 g of tetrabutylammonium chloride were stirred with 55 ml of DMF at 95° C. for 5 min, 9.73 g (60 mmol) of 3-thiazol-2-ylpyridine and 12.74 g (54 mmol) of 2-(6-bromopyridin-2-yl)pyrimidine as a solution in DMF and 16.28 g (116 mmol) of potassium carbonate were then added and the mixture was stirred at 130° C. for 4 h. The mixture was concentrated by evaporation, ethyl acetate, aq. sodium chloride, aq. citric acid and dilute aqueous sodium hydroxide solution to pH=10 were added, the mixture was stirred with chloroform/isopropanol 10%, insoluble material was filtered off with suction, the aqueous phase was extracted two more times with chloroform/isopropanol 10% and the combined organic phases were dried with sodium sulphate and concentrated by evaporation. The residue was purified by chromatography on silica gel (cyclohexane/acetone). The product obtained can be purified further by recrystallization from benzotrifluoride/dioxane.

Yield: 9 g (44% of theory), logP (HCOOH) 1.53

1H-NMR (D6-DMSO) 7.55 (m, 2H), 8.1 (m, 1H), 8.15 (m, 1H), 8.3 (m, 1H), 8.35 (m, 1H), 8.7 (m, 2H), 9.0 (d 2H), 9.2 (s, 1H)

Example 6

2-[6-(4-Methyl-2-pyridin-3-ylthiazol-5-yl)pyridin-2-yl]pyrimidine

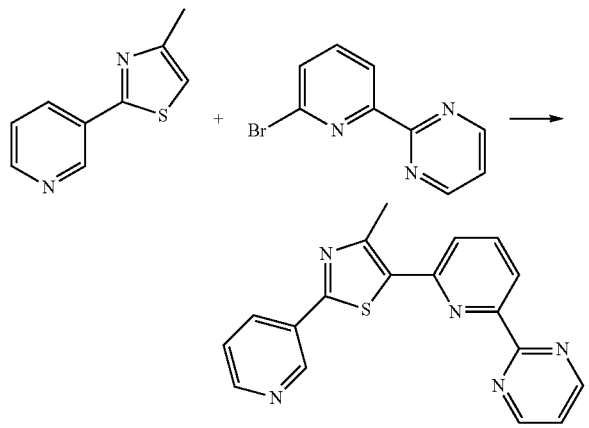

Under argon, 13 mg (0.059 mmol) of palladium acetate were dissolved in 5 ml of DMF, and 0.6 ml (0.23 mmol) of a 10% strength solution of tri-tert-butylphosphane in hexane was added. The hexane was evaporated under reduced pressure, 0.26 g (1.45 mmol) of 3-(4-methylthiazol-2-yl) pyridine, 0.38 g (1.62 mmol) of 2-(6-bromopyridin-2-yl) pyrimidine, 0.4 g (2.92 mmol) of potassium carbonate and about 0.5 g of tetrabutylammonium chloride were added and the resulting mixture was stirred under argon at 130° C. for 48 h. The mixture was then concentrated by evaporation and dissolved in ethyl acetate, aq. NaCl, aq. citric acid and dilute aqueous sodium hydroxide solution to pH=8. The mixture was extracted 3 times with ethyl acetate, the combined organic phases were dried with sodium sulphate and concentrated by evaporation and the residue was purified by chromatography on silica gel (cyclohexane/acetone). For further purification, the substance was recrystallized from benzotrifluoride.

Yield: 0.175 g (35% of theory), logP (HCOOH) 1.75

1H-NMR (CD3CN): 2.75 (s, 3H), 7.45 (m, 2H), 7.4 (m, 1H), 8.0 (m, 1H), 8.3 (m, 2H), 8.6 (m, 1H), 8.9 (m, 2H), 9.2 (m, 1H)

Example 7

Step 1: 2-(N-Pyrimidin-2-ylhydrazino)ethanol

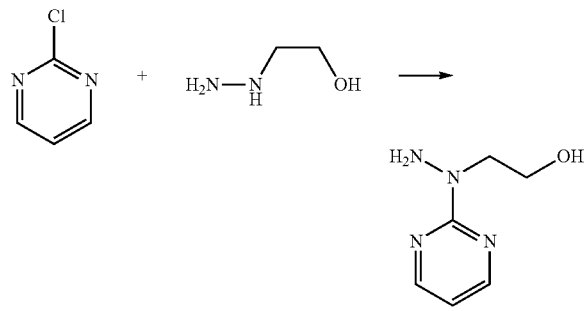

4.8 g (41.9 mmol) of 2-chloropyrimidine in 100 ml of ethanol and 3.6 g (47 mmol) of hydrazinoethanol and 9 g (64.2 mmol) of potassium carbonate were heated under reflux for 5 h. The mixture was filtered off with suction and the filtrate was concentrated by evaporation.

Yield: 5.98 g (87% of theory)

1H-NMR (D6-DMSO) 3.65 (m, 2H), 3.75 (t, 2H), 4.35 (br, 1H), 4.65 (br, 2H), 6.55 (t, 1H), 8.3 (d, 2H)

Step 2: 4-Methyl-2-pyridin-3-ylthiazole-5-carboxylic acid N-(hydroxyethyl)-N-pyrimidin-2-ylhydrazide

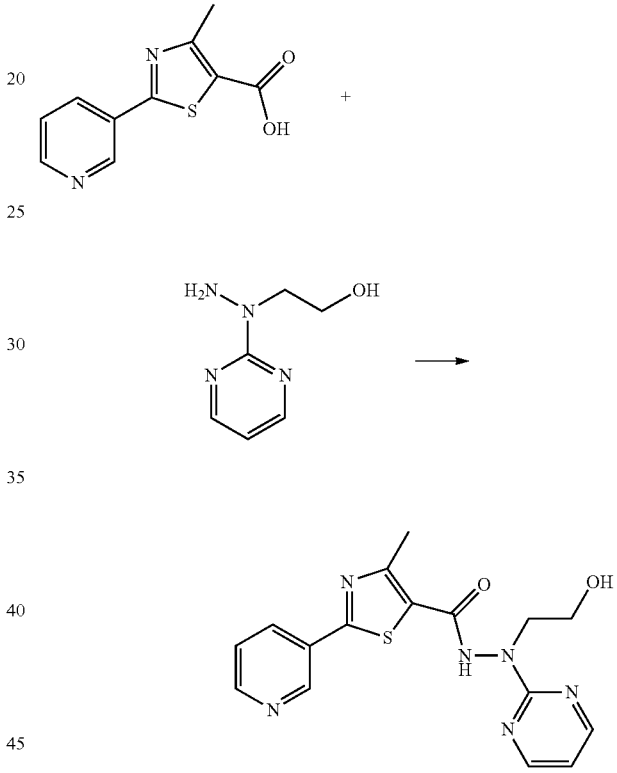

0.8 g (3.7 mmol) of 4-methyl-2-pyridin-3-ylthiazole-5-carboxylic acid was dissolved in 150 ml of DMF/acetonitrile, and 6 ml of triethylamine and 0.4 ml (4 mmol) of ethyl chloroformate were added. The mixture was stirred for 10 min, 0.6 g (4 mmol) of 2-(N-pyrimidin-2-ylhydrazino)ethanol was added, and the mixture was stirred for 20 min and concentrated by evaporation. Ethyl acetate, aq. citric acid, dilute aqueous sodium hydroxide solution to pH=8 and aq. sodium chloride were added to the residue, the mixture was extracted three times with ethyl acetate and the combined organic phases were dried with sodium sulphate and concentrated by evaporation. The residue was purified by chromatography on silica gel (cyclohexane/acetone).

Yield: 0.42 g (31% of theory), logP (HCOOH) 1.08

1H-NMR (D6-DMSO) 2.7 (s, 3H), 3.7 (m, 2H), 3.95 (m, 2H), 4.45 (m, 1H), 6.8 (m, 1H), 7.55 (m, 1H), 8.35 (d, 1H), 8.45 (d, 2H), 8.7 (m, 1H), 9.15 (s, 1H), 10.5 (s, 1H)

Step 3: 2-(4-Methyl-2-pyridin-3-ylthiazol-5-yl)-4-pyrimidin-2-yl-5,6-dihydro-4H-[1,3,4]oxadiazine

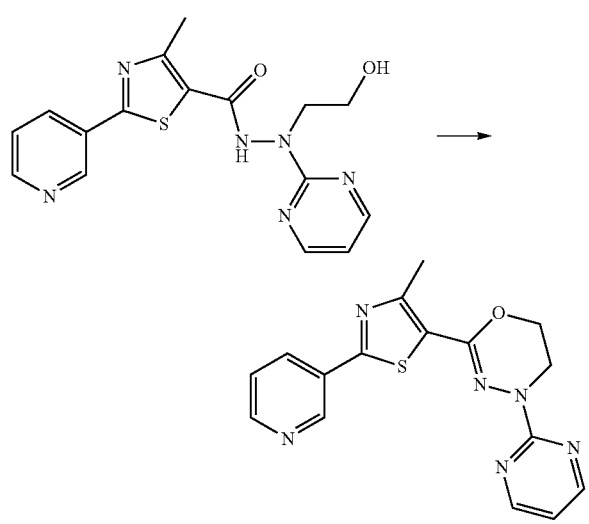

0.46 g (1.3 mmol) of 4-methyl-2-pyridin-3-ylthiazole-5-carboxylic acid N'-(hydroxyethyl)-N'-pyrimidin-2-ylhydrazide and 0.4 g (1.5 mmol) of triphenylphosphane and 0.3 ml of DIAD were stirred in 5 ml of acetonitrile for 16 h, and the mixture was then concentrated by evaporation and the residue was chromatographed on silica gel (cyclohexane/acetone).

Yield: 0.1 g (23% of theory), logP (HCOOH) 1.56

1H-NMR (D6-DMSO) 2.7 (s, 3H), 4.2 (t, 2H), 4.6 (t, 2H), 6.9 (t, 1H), 7.5 (dd, 1H), 8.3 (d, 1H), 8.55 (d, 2H), 8.65 (m, 1H), 9.1 (s, 1H)

Example 8

Step 1: 6-Bromopyridine-2-carboxylic acid hydroxyamide

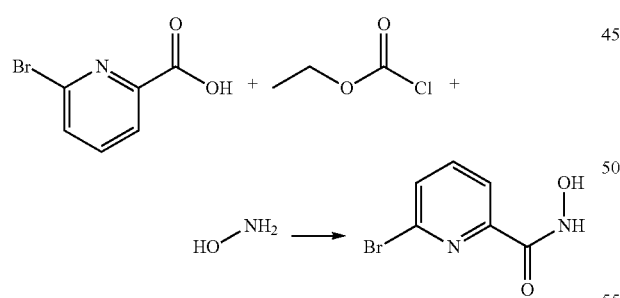

40 ml of triethylamine and then, with ice bath cooling, 6 ml (63 mmol) of ethyl chloroformate and, after 10 min of stirring, 6 ml (101 mmol) of an aqueous 50% strength solution of hydroxylamine were added to 10.2 g (50.5 mmol) of bromopicolinic acid. The mixture was stirred at room temperature for 1 h and evaporated, aq. citric acid and ethyl acetate were added to the residue and the mixture was extracted repeatedly with ethyl acetate. The combined organic phases were dried with sodium sulphate and concentrated by evaporation.

Yield: 11.8 g (22% pure) logP (HCOOH) 0.69

Step 2: 3-(6-Bromopyridin-2-yl)-5,6-dihydro-[1,4,2]dioxazine

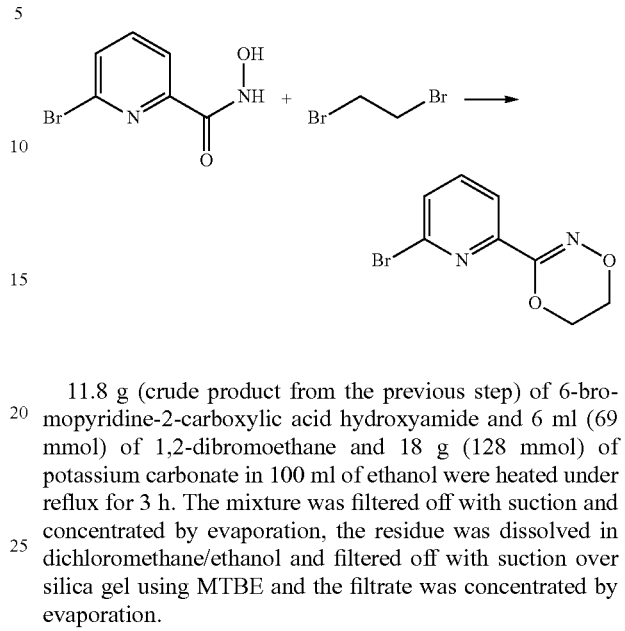

11.8 g (crude product from the previous step) of 6-bromopyridine-2-carboxylic acid hydroxyamide and 6 ml (69 mmol) of 1,2-dibromoethane and 18 g (128 mmol) of potassium carbonate in 100 ml of ethanol were heated under reflux for 3 h. The mixture was filtered off with suction and concentrated by evaporation, the residue was dissolved in dichloromethane/ethanol and filtered off with suction over silica gel using MTBE and the filtrate was concentrated by evaporation.

Yield: 3.03 g logP (HCOOH) 1.37

1H-NMR (CD3CN) 4.15 (m, 2H), 1.45 (m, 2H), 7.6 (d, 1H), 7.7 (t, 1H), 7.8 (d, 1H)

Step 3: 3-[6-(4-Methyl-2-pyridin-3-ylthiazol-5-yl)pyridin-2-yl]-5,6-dihydro-[1,4,2]dioxazine

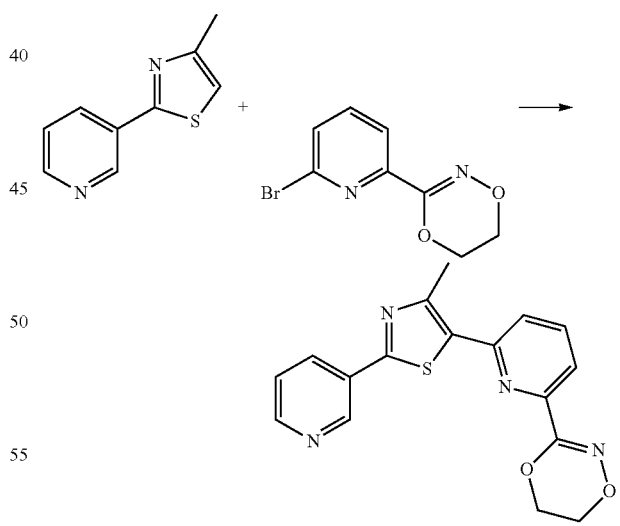

Under argon, 23 mg (0.1 mmol) of palladium(II) acetate were dissolved in 15 ml of DMF, 0.25 ml (0.25 mmol) of a 1 molar solution of tri-tert-butylphosphane was added, followed by 0.18 g (1 mmol) of 3-(4-methylthiazol-2-yl)pyridine, 0.24 g (1 mmol) of 3-(6-bromopyridin-2-yl)-5,6-dihydro-[1,4,2]dioxazine, 0.2 g of tetrabutylammonium chloride as a solution in DMF and 1 ml of a 2 molar solution of potassium carbonate in water, and the mixture was stirred at 130° C. for 5 h. The mixture was concentrated by evaporation, ethyl acetate, dilute aqueous sodium hydroxide solution, aq. citric acid to pH=7 and aq. sodium chloride were added to the residue, the mixture was extracted three times with ethyl acetate and the combined organic phases were dried with sodium sulphate and concentrated by evaporation. The residue was purified by chromatography on silica gel (cyclohexane/acetone).

Yield: 0.06 g (17% of theory), logP (HCOOH) 1.81

1H-NMR (CD3CN): 2.75 (s, 3H), 4.2 (dd, 2H), 4.55 (dd, 2H), 7.45 (m, 1H), 7.8 (m, 2H), 7.9 (t, 1H), 8.3 (d, 1H), 8.65 (m, 1H), 9.2 (s, 1H)

Further compounds according to the invention were prepared analogously (see Table).

Example 9

Step 1: Ethyl oxo-[N'-(pyridin-3-carbonyl)hydrazino]acetate

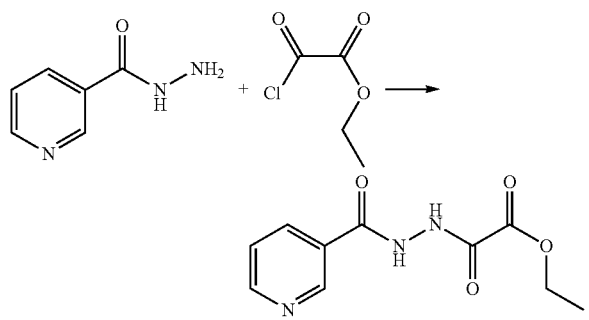

With gentle warming, 20.5 g (149.4 mmol) of nicotinic acid hydrazide were dissolved in 400 ml of DMF, and 50 ml (346 mmol) of triethylamine were added. With ice bath cooling, 18 ml (160 mmol) of ethyl oxalyl chloride in 40 ml of dichloromethane were added using a dropping funnel. The mixture was stirred at room temperature for another 15 min and then concentrated by evaporation. Aq. citric acid, dilute aqueous sodium hydroxide solution and aq. sodium chloride to pH=7 were added to the residue, and the mixture was extracted 10 times with methyl acetate. The combined organic phases were dried with magnesium sulphate and concentrated by evaporation.

Yield: 32.5 g (91% of theory), logP (HCOOH) −0.13

Step 2: Ethyl 5-pyridin-3-yl-[1,3,4]thiadiazole-2-carboxylate

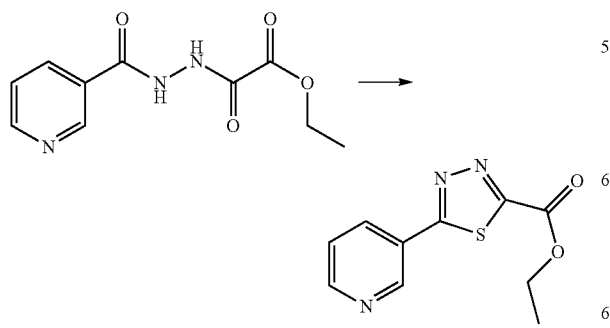

38.1 g (160.6 mmol) of ethyl oxo-[N'-(pyridin-3-carbonyl)hydrazino]acetate and 37 g (91 mmol) of Lawessons reagent in 500 ml of toluene were heated under reflux for 1 h. After cooling, the mixture was concentrated by evaporation, ethyl acetate and citrate buffer to pH=6 were added, insoluble material was filtered off, the mixture was extracted 4 times with ethyl acetate and the combined organic phases were dried with magnesium sulphate and concentrated by evaporation. The residue was recrystallized from benzotrifluoride, which involved brief heating to boiling point with activated carbon and hot filtration.

Yield: 16.2 g (42% of theory), logP (HCOOH) 1.41

1H-NMR (D6-DMSO): 1.4 (t, 3H), 4.5 (m, 2H), 7.65 (m, 1H), 8.45 (m, 1H), 8.7 (m, 1H), 9.25 (s, 1H)

Step 3: 1-(5-Pyridin-3-yl-[1,3,4]thiadiazol-2-yl)ethanone

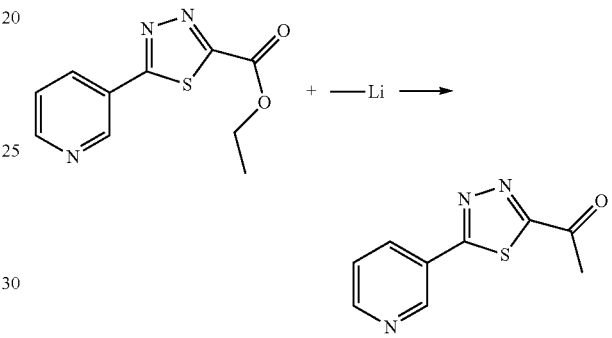

4 g (17 mmol) of ethyl 5-pyridin-3-yl-[1,3,4]thiadiazole-2-carboxylate were dissolved in 500 ml of THF, and 11.35 ml (34 mmol) of a 3 molar solution of methyllithium were added with dry-ice bath cooling. The mixture was stirred for 0.5 h, ethyl acetate and then aq. citric acid were added to the cold mixture and, after thawing, the mixture was extracted three times in total with ethyl acetate. The combined organic phases were dried with magnesium sulphate and concentrated by evaporation. The residue was purified by chromatography on silica gel (cyclohexane/acetone).

Yield 1.66 g (45% of theory calculated proportionally from 2 batches), logP (HCOOH) 1.16

1H-NMR (D6-DMSO) 2.75 (s, 3H), 7.6 (m, 1H), 8.45 (d, 1H), 8.8 (d, 1H), 9.2 (s, 1H)

Step 4: (3-Dimethylamino-1-(5-pyridin-3-yl-[1,3,4]thiadiazol-2-yl)propenone

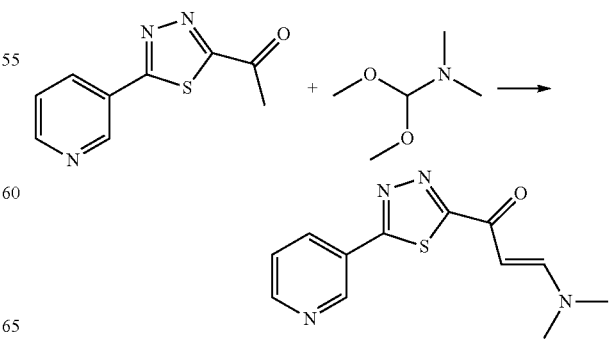

3.48 g (17 mmol) of 1-(5-pyridin-3-yl-[1,3,4]thiadiazol-2-yl)ethanone and 26.6 ml (199 mmol) of DMF-DMA were stirred on a very short distillation bridge at 105° C. for 2 h and then stirred at boiling point for 2 h. The mixture was concentrated by evaporation and the residue was chromatographed on silica gel (cyclohexane/acetone).

Yield: 1.4 g (25% of theory), logP (HCOOH) 1.05

1H-NMR (CD3CN): 3.0 (s, 3H), 3.2 (s, 3H), 6.1 (d, 1H), 7.5 (m, 1H), 8.0 (m, 1H), 8.3 (m, 1H), 8.7 (m, 1H), 9.2 (s, 1H)

Step 5: 4-(5-Pyridin-3-yl-[1,3,4]thiadiazol-2-yl)-[2,2']bipyrimidinyl

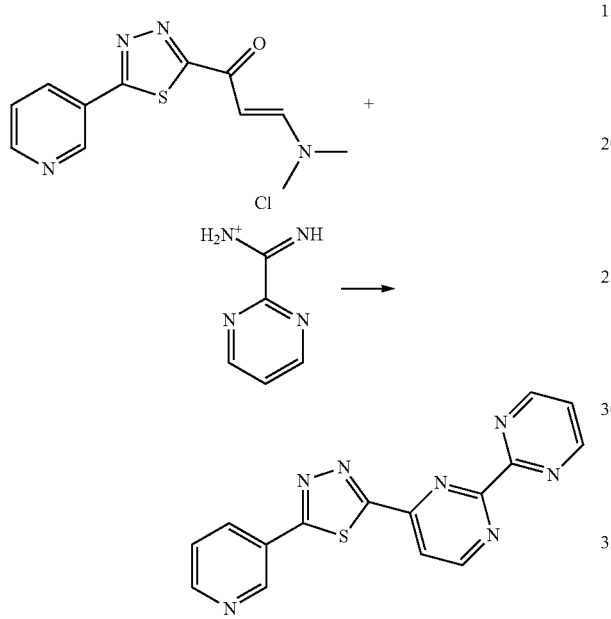

0.3 g (1.1 mmol) of (3-dimethylamino-1-(5-pyridin-3-yl-[1,3,4]thiadiazol-2-yl)propenone in 8 ml of ethanol and 0.18 g (1.2 mmol) of 2-amidiniumpyrimidine hydrochloride and 0.4 ml (1.2 mmol) of a 21% strength ethanolic sodium ethoxide solution were heated under reflux for 16 h. The mixture was concentrated by evaporation, aq. citric acid, aq. sodium chloride and dilute aqueous sodium hydroxide solution to pH=12 were added, the mixture was extracted repeatedly with chloroform/isopropanol at 10% and the combined organic phases were dried with sodium sulphate and concentrated by evaporation. The residue was suspended in DMSO/acetonitrile and filtered off with suction, and the residue was washed with MTBE and dried.

Yield: 0.2 g (54% of theory), logP (HCOOH) 1.07

1H-NMR (D6-DMSO) 7.65 (m, 1H), 7.7 (m, 1H), 8.45 (m, 1H), 8.55 (m, 1H), 8.8 (m, 1H), 9.1 (m, 2H), 9.3 (m, 2H)

Example 10

Step 1: N-Formylnicotinic acid hydrazide

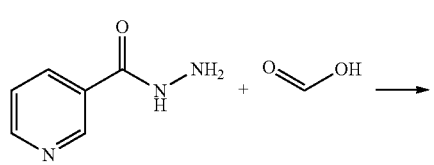

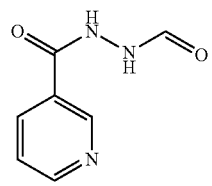

25 g (182 mmol) of nicotinic acid hydrazide were stirred in 50 ml (1325 mmol) of formic acid for 16 h, 500 ml of diethyl ether were added and the precipitate formed was filtered off with suction. The filter residue was washed with diethyl ether and dried.

Yield: 28.1 g (93% of theory).

1H-NMR (D6-DMSO): 7.5 (m, 1H), 8-8.3 (m, 2H), 8.75 (m, 1H), 9 (s, 1H), 10 (s, 1H), 10.5 (s, 1H)

Step 2: 3-[1,3,4]Thiadiazol-2-ylpyridine

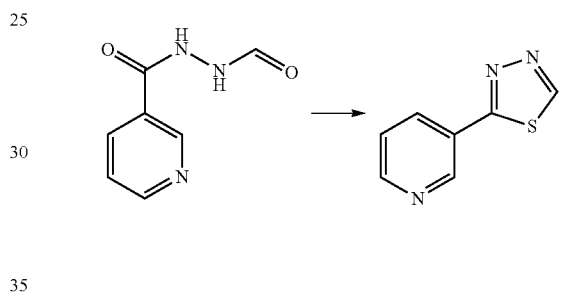

26 g (151.3 mmol) of formylnicotinic acid hydrazide and 45.9 g (113.5 mmol) of Lawessons reagent in 500 ml of anisole with a few drops of pyridine were stirred at 120° C. for 16 h. The mixture was concentrated by evaporation, aq. citric acid and dilute aqueous sodium hydroxide solution to pH=10 were added, and the mixture was stirred for 1 h and extracted three times with ethyl acetate. The combined organic phases were dried with sodium sulphate and concentrated and the residue was recrystallized from benzotrifluoride/dioxane 5:1, which involved heating to boiling point with activated carbon and hot filtration.

Yield: 7.6 g (30% of theory), logP (HCOOH) 0.15

1H-NMR (CD3CN) 7.5 (ddd, 1H), 8.35 (m, 1H), 8.7 (d, 1H), 9.15 (m, 1H), 9.3 (s, 1H)

Step 3: 2-[6-(5-Pyridin-3-yl-[1,3,4]thiadiazol-2-yl)pyridin-2-yl]pyrimidine

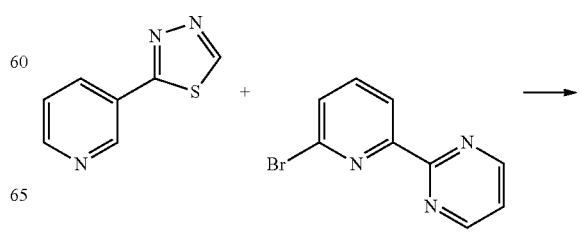

-continued

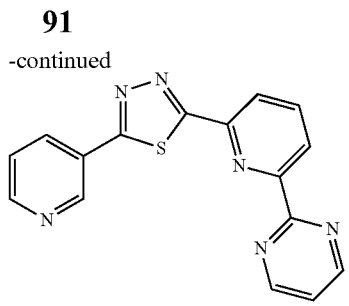

Under argon, 10.8 ml (4.59 mmol) of a 10% strength solution of tri-t-butylphosphane in hexane were added to 0.25 g (1.1 mmol) of palladium(II) acetate in 60 ml of DMF. The hexane was removed under reduced pressure, 1.5 g (9.1 mmol) of 3-[1,3,4]thiadiazol-2-ylpyridine, 2.38 g (10.1 mmol) of 2-(6-bromopyridin-2-yl)pyrimidine, 2.54 g (18.3 mmol) of potassium carbonate and about 0.5 g of tetrabutylammonium chloride were then added and the mixture was stirred at 130° C. for 16 h. The mixture was concentrated by evaporation, aq. citric acid, dilute aqueous sodium hydroxide solution, aq. sodium chloride and ethyl acetate were added to pH=8, the mixture was extracted three times with ethyl acetate and the combined organic phases were dried with sodium sulphate and concentrated by evaporation. The residue was purified by chromatography on silica gel.

Yield: 0.35 g (11% of theory), logP (HCOOH) 1.54

1H-NMR (D6-DMSO): 7.6 (m, 2H), 8.25 (t, 1H), 8.45 (m, 2H), 8.55 (m, 1H), 8.75 (m, 1H), 9.05 (d, 2H), 9.3 (s, 1H)

Further compounds according to the invention were prepared in an analogous manner (table).

Example 11

Step 1:

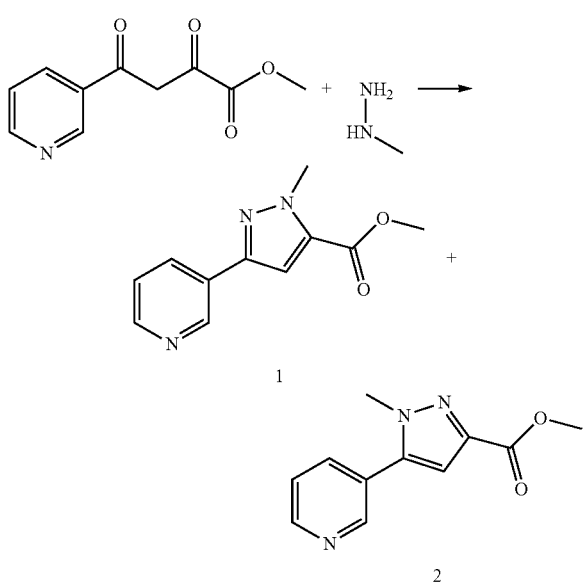

15.0 g (72.4 mmol) of the diketo ester and 3.34 g (72.4 mmol) of methylhydrazine in 300 ml of ethanol were heated at reflux for 2 h, and the solvent was then removed under reduced pressure. The residue was purified by column chromatography (silica gel, mobile phase cyclohexane/ethyl acetate).

Yield:
6.55 g (41% of theory) isomer 1, logP (HCOOH)=0.84
2.23 g (14% of theory) isomer 2, logP (HCOOH)=0.77

Step 2:

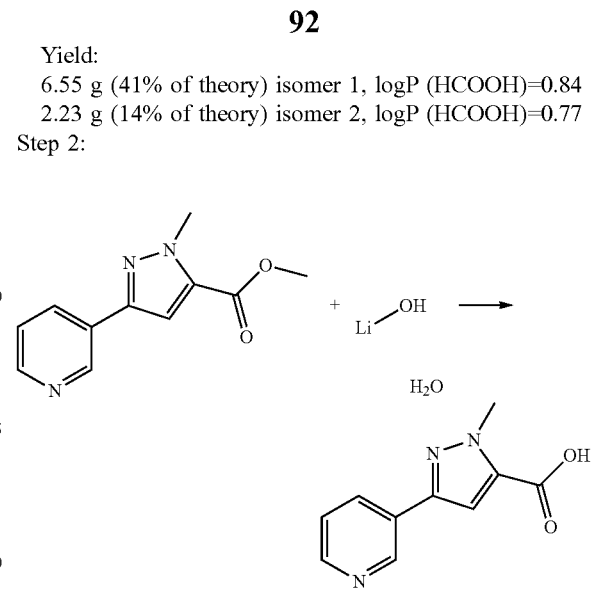

6.55 g (30.15 mmol) of the methyl ester were dissolved in 400 ml of tetrahydrofuran and 250 ml of water, a solution of 2.53 g (60.30 mmol) of lithium hydroxide hydrate in 150 ml of water was added and the mixture was stirred at room temperature for 12 h. For work-up, the mixture was acidified with 1N hydrochloric acid and the tetrahydrofuran was removed under reduced pressure, resulting in the precipitation of the product. The product was filtered off with suction and dried.

Yield: 6.08 g (99% of theory)

Step 3:

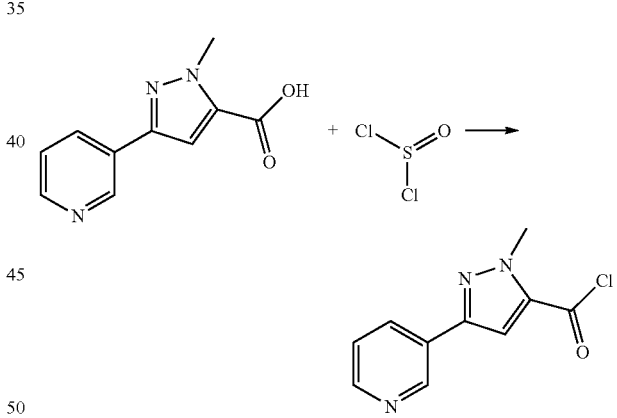

2.00 g (9.843 mmol) of the acid in 50 ml of thionyl chloride were heated at reflux for 2 h, and the solvent was then removed under reduced pressure.

Yield: 2.12 g (90% of theory)

Step 4:

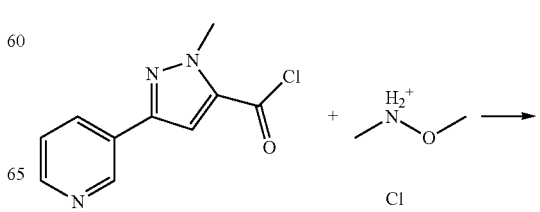

-continued

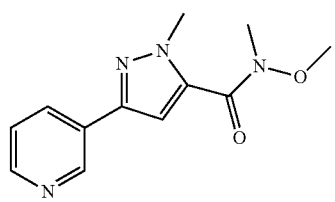

1.584 g (16.24 mmol) of dimethylhydroxylamine hydrochloride and 6.98 g (54.14 mmol) of diisopropylethylamine were initially charged in 100 ml of dioxane, a solution of 3.00 g (13.53 mmol) of the acid chloride in a little dioxane was added dropwise and the mixture was stirred at room temperature for 12 h. For work-up, the solvent was removed under reduced pressure and the residue was purified by column chromatography (silica gel, mobile phase cyclohexane/ethyl acetate).

Yield: 1.927 g (56% of theory), logP (HCOOH)=0.49

Step 5:

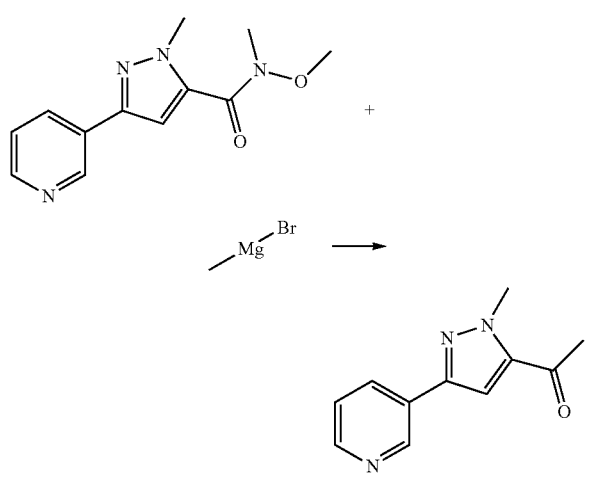

8.05 ml (11.27 mmol) of a 1.4M solution of methylmagnesium bromide in toluene/THF were initially charged, a solution of 1.85 g (7.512 mmol) of the methoxymethylamide in dichloromethane was added dropwise and the mixture was stirred at room temperature for 12 h. For work-up, the ammonium chloride solution was added, and after 30 min the org phase was separated off, dried with sodium sulphate and concentrated using a rotary evaporator.

Yield: 1.387 g (90% of theory), logP (HCOOH)=0.61

Step 6:

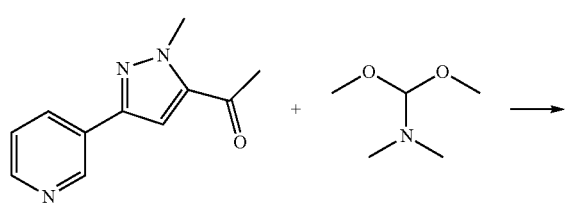

-continued

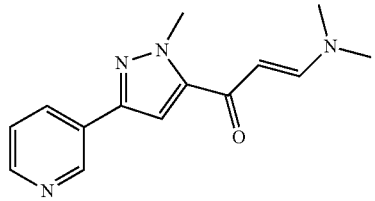

1.00 g (4.969 mmol) of the acetylpyrazole and 0.77 g (6.46 mmol) of DMF acetal were stirred at 100° C. for 12 h, and excess reagent was removed under reduced pressure.

Yield: 1.27 g (99.7% of theory), logP (HCOOH)=0.60

Step 7:

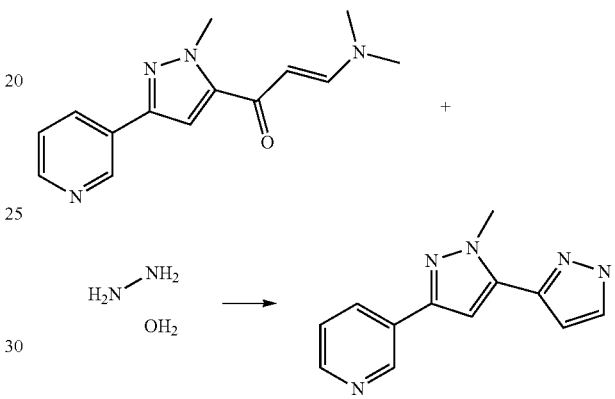

700 mg (2.731 mmol) of the pyrazole derivative and 301 mg (6.008 mmol) of hydrazine hydrate in 40 ml of ethanol were boiled under reflux for 1 h, and the solvent was removed on a rotary evaporator.

Yield: 624 mg (99% of theory), logP (HCOOH)=0.42

1H-NMR (d6-DMSO)=4.1 (s, 3H), 6.65 (m, 1H), 7.08 (m, 1H), 7.42 (m, 1H), 7.82 (m, 1H), 8.15 (m, 1H), 8.50 (m, 1H, 9.03 (m, 1H) ppm.

Step 8:

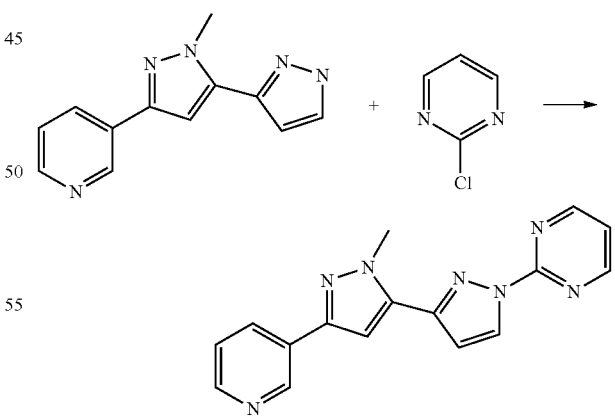

120 mg (0.533 mmol) of the pyrazole derivative, 61 mg (0.533 mmol) of 2-chloropyrimidine and 32 mg (0.799 mmol) of sodium hydride (60%) in 5 ml of dimethylformamide were stirred at 80° C. for 12 h, the solvent was removed on a rotary evaporator and the crude product was purified by chromatography (silica gel, mobile phase cyclohexane/ethyl acetate).

Yield: 113 mg (70% of theory), logP (HCOOH)=1.00

1H-NMR (d6-DMSO)=4.25 (s, 3H), 7.03 (m, 1H), 7.29 (m, 1H), 7.45 (m, 1H), 7.50 (m, 1H), 8.18 (m, 1H), 8.53 (m, 3H), 8.78 (m, 1H), 8.92 (m, 2H), 9.05 (m, 1H) ppm.

Example 12

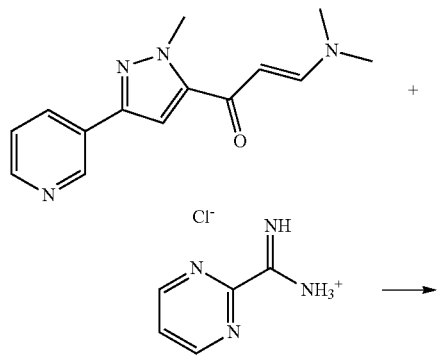

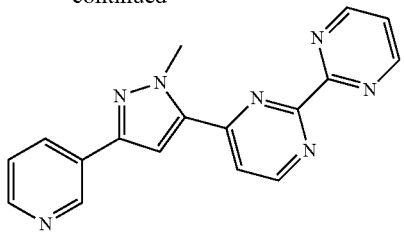

100 mg (0.39 mmol) of the pyrazole derivative described above, 69 mg (0.43 mmol) of the amidine and 153 mg (0.47 mmol) of sodium ethoxide in 5 ml of ethanol were heated at reflux for 12 h, the solvent was removed on a rotary evaporator and the crude product was purified by chromatography (silica gel, mobile phase cyclohexane/ethyl acetate).

Yield: 70 mg (57% of theory), logP (HCOOH)=0.65

1H-NMR (d6-DMSO)=4.42 (s, 3H), 7.45 (m, 1H), 7.65 (m, 1H), 7.70 (m, 1H), 8.05 (m, 1H), 8.20 (m, 1H), 8.55 (m, 1H), 9.05-9.13 (m, 4H) ppm.

Further novel compounds according to the invention are listed in the table below.

| Ex. No. | logP [1] (HCOOH) | Formula | (M+) + 1 (LC/MS) |
|---|---|---|---|
| Preparation Example 1 | 1.17 | | 333.1 |
| Preparation Example 2 | 2.30 | | |
| Preparation Example 3 | 1.48 | | 321.1 |
| Preparation Example 4 | 1.58 | | |

-continued
| Ex. No. | logP [1) ](HCOOH) | Formula | (M+) + 1 (LC/MS) |
|---|---|---|---|
| Preparation Example 5 | 1.53 | 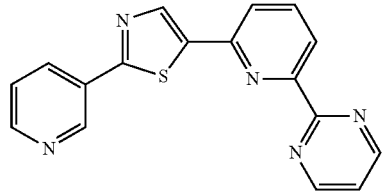 [SMILES: c1cnc(-c2cccc(-c3cnc(-c4cccnc4)s3)n2)nc1] | 318.1 |
| Preparation Example 6 | 1.73 | 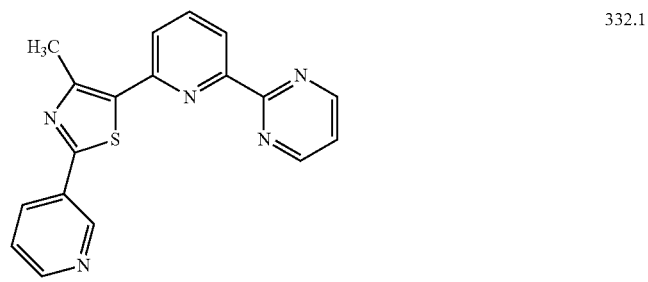 | 332.1 |
| Preparation Example 7 | 1.56 | 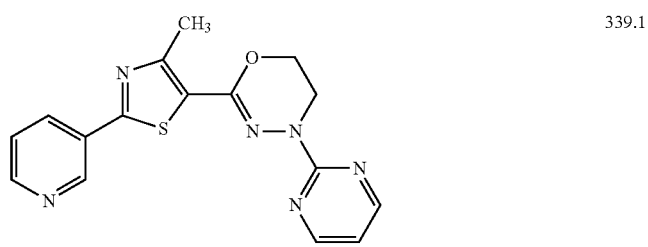 | 339.1 |
| Preparation Example 8 | 1.82 | 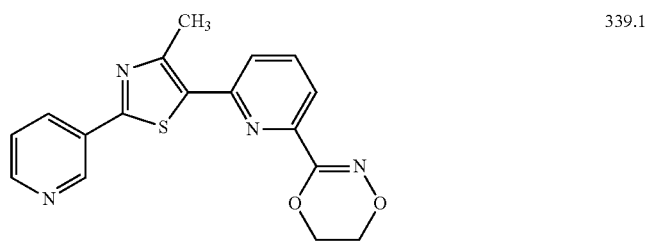 | 339.1 |
| Preparation Example 9 | 1.07 | 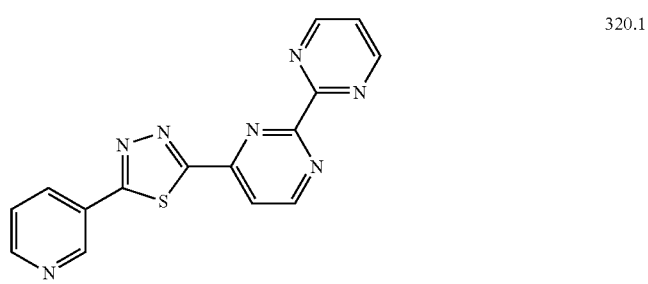 | 320.1 |
| Preparation Example 10 | 1.54 | 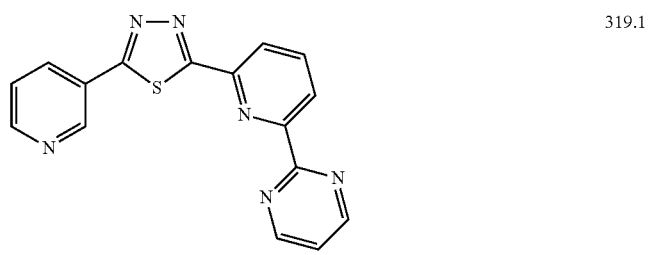 | 319.1 |

| Ex. No. | logP [1] (HCOOH) | Formula | (M+) + 1 (LC/MS) |
|---|---|---|---|
| Preparation Example 11 | 1.00 | 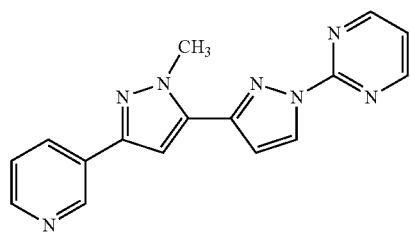 [SMILES: Cn1nc(-c2cccnc2)cc1-c1ccn(-c2ncccn2)n1] | 304.1 |
| Preparation Example 12 | 0.65 | 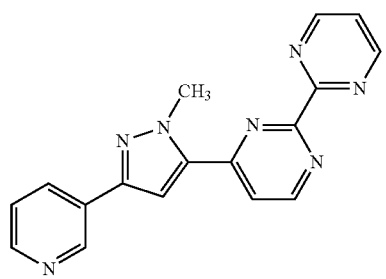 | 316.1 |
| 13 | 3.23 | 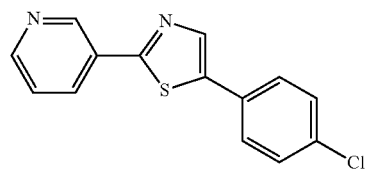 [SMILES: Clc1ccc(-c2cnc(-c3cccnc3)s2)cc1] | |
| 14 | 2.63 | 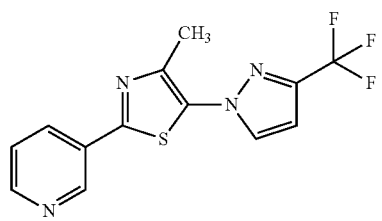 [SMILES: Cc1nc(-c2cccnc2)sc1-n1ccc(C(F)(F)F)n1] | |
| 15 | 1.67 | 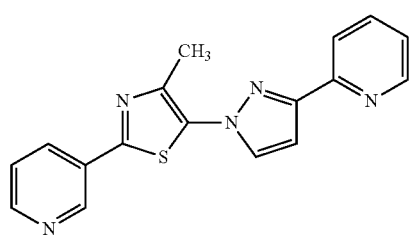 [SMILES: Cc1nc(-c2cccnc2)sc1-n1ccc(-c2ccccn2)n1] | |
| 16 | 1.72 | 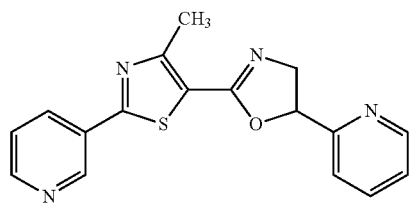 [SMILES: Cc1nc(-c2cccnc2)sc1C1=NCC(c2ccccn2)O1] | |

-continued

| Ex. No. | logP [1] (HCOOH) | Formula | (M+) + 1 (LC/MS) |
|---|---|---|---|
| 17 | 3.55 | | |
| 18 | 1.10 | | |
| 19 | 1.77 | | |
| 20 | 2.28 | | |
| 21 | 3.01 | | 322.0 |
| 22 | 1.74 | | 321.1 |
| 23 | 2.20 | | |

-continued
| Ex. No. | logP [1] (HCOOH) | Formula | (M+) + 1 (LC/MS) |
|---|---|---|---|
| 24 | 2.94 | 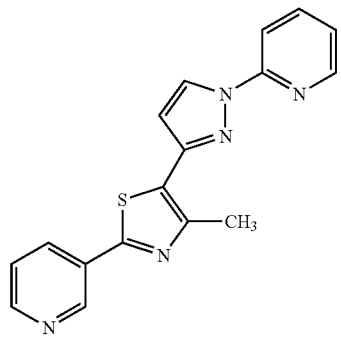 [SMILES: Cc1nc(-c2cccnc2)sc1-c1ccn(-c2ccccn2)n1] | |
| 25 | 2.39 | 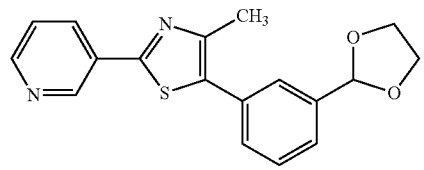 [SMILES: Cc1nc(-c2cccnc2)sc1-c1cccc(C2OCCO2)c1] | |
| 26 | 1.47 | 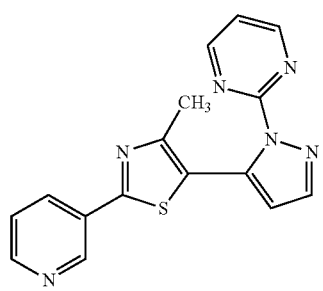 [SMILES: Cc1nc(-c2cccnc2)sc1-c1ccnn1-c1ncccn1] | |
| 27 | 1.69 | 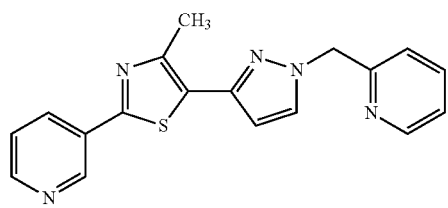 [SMILES: Cc1nc(-c2cccnc2)sc1-c1ccn(Cc2ccccn2)n1] | |
| 28 | 3.08 | 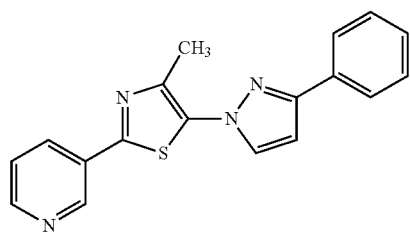 [SMILES: Cc1nc(-c2cccnc2)sc1-n1ccc(-c2ccccc2)n1] | |
| 29 | 1.47 | 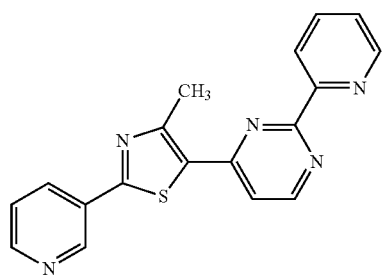 [SMILES: Cc1nc(-c2cccnc2)sc1-c1ccnc(-c2ccccn2)n1] | |

-continued
| Ex. No. | logP [1] (HCOOH) | Formula | (M+) + 1 (LC/MS) |
|---|---|---|---|
| 30 | 2.00 | 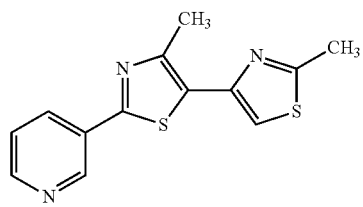 [SMILES: Cc1nc(-c2sc(-c3cccnc3)nc2C)cs1] | |
| 31 | 2.66 | 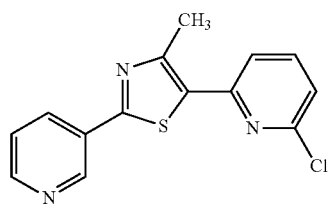 [SMILES: Cc1nc(-c2cccnc2)sc1-c1cccc(Cl)n1] | |
| 32 | 1.23 | 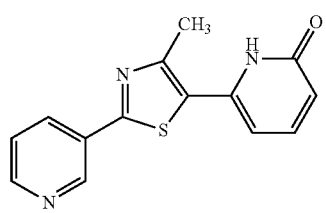 [SMILES: Cc1nc(-c2cccnc2)sc1-c1cccc(=O)[nH]1] | |
| 33 | 2.21 | 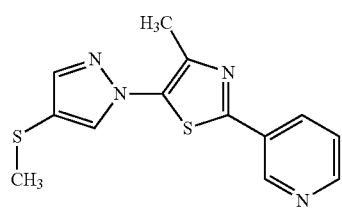 [SMILES: CSc1cnn(-c2sc(-c3cccnc3)nc2C)c1] | |
| 34 | 2.84 | 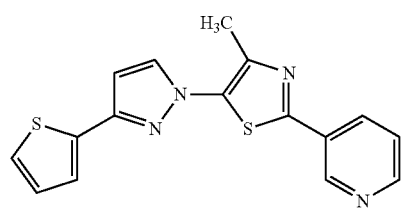 [SMILES: Cc1nc(-c2cccnc2)sc1-n1ccc(-c2cccs2)n1] | |
| 35 | 1.92 | 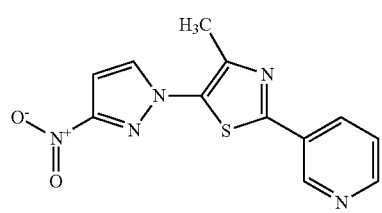 [SMILES: Cc1nc(-c2cccnc2)sc1-n1ccc([N+](=O)[O-])n1] | |

| Ex. No. | logP [1] (HCOOH) | Formula | (M+) + 1 (LC/MS) |
|---|---|---|---|
| 36 | 3.33 | 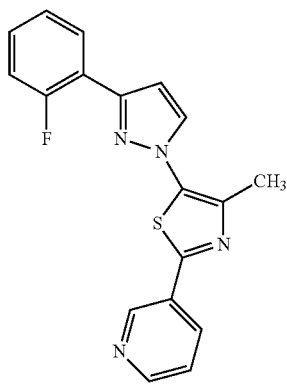 [SMILES: Cc1nc(-c2cccnc2)sc1-n1ccc(-c2ccccc2F)n1] | |
| 37 | 3.81 | 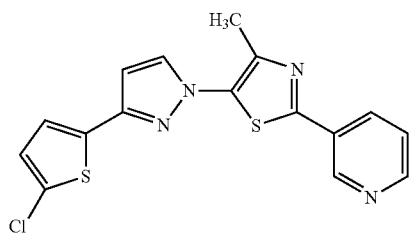 [SMILES: Cc1nc(-c2cccnc2)sc1-n1ccc(-c2ccc(Cl)s2)n1] | |
| 38 | 3.94 | 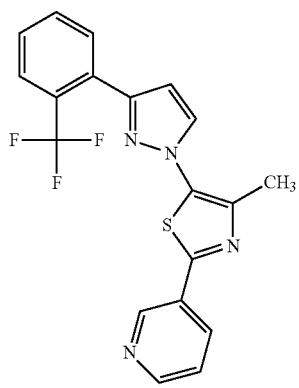 [SMILES: Cc1nc(-c2cccnc2)sc1-n1ccc(-c2ccccc2C(F)(F)F)n1] | |
| 39 | 1.55 | 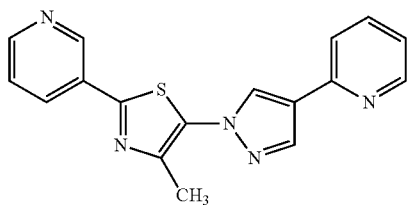 [SMILES: Cc1nc(-c2cccnc2)sc1-n1cc(-c2ccccn2)cn1] | |
| 40 | 2.43 | 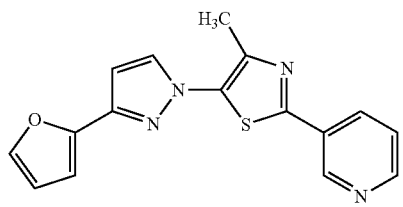 [SMILES: Cc1nc(-c2cccnc2)sc1-n1ccc(-c2ccco2)n1] | |

| Ex. No. | logP [1] (HCOOH) | Formula | (M+) + 1 (LC/MS) |
|---|---|---|---|
| 41 | 2.03 | 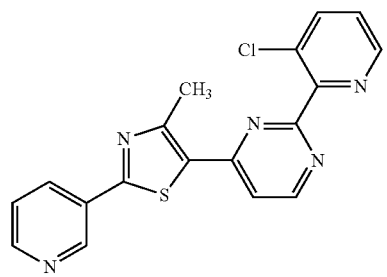 [SMILES: Cc1nc(-c2cccnc2)sc1-c1ccnc(-c2ncccc2Cl)n1] | |
| 42 | 3.97 | 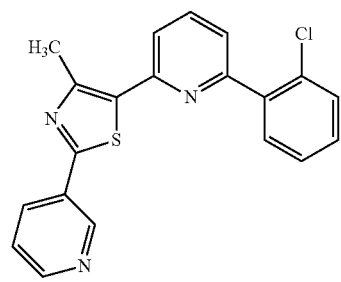 [SMILES: Cc1nc(-c2cccnc2)sc1-c1cccc(-c2ccccc2Cl)n1] | |
| 43 | 1.86 | 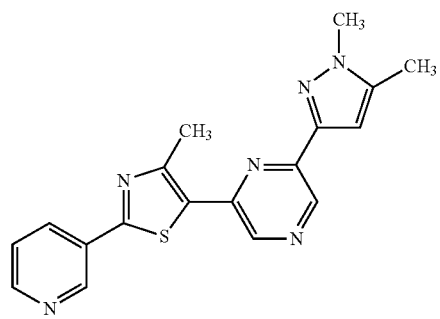 [SMILES: Cc1nc(-c2cccnc2)sc1-c1cncc(-c2cc(C)n(C)n2)n1] | |
| 44 | 2.40 | 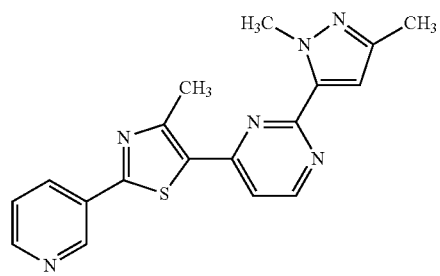 [SMILES: Cc1cc(-c2nccc(-c3sc(-c4cccnc4)nc3C)n2)n(C)n1] | |
| 45 | 2.95 | 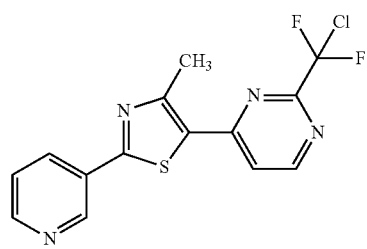 [SMILES: Cc1nc(-c2cccnc2)sc1-c1ccnc(C(F)(F)Cl)n1] | |

-continued
| Ex. No. | logP [1] (HCOOH) | Formula | (M+) + 1 (LC/MS) |
|---|---|---|---|
| 46 | 2.47 | 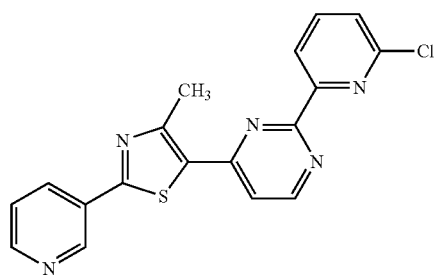 [SMILES: Cc1nc(-c2cccnc2)sc1-c1ccnc(-c2cccc(Cl)n2)n1] | |
| 47 | 1.48 | 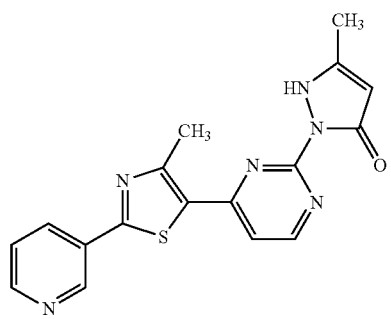 [SMILES: Cc1cc(=O)n(-c2nccc(-c3sc(-c4cccnc4)nc3C)n2)[nH]1] | |
| 48 | 2.08 | 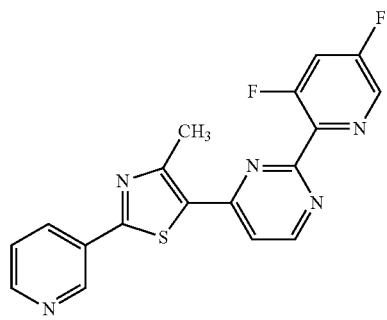 [SMILES: Cc1nc(-c2cccnc2)sc1-c1ccnc(-c2ncc(F)cc2F)n1] | |
| 49 | 2.81 | 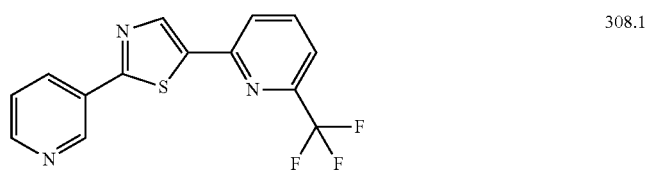 | 308.1 |
| 50 | 1.13 | 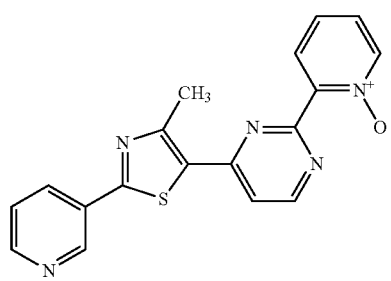 [SMILES: Cc1nc(-c2cccnc2)sc1-c1ccnc(-c2cccc[n+]2O)n1] | |

-continued
| Ex. No. | logP [1] (HCOOH) | Formula | (M+) + 1 (LC/MS) |
|---|---|---|---|
| 51 | 1.59 | 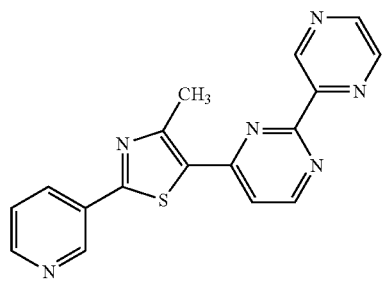 [SMILES: Cc1nc(-c2cccnc2)sc1-c1ccnc(-c2cnccn2)n1] | |
| 52 | 2.35 | 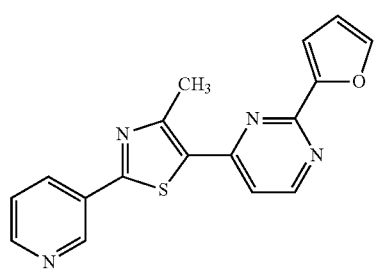 [SMILES: Cc1nc(-c2cccnc2)sc1-c1ccnc(-c2ccco2)n1] | |
| 53 | 1.58 | 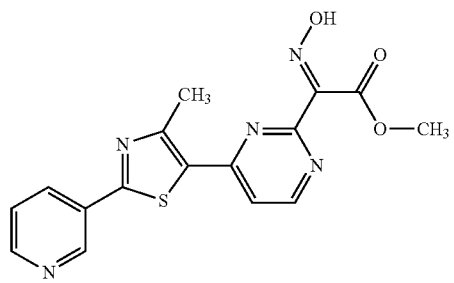 [SMILES: COC(=O)/C(=N\O)c1nccc(-c2sc(-c3cccnc3)nc2C)n1] | |
| 54 | 1.49 | 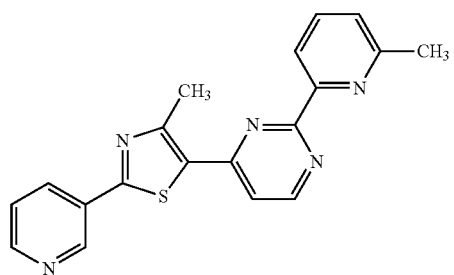 [SMILES: Cc1cccc(-c2nccc(-c3sc(-c4cccnc4)nc3C)n2)n1] | |
| 55 | 1.49 | 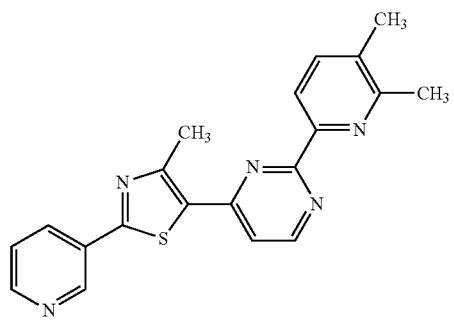 [SMILES: Cc1ccc(-c2nccc(-c3sc(-c4cccnc4)nc3C)n2)nc1C] | |

-continued
| Ex. No. | logP [1] (HCOOH) | Formula | (M+) + 1 (LC/MS) |
|---|---|---|---|
| 56 | 2.08 | 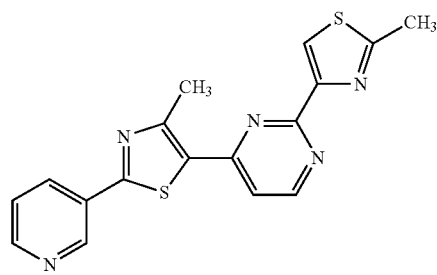 [SMILES: Cc1nc(-c2nccc(-c3sc(-c4cccnc4)nc3C)n2)cs1] | |
| 57 | 1.88 | 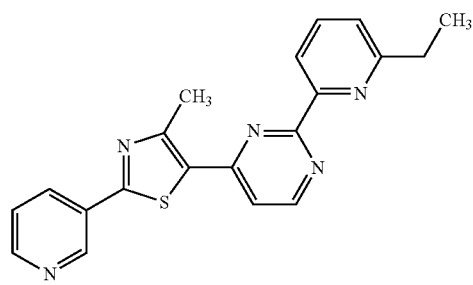 [SMILES: CCc1cccc(-c2nccc(-c3sc(-c4cccnc4)nc3C)n2)n1] | |
| 58 | 2.25 | 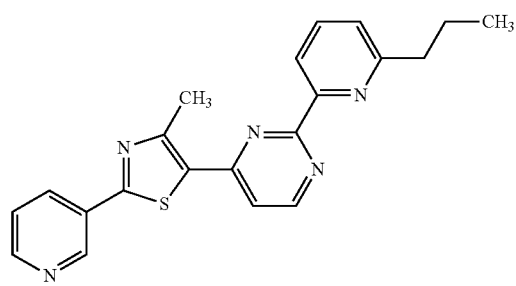 [SMILES: CCCc1cccc(-c2nccc(-c3sc(-c4cccnc4)nc3C)n2)n1] | |
| 59 | 2.12 | 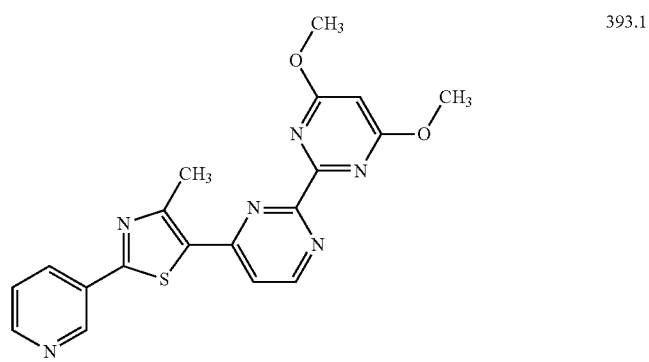 | 393.1 |
| 60 | 3.84 | 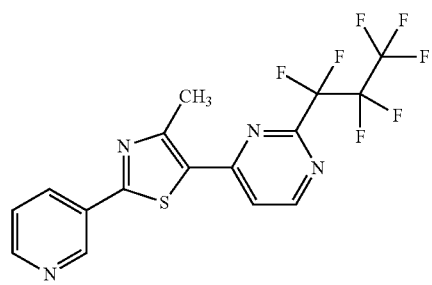 [SMILES: Cc1nc(-c2cccnc2)sc1-c1ccnc(C(F)(F)C(F)(F)C(F)(F)F)n1] | |

| Ex. No. | logP [1] (HCOOH) | Formula | (M+) + 1 (LC/MS) |
|---|---|---|---|
| 61 | 1.57 | 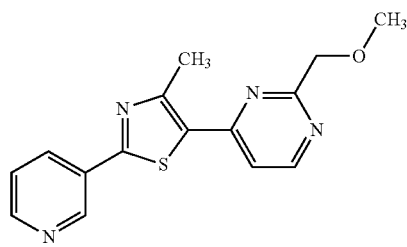 [SMILES: COCc1nccc(-c2sc(-c3cccnc3)nc2C)n1] | 299.1 |
| 62 | 3.23 | 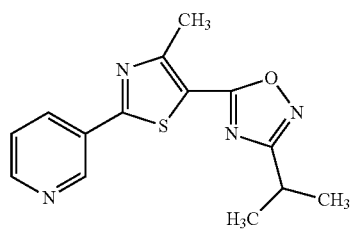 [SMILES: Cc1nc(-c2cccnc2)sc1-c1nc(C(C)C)no1] | |
| 63 | 2.51 | 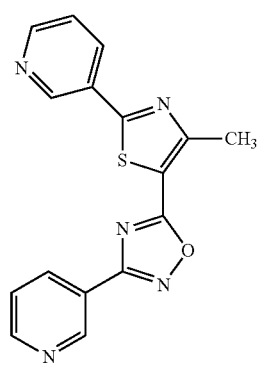 [SMILES: Cc1nc(-c2cccnc2)sc1-c1nc(-c2cccnc2)no1] | |
| 64 | 3.34 | 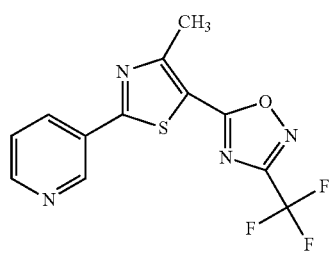 [SMILES: Cc1nc(-c2cccnc2)sc1-c1nc(C(F)(F)F)no1] | |
| 65 | 1.36 | 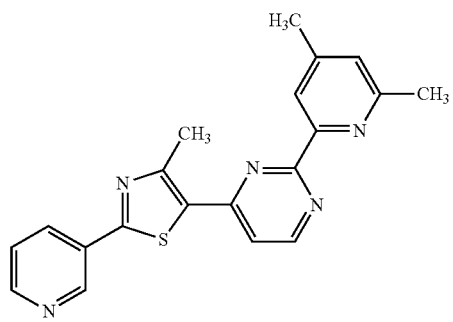 [SMILES: Cc1cc(C)nc(-c2nccc(-c3sc(-c4cccnc4)nc3C)n2)c1] | |

| Ex. No. | logP [1] (HCOOH) | Formula | (M+) + 1 (LC/MS) |
|---|---|---|---|
| 66 | 2.90 | 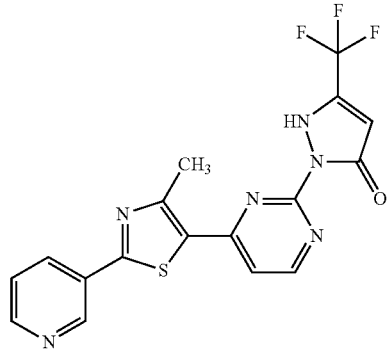 [SMILES: Cc1nc(-c2cccnc2)sc1-c1ccnc(-n2[nH]c(C(F)(F)F)cc2=O)n1] | |
| 67 | 1.90 | 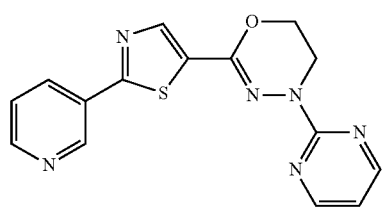 [SMILES: c1cnc(N2CCOC(c3cnc(-c4cccnc4)s3)=N2)nc1] | 325.1 |
| 68 | 1.62 | 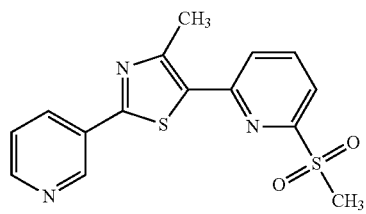 [SMILES: Cc1nc(-c2cccnc2)sc1-c1cccc(S(C)(=O)=O)n1] | |
| 69 | 1.20 | 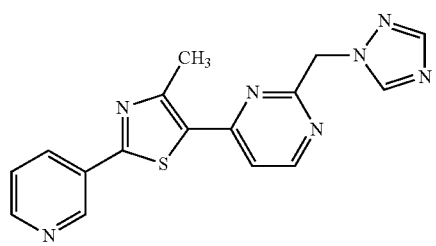 [SMILES: Cc1nc(-c2cccnc2)sc1-c1ccnc(Cn2cncn2)n1] | |
| 70 | 1.40 | 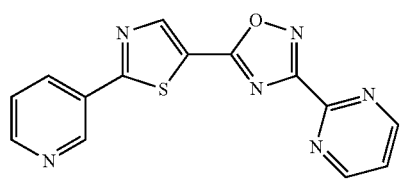 [SMILES: c1cnc(-c2noc(-c3cnc(-c4cccnc4)s3)n2)nc1] | |
| 71 | 2.70 | 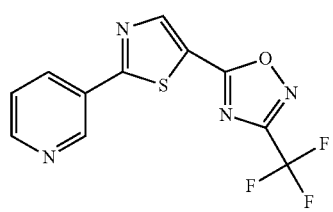 [SMILES: FC(F)(F)c1noc(-c2cnc(-c3cccnc3)s2)n1] | |

-continued
| Ex. No. | logP [1] (HCOOH) | Formula | (M+) + 1 (LC/MS) |
|---|---|---|---|
| 72 | 3.11 | 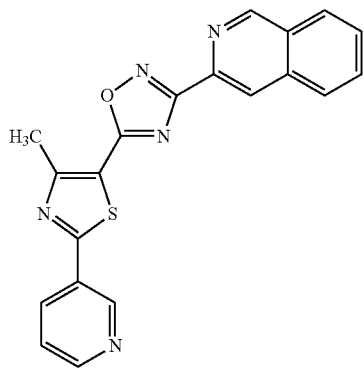 [SMILES: Cc1nc(-c2cccnc2)sc1-c1nc(-c2cc3ccccc3cn2)no1] | |
| 73 | 2.34 | 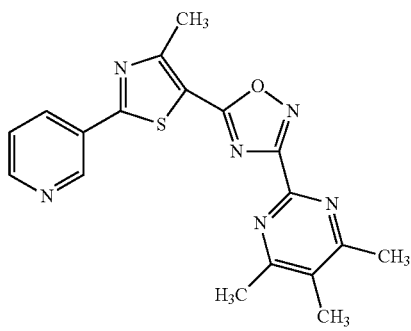 [SMILES: Cc1nc(-c2cccnc2)sc1-c1nc(-c2nc(C)c(C)c(C)n2)no1] | |
| 74 | 2.81 | 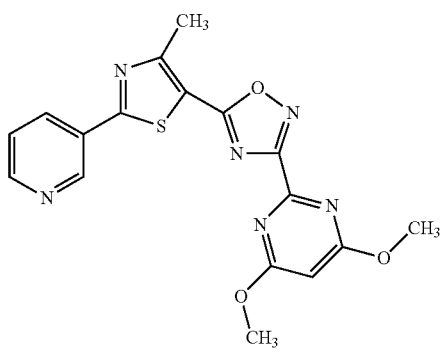 [SMILES: COc1cc(OC)nc(-c2noc(-c3sc(-c4cccnc4)nc3C)n2)n1] | |
| 75 | 2.97 | 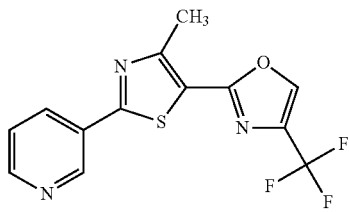 [SMILES: Cc1nc(-c2cccnc2)sc1-c1nc(C(F)(F)F)co1] | |
| 76 | 3.11 | 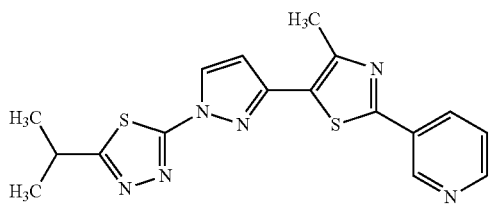 [SMILES: Cc1nc(-c2cccnc2)sc1-c1ccn(-c2nnc(C(C)C)s2)n1] | |

| Ex. No. | logP [1] (HCOOH) | Formula | (M+) + 1 (LC/MS) |
|---|---|---|---|
| 77 | 2.50 | 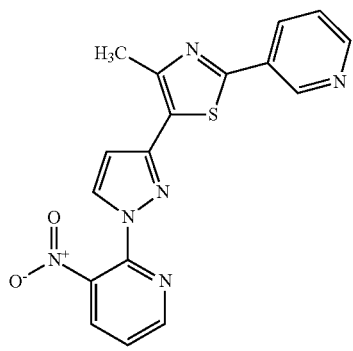 [SMILES: Cc1nc(-c2cccnc2)sc1-c1ccn(-c2ncccc2[N+](=O)[O-])n1] | |
| 78 | 2.99 | 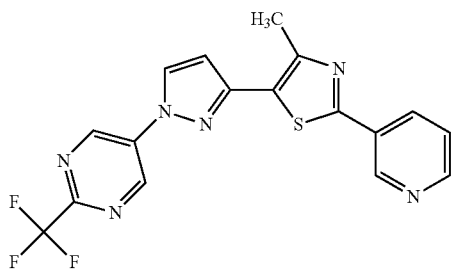 [SMILES: Cc1nc(-c2cccnc2)sc1-c1ccn(-c2cnc(C(F)(F)F)nc2)n1] | |
| 79 | 3.94 | 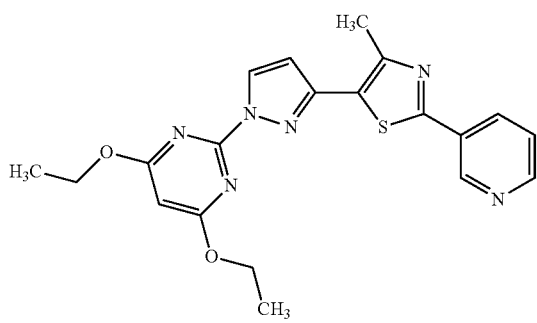 [SMILES: CCOc1cc(OCC)nc(-n2ccc(-c3sc(-c4cccnc4)nc3C)n2)n1] | |
| 80 | 2.27 | 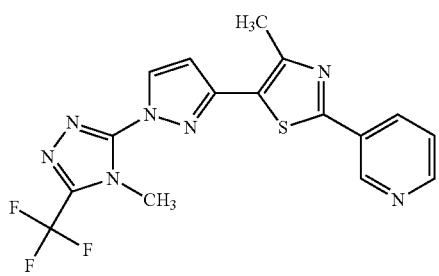 [SMILES: Cc1nc(-c2cccnc2)sc1-c1ccn(-c2nnc(C(F)(F)F)n2C)n1] | |
| 81 | 2.80 | 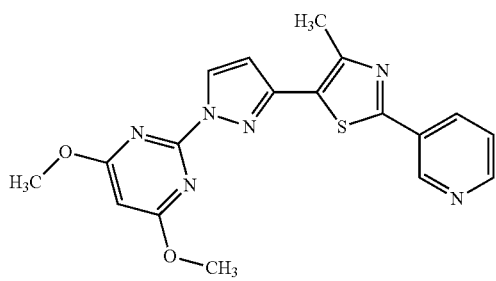 [SMILES: COc1cc(OC)nc(-n2ccc(-c3sc(-c4cccnc4)nc3C)n2)n1] | |

-continued
| Ex. No. | logP [1] (HCOOH) | Formula | (M+) + 1 (LC/MS) |
|---|---|---|---|
| 82 | 2.23 | 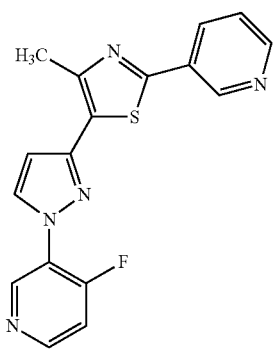 [SMILES: Cc1nc(-c2cccnc2)sc1-c1ccn(-c2cnccc2F)n1] | |
| 83 | 3.63 | 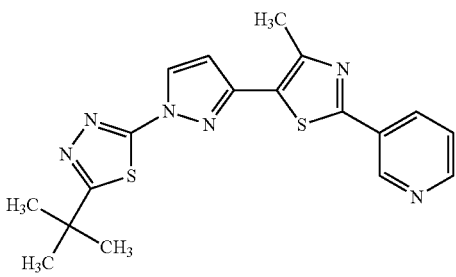 [SMILES: Cc1nc(-c2cccnc2)sc1-c1ccn(-c2nnc(C(C)(C)C)s2)n1] | |
| 84 | 2.61 | 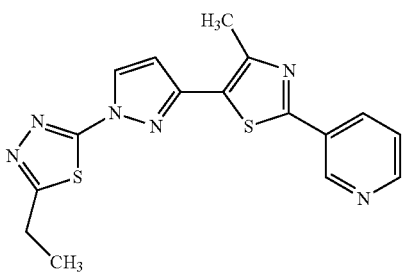 [SMILES: CCc1nnc(-n2ccc(-c3sc(-c4cccnc4)nc3C)n2)s1] | |
| 85 | 2.80 | 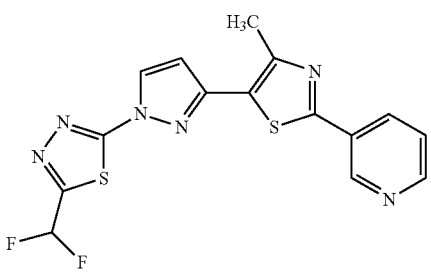 [SMILES: Cc1nc(-c2cccnc2)sc1-c1ccn(-c2nnc(C(F)F)s2)n1] | |
| 86 | 2.72 | 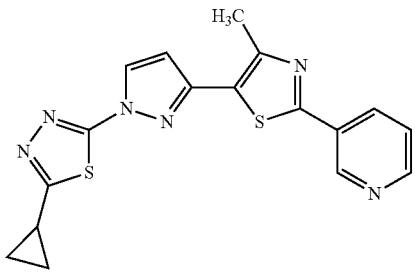 [SMILES: Cc1nc(-c2cccnc2)sc1-c1ccn(-c2nnc(C3CC3)s2)n1] | |

-continued

| Ex. No. | logP [1] (HCOOH) | Formula | (M+) + 1 (LC/MS) |
|---|---|---|---|
| 87 | 3.47 | | |
| 88 | 1.05 | | 319.1 |
| 89 | 1.48 | | 307.1 |
| 90 | 1.39 | | |
| 91 | 2.41 | | |
| 92 | 3.84 | | |

-continued
| Ex. No. | logP [1] (HCOOH) | Formula | (M+) + 1 (LC/MS) |
|---|---|---|---|
| 93 | 1.86 | 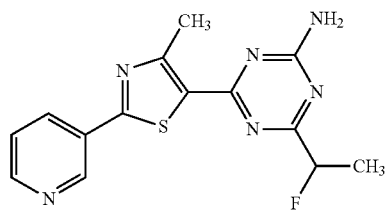 [SMILES: Cc1nc(-c2cccnc2)sc1-c1nc(N)nc(C(C)F)n1] | |
| 94 | 3.14 | 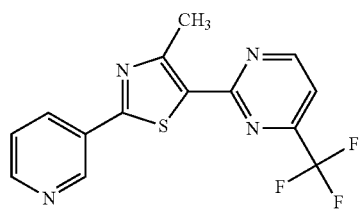 [SMILES: Cc1nc(-c2cccnc2)sc1-c1nccc(C(F)(F)F)n1] | |
| 95 | 2.03 | 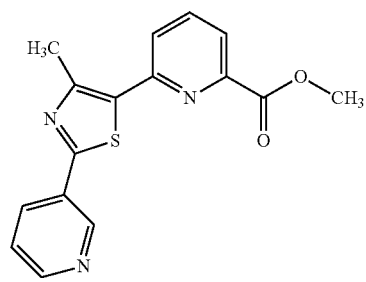 [SMILES: COC(=O)c1cccc(-c2sc(-c3cccnc3)nc2C)n1] | |
| 96 | 2.58 | 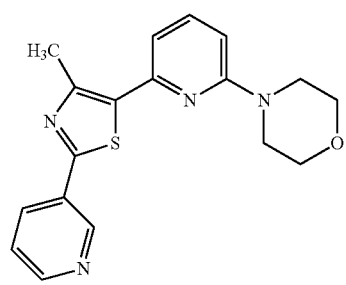 [SMILES: Cc1nc(-c2cccnc2)sc1-c1cccc(N2CCOCC2)n1] | |
| 97 | 2.93 | 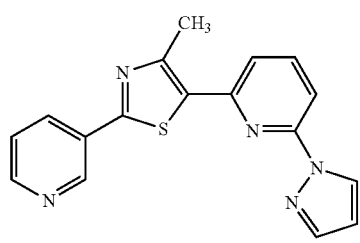 [SMILES: Cc1nc(-c2cccnc2)sc1-c1cccc(-n2cccn2)n1] | 320.1 |
| 98 | 3.55 | 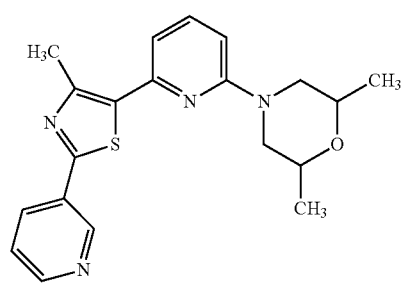 [SMILES: Cc1nc(-c2cccnc2)sc1-c1cccc(N2CC(C)OC(C)C2)n1] | |

-continued
| Ex. No. | logP [1) (HCOOH) | Formula | (M+) + 1 (LC/MS) |
|---|---|---|---|
| 99 | 3.14 | 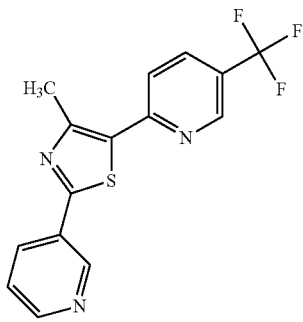 [SMILES: Cc1nc(-c2cccnc2)sc1-c1ccc(C(F)(F)F)cn1] | |
| 100 | 2.55 | 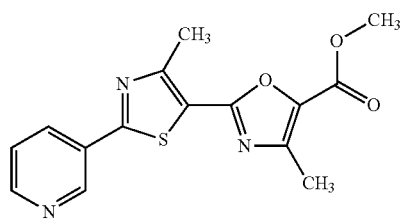 [SMILES: COC(=O)c1oc(-c2sc(-c3cccnc3)nc2C)nc1C] | |
| 101 | 2.42 | 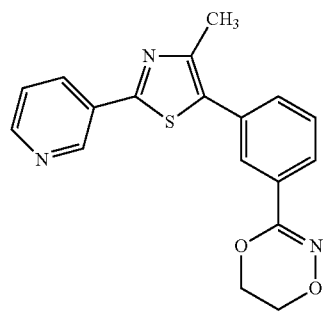 [SMILES: Cc1nc(-c2cccnc2)sc1-c1cccc(C2=NOCCO2)c1] | |
| 102 | 2.85 | 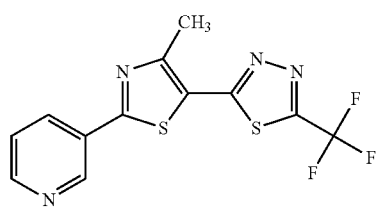 [SMILES: Cc1nc(-c2cccnc2)sc1-c1nnc(C(F)(F)F)s1] | |
| 103 | 2.55 | 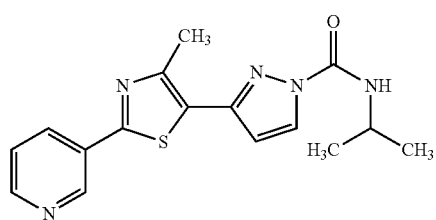 [SMILES: Cc1nc(-c2cccnc2)sc1-c1ccn(C(=O)NC(C)C)n1] | |
| 104 | 3.23 | 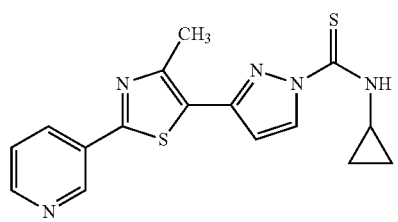 [SMILES: Cc1nc(-c2cccnc2)sc1-c1ccn(C(=S)NC2CC2)n1] | |

-continued

| Ex. No. | logP [1]) (HCOOH) | Formula | (M+) + 1 (LC/MS) |
|---|---|---|---|
| 105 | 2.69 | | |
| 106 | 3.42 | | |
| 107 | 3.85 | | |
| 108 | 3.18 | | |
| 109 | 2.72 | | |
| 110 | 3.24 | | |

| Ex. No. | logP [1] (HCOOH) | Formula | (M+) + 1 (LC/MS) |
|---|---|---|---|
| 111 | 2.80 | 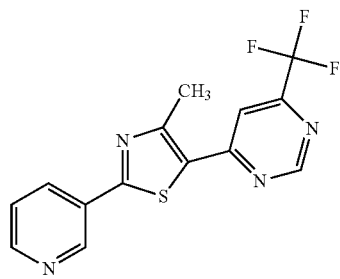 [SMILES: Cc1nc(-c2cccnc2)sc1-c1cc(C(F)(F)F)ncn1] | |
| 112 | 2.64 | 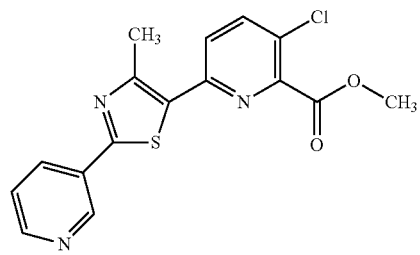 [SMILES: COC(=O)c1nc(-c2sc(-c3cccnc3)nc2C)ccc1Cl] | |
| 113 | 2.23 | 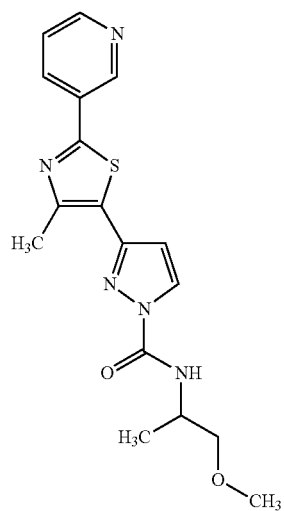 | |

| Ex. No. | logP [1] (HCOOH) | Formula | (M+) + 1 (LC/MS) |
|---|---|---|---|
| 114 | 3.27 | 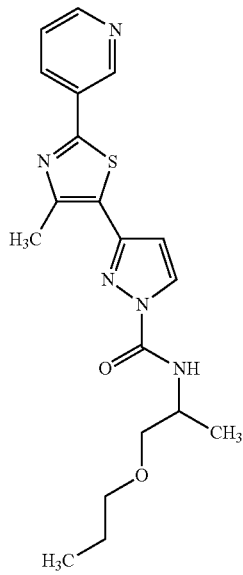 [SMILES: CCCOCC(C)NC(=O)n1ccc(-c2sc(-c3cccnc3)nc2C)n1] | |
| 115 | 2.20 | 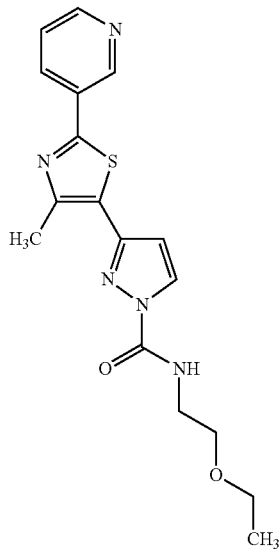 [SMILES: CCOCCNC(=O)n1ccc(-c2sc(-c3cccnc3)nc2C)n1] | |

| Ex. No. | logP [1] (HCOOH) | Formula | (M+) + 1 (LC/MS) |
|---|---|---|---|
| 116 | 2.61 | 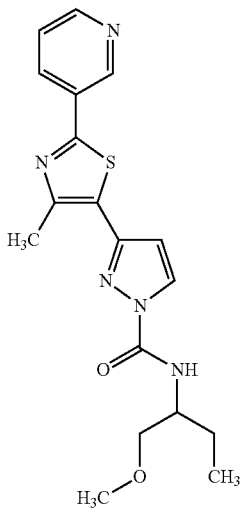 [SMILES: CCC(COC)NC(=O)n1ccc(-c2sc(-c3cccnc3)nc2C)n1] | |
| 117 | 3.18 | 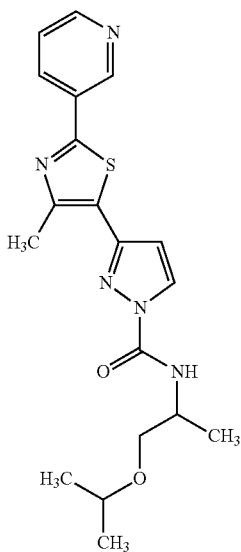 [SMILES: Cc1nc(-c2cccnc2)sc1-c1ccn(C(=O)NC(C)COC(C)C)n1] | |
| 118 | 2.69 | 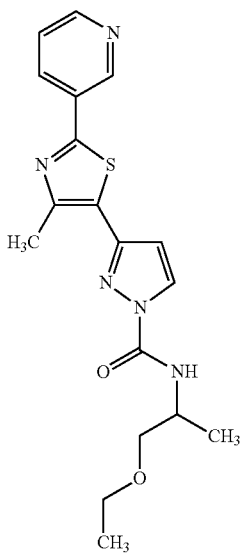 [SMILES: CCOCC(C)NC(=O)n1ccc(-c2sc(-c3cccnc3)nc2C)n1] | |

-continued
| Ex. No. | logP [1] (HCOOH) | Formula | (M+) + 1 (LC/MS) |
| --- | --- | --- | --- |
| 119 | 3.23 | 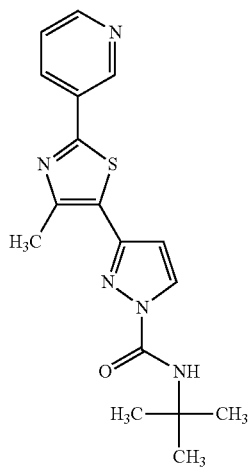 [SMILES: Cc1nc(-c2cccnc2)sc1-c1ccn(C(=O)NC(C)(C)C)n1] | |
| 120 | 2.89 | 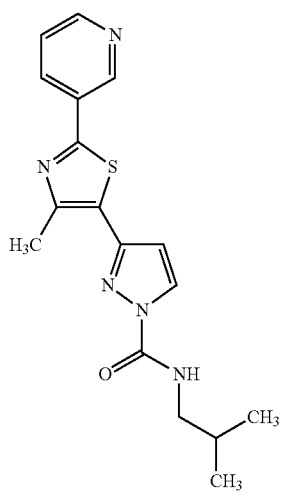 [SMILES: Cc1nc(-c2cccnc2)sc1-c1ccn(C(=O)NCC(C)C)n1] | |
| 121 | 2.05 | 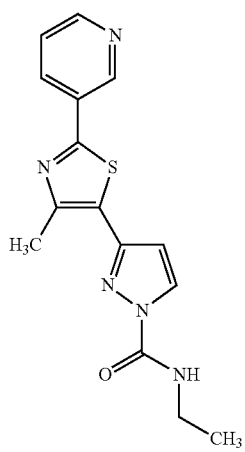 [SMILES: CCNC(=O)n1ccc(-c2sc(-c3cccnc3)nc2C)n1] | |

| Ex. No. | logP [1] (HCOOH) | Formula | (M+) + 1 (LC/MS) |
|---|---|---|---|
| 122 | 3.56 | 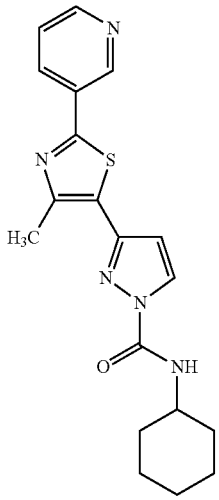 [SMILES: Cc1nc(-c2cccnc2)sc1-c1ccn(C(=O)NC2CCCCC2)n1] | |
| 123 | 2.46 | 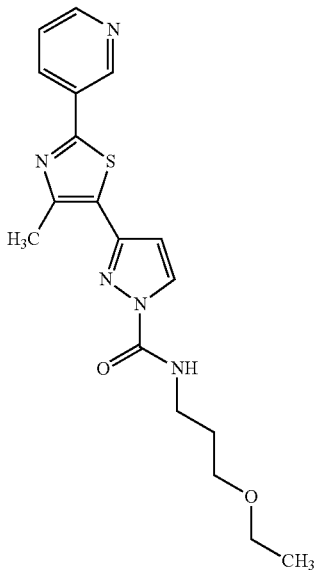 [SMILES: CCOCCCNC(=O)n1ccc(-c2sc(-c3cccnc3)nc2C)n1] | |
| 124 | 3.09 | 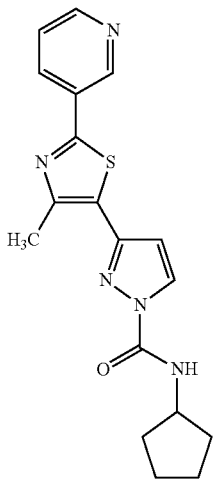 [SMILES: Cc1nc(-c2cccnc2)sc1-c1ccn(C(=O)NC2CCCC2)n1] | |

| Ex. No. | logP [1] (HCOOH) | Formula | (M+) + 1 (LC/MS) |
|---|---|---|---|
| 125 | 2.08 | 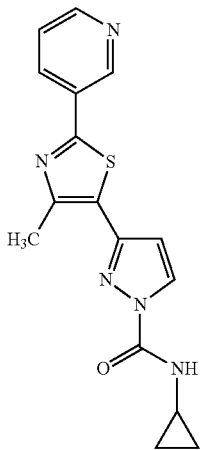 [SMILES: Cc1nc(-c2cccnc2)sc1-c1ccn(C(=O)NC2CC2)n1] | |
| 126 | 1.87 | 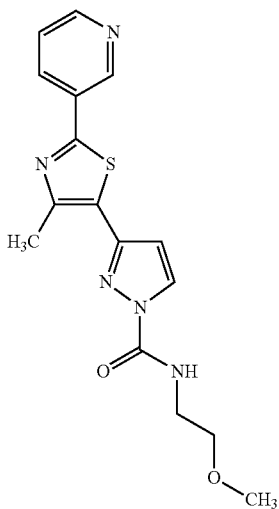 | |
| 127 | 2.57 | 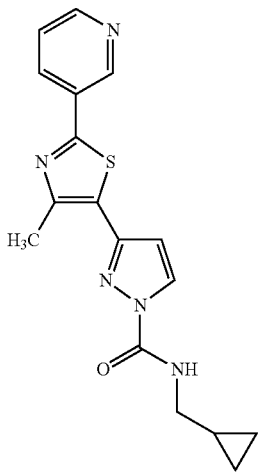 [SMILES: Cc1nc(-c2cccnc2)sc1-c1ccn(C(=O)NCC2CC2)n1] | |

| Ex. No. | logP [1] (HCOOH) | Formula | (M+) + 1 (LC/MS) |
|---|---|---|---|
| 128 | 2.38 | 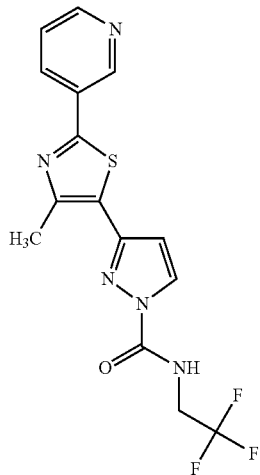 [SMILES: Cc1nc(-c2cccnc2)sc1-c1ccn(C(=O)NCC(F)(F)F)n1] | |
| 129 | 2.34 | 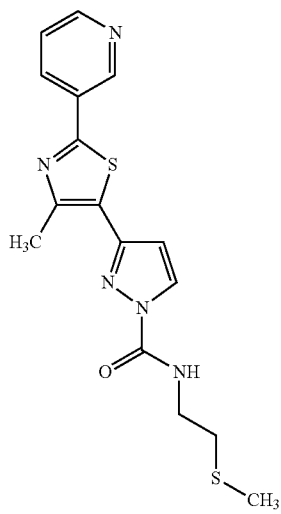 | |
| 130 | 4.17 | 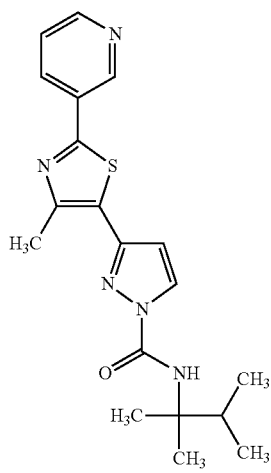 | |

| Ex. No. | logP [1) (HCOOH) | Formula | (M+) + 1 (LC/MS) |
|---|---|---|---|
| 131 | 2.14 | 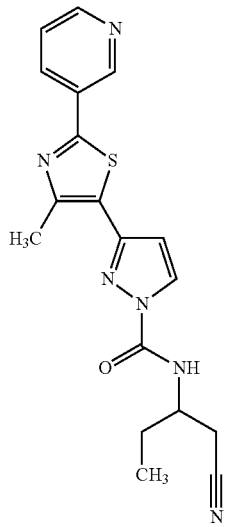 [SMILES: CCC(CC#N)NC(=O)n1ccc(-c2sc(-c3cccnc3)nc2C)n1] | |
| 132 | 2.46 | 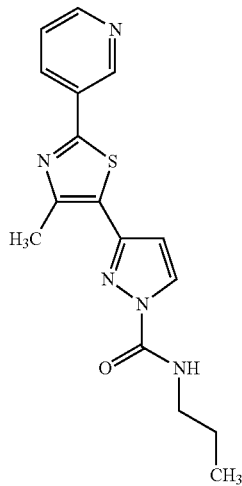 [SMILES: CCCNC(=O)n1ccc(-c2sc(-c3cccnc3)nc2C)n1] | |
| 133 | 2.53 | 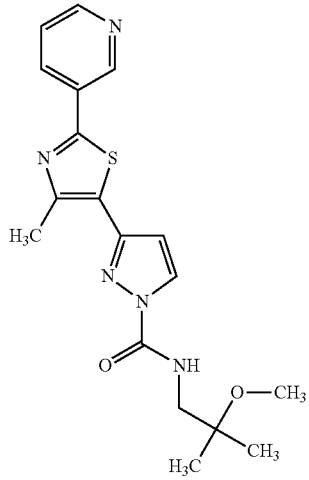 | |

-continued
| Ex. No. | logP [1] (HCOOH) | Formula | (M+) + 1 (LC/MS) |
|---|---|---|---|
| 134 | 2.69 | 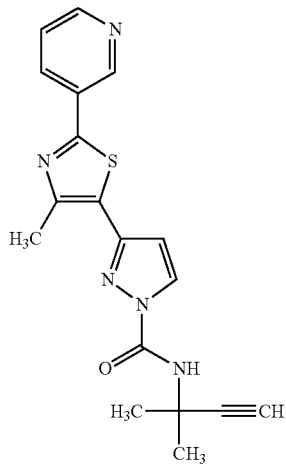 [SMILES: C#CC(C)(C)NC(=O)n1ccc(-c2sc(-c3cccnc3)nc2C)n1] | |
| 135 | 3.28 | 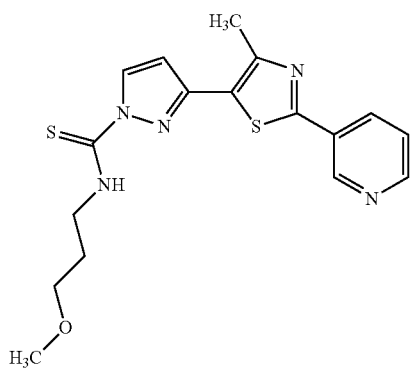 [SMILES: COCCCNC(=S)n1ccc(-c2sc(-c3cccnc3)nc2C)n1] | |
| 136 | 4.41 | 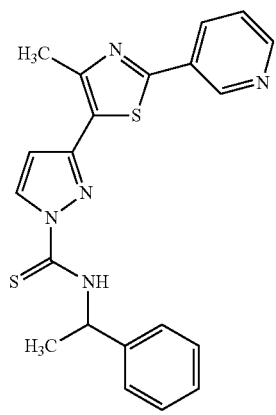 [SMILES: Cc1nc(-c2cccnc2)sc1-c1ccn(C(=S)NC(C)c2ccccc2)n1] | |
| 137 | 2.65 | 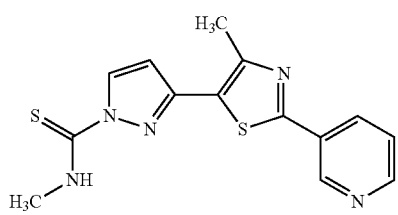 [SMILES: CNC(=S)n1ccc(-c2sc(-c3cccnc3)nc2C)n1] | |

-continued
| Ex. No. | logP [1]) (HCOOH) | Formula | (M+) + 1 (LC/MS) |
|---|---|---|---|
| 138 | 2.19 | 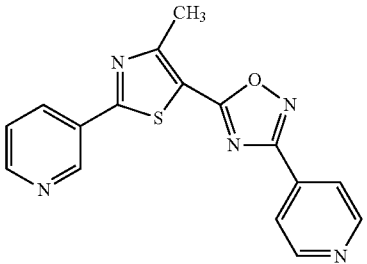 [SMILES: Cc1nc(-c2cccnc2)sc1-c1nc(-c2ccncc2)no1] | |
| 139 | 2.61 | 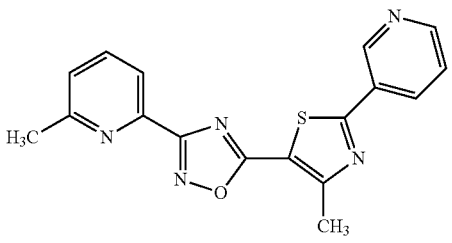 [SMILES: Cc1cccc(-c2noc(-c3sc(-c4cccnc4)nc3C)n2)n1] | |
| 140 | 3.31 | 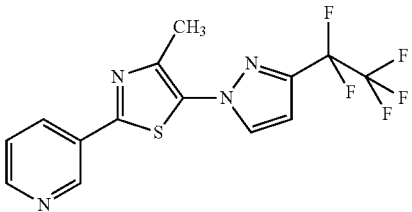 [SMILES: Cc1nc(-c2cccnc2)sc1-n1ccc(C(F)(F)C(F)(F)F)n1] | |
| 141 | 3.42 | 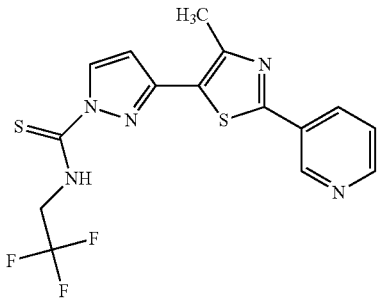 [SMILES: Cc1nc(-c2cccnc2)sc1-c1ccn(C(=S)NCC(F)(F)F)n1] | |
| 142 | 3.35 | 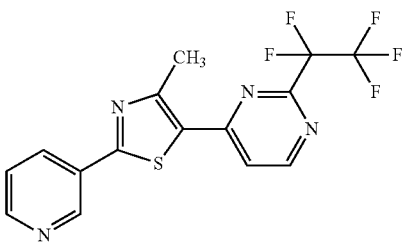 [SMILES: Cc1nc(-c2cccnc2)sc1-c1ccnc(C(F)(F)C(F)(F)F)n1] | |
| 143 | 4.28 | 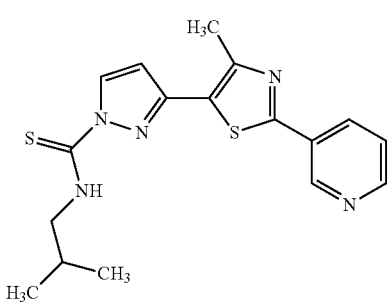 [SMILES: Cc1nc(-c2cccnc2)sc1-c1ccn(C(=S)NCC(C)C)n1] | |

-continued

| Ex. No. | logP [1] (HCOOH) | Formula | (M+) + 1 (LC/MS) |
|---|---|---|---|
| 144 | 2.72 | | |
| 145 | 1.71 | | |
| 146 | 1.43 | | |
| 147 | 1.24 | | |
| 148 | 1.59 | | 325.0 |
| 149 | 1.85 | | 307.1 |

| Ex. No. | logP [1] (HCOOH) | Formula | (M+) + 1 (LC/MS) |
|---|---|---|---|
| 150 | 1.76 | 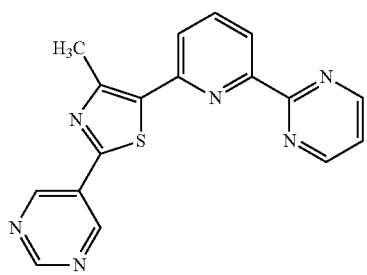 [SMILES: Cc1nc(-c2cncnc2)sc1-c1cccc(-c2ncccn2)n1] | 333.1 |
| 151 | 1.54 | 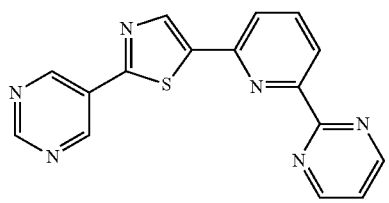 [SMILES: c1cnc(-c2cccc(-c3cnc(-c4cncnc4)s3)n2)nc1] | 319.1 |
| 152 | 2.43 | 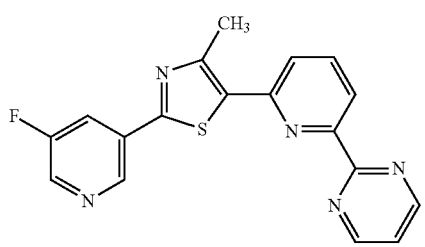 [SMILES: Cc1nc(-c2cncc(F)c2)sc1-c1cccc(-c2ncccn2)n1] | 350.1 |
| 153 | 2.11 | 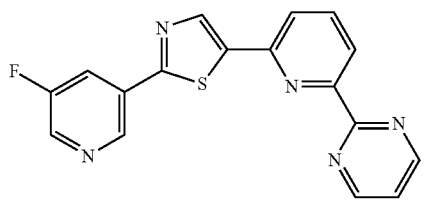 [SMILES: Fc1cncc(-c2ncc(-c3cccc(-c4ncccn4)n3)s2)c1] | 336.1 |
| 154 | 2.13 | 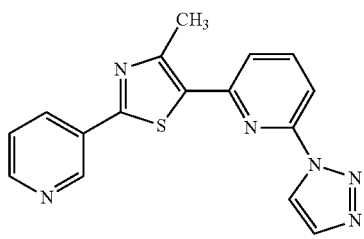 [SMILES: Cc1nc(-c2cccnc2)sc1-c1cccc(-n2ccnn2)n1] | |
| 155 | 1.89 | 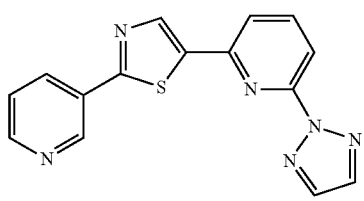 [SMILES: c1cncc(-c2ncc(-c3cccc(-n4nccn4)n3)s2)c1] | 307.1 |

-continued

| Ex. No. | logP [1] (HCOOH) | Formula | (M+) + 1 (LC/MS) |
|---|---|---|---|
| 156 | 2.65 | | |
| 157 | 2.35 | | 405.1 |
| 158 | 1.41 | | |
| 159 | 3.16 | | |
| 160 | 1.44 | | 308.1 |
| 161 | 1.13 | | |
| 162 | 0.84 | | |

-continued
| Ex. No. | logP [1] (HCOOH) | Formula | (M+) + 1 (LC/MS) |
|---|---|---|---|
| 163 | 1.07 | 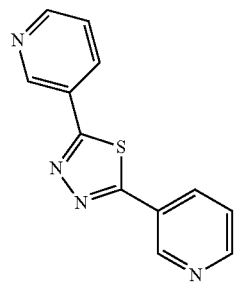 [SMILES: c1cncc(-c2nnc(-c3cccnc3)s2)c1] | |
| 164 | 1.39 | 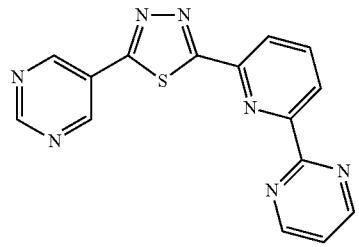 [SMILES: c1cnc(-c2cccc(-c3nnc(-c4cncnc4)s3)n2)nc1] | |
| 165 | 1.91 | 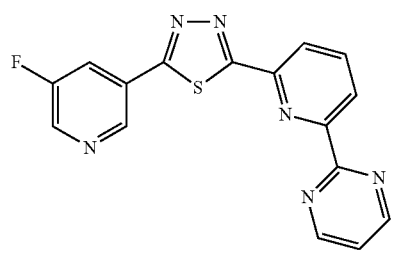 [SMILES: Fc1cncc(-c2nnc(-c3cccc(-c4ncccn4)n3)s2)c1] | 337.1 |
| 166 | 0.91 | 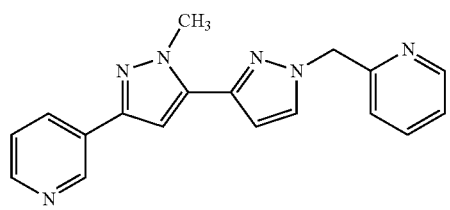 [SMILES: Cn1nc(-c2cccnc2)cc1-c1ccn(Cc2ccccn2)n1] | |
| 167 | 0.83 | 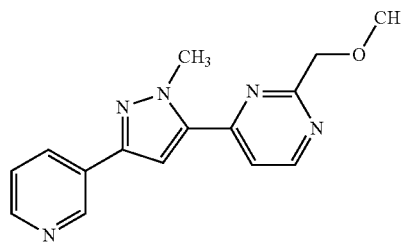 | |
| 168 | 0.95 | 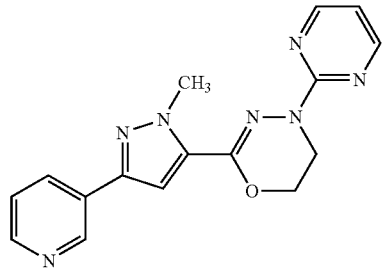 [SMILES: Cn1nc(-c2cccnc2)cc1C1=NN(c2ncccn2)CCO1] | |

| Ex. No. | logP [1) ](HCOOH) | Formula | (M+) + 1 (LC/MS) |
|---|---|---|---|
| 169 | 1.64 | | |
| 170 | 0.42 | | |
| 171 | 0.87 | | |
| 172 | 2.53 | | |
| 173 | 2.66 | | |
| 174 | 1.76 | | |

| Ex. No. | logP [1) (HCOOH) | Formula | (M+) + 1 (LC/MS) |
|---|---|---|---|
| 175 | 2.23 | 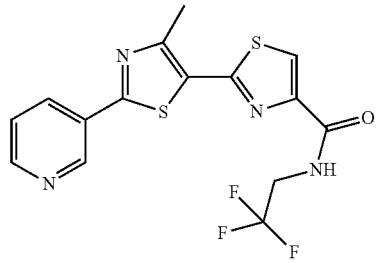 [SMILES: Cc1nc(-c2cccnc2)sc1-c1nc(C(=O)NCC(F)(F)F)cs1] | |
| 176 | 3.21 | 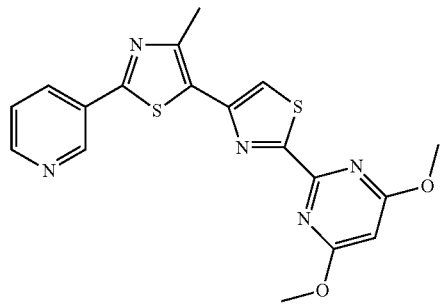 [SMILES: COc1cc(OC)nc(-c2nc(-c3sc(-c4cccnc4)nc3C)cs2)n1] | |
| 177 | 2.19 | 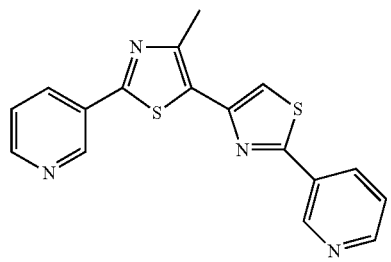 [SMILES: Cc1nc(-c2cccnc2)sc1-c1csc(-c2cccnc2)n1] | |
| 178 | 2.43 | 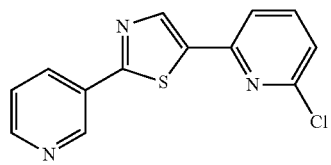 [SMILES: Clc1cccc(-c2cnc(-c3cccnc3)s2)n1] | |
| 179 | 1.06 | 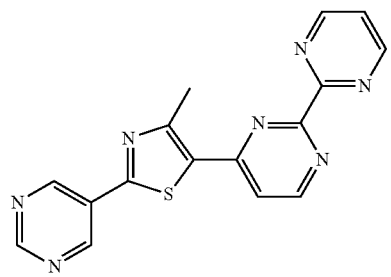 [SMILES: Cc1nc(-c2cncnc2)sc1-c1ccnc(-c2ncccn2)n1] | |
| 180 | 1.43 | 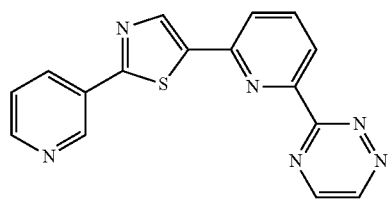 [SMILES: c1cncc(-c2ncc(-c3cccc(-c4nccnn4)n3)s2)c1] | |

-continued
| Ex. No. | logP [1] (HCOOH) | Formula | (M+) + 1 (LC/MS) |
|---|---|---|---|
| 181 | 1.82 | 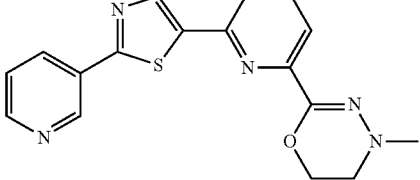 | 338.1 |
| 182 | 1.74 | 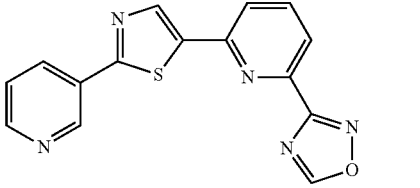 [SMILES: c1cncc(-c2ncc(-c3cccc(-c4ncon4)n3)s2)c1] | 308.1 |
| 183 | 1.24 | 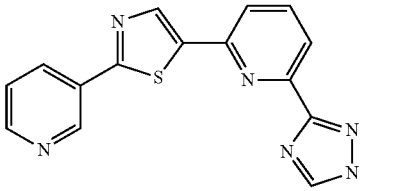 [SMILES: c1cncc(-c2ncc(-c3cccc(-c4nc[nH]n4)n3)s2)c1] | 307.1 |
| 184 | 1.44 | 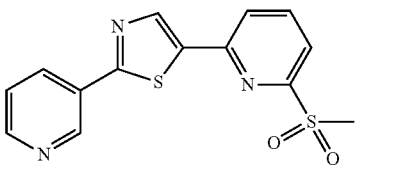 [SMILES: CS(=O)(=O)c1cccc(-c2cnc(-c3cccnc3)s2)n1] | 318.0 |
| 185 | 1.68 | 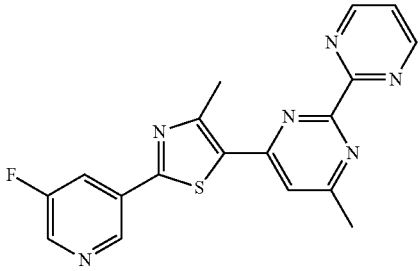 [SMILES: Cc1cc(-c2sc(-c3cncc(F)c3)nc2C)nc(-c2ncccn2)n1] | |
| 186 | 1.63 | 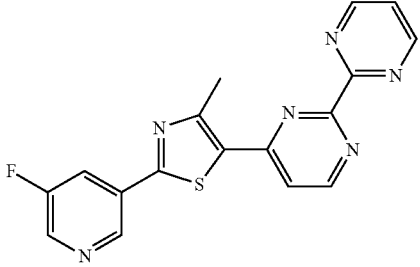 [SMILES: Cc1nc(-c2cncc(F)c2)sc1-c1ccnc(-c2ncccn2)n1] | 351.1 |
| 187 | 2.53 | 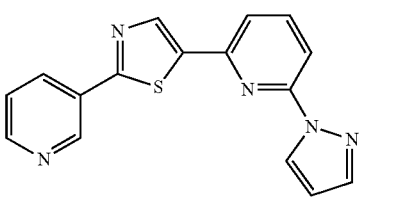 [SMILES: c1cncc(-c2ncc(-c3cccc(-n4cccn4)n3)s2)c1] | 306.1 |

| Ex. No. | logP [1] (HCOOH) | Formula | (M+) + 1 (LC/MS) |
|---|---|---|---|
| 188 | 3.08 | 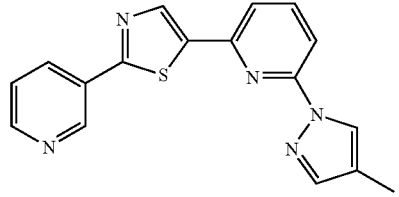 [SMILES: Cc1cnn(-c2cccc(-c3cnc(-c4cccnc4)s3)n2)c1] | |
| 189 | 2.85 | 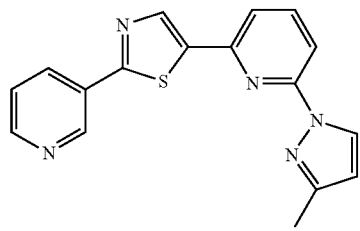 [SMILES: Cc1ccn(-c2cccc(-c3cnc(-c4cccnc4)s3)n2)n1] | |
| 190 | 1.67 | 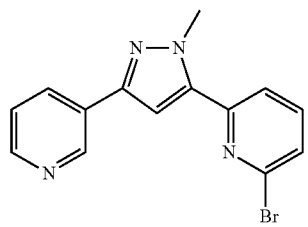 [SMILES: Cn1nc(-c2cccnc2)cc1-c1cccc(Br)n1] | |
| 191 | | | |
| 192 | 1.12 | 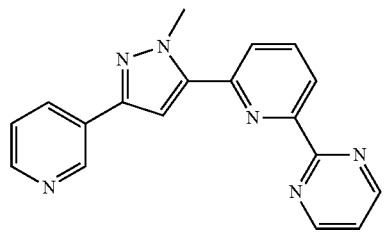 [SMILES: Cn1nc(-c2cccnc2)cc1-c1cccc(-c2ncccn2)n1] | |
| 193 | 1.41 | 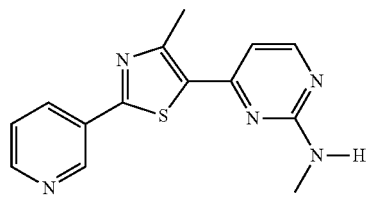 [SMILES: CNc1nccc(-c2sc(-c3cccnc3)nc2C)n1] | |
| 194 | 2.15 | 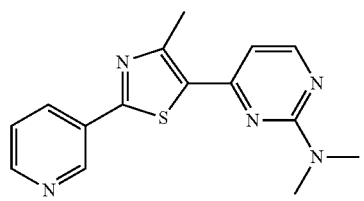 [SMILES: Cc1nc(-c2cccnc2)sc1-c1ccnc(N(C)C)n1] | |

-continued
| Ex. No. | logP [1] (HCOOH) | Formula | (M+) + 1 (LC/MS) |
|---|---|---|---|
| 195 | 3.76 | 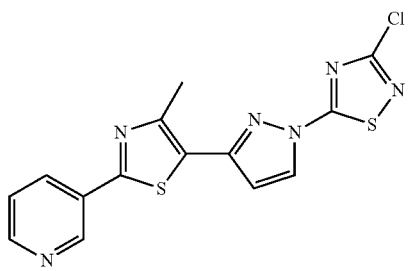 [SMILES: Cc1nc(-c2cccnc2)sc1-c1ccn(-c2nc(Cl)ns2)n1] | |
| 196 | 3.01 | 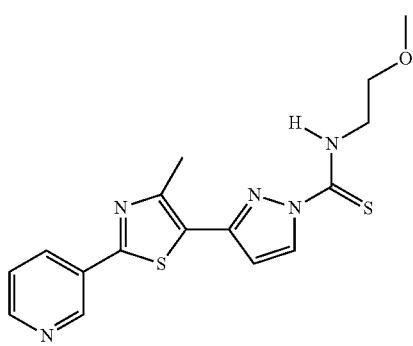 [SMILES: COCCNC(=S)n1ccc(-c2sc(-c3cccnc3)nc2C)n1] | |
| 197 | 2.58 | 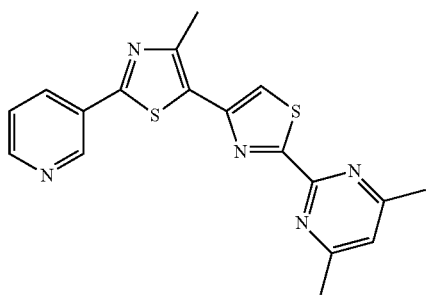 [SMILES: Cc1cc(C)nc(-c2nc(-c3sc(-c4cccnc4)nc3C)cs2)n1] | |
| 198 | | | |
| 199 | 0.93 | 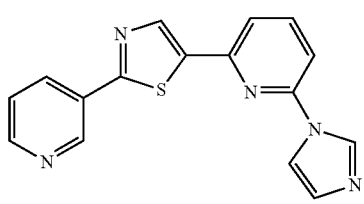 [SMILES: c1cncc(-c2ncc(-c3cccc(-n4ccnc4)n3)s2)c1] | |
| 200 | 2.83 | 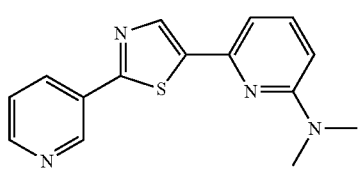 [SMILES: CN(C)c1cccc(-c2cnc(-c3cccnc3)s2)n1] | |
| 201 | 0.89 | 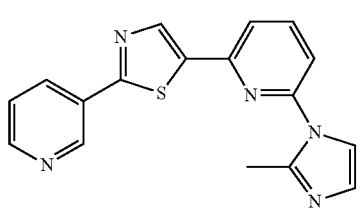 [SMILES: Cc1nccn1-c1cccc(-c2cnc(-c3cccnc3)s2)n1] | |

-continued
| Ex. No. | logP [1] (HCOOH) | Formula | (M+) + 1 (LC/MS) |
|---|---|---|---|
| 202 | 3.13 | 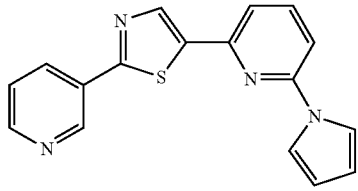 [SMILES: c1cncc(-c2ncc(-c3cccc(-n4cccc4)n3)s2)c1] | |
| 203 | 1.99 | 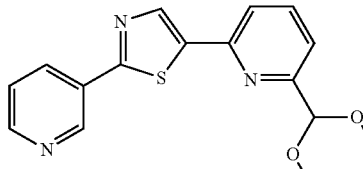 | 326.0 |
| 204 | 1.87 | 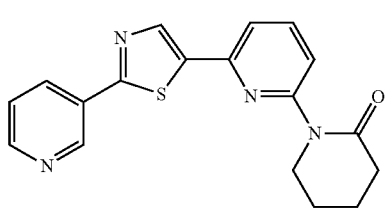 [SMILES: O=C1CCCCN1c1cccc(-c2cnc(-c3cccnc3)s2)n1] | |
| 205 | 1.82 | 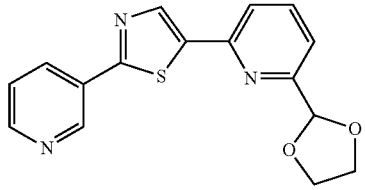 [SMILES: c1cncc(-c2ncc(-c3cccc(C4OCCO4)n3)s2)c1] | |
| 206 | 2.11 | 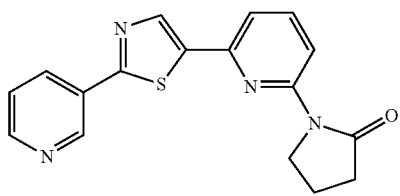 [SMILES: O=C1CCCN1c1cccc(-c2cnc(-c3cccnc3)s2)n1] | |
| 207 | | | |
| 208 | | | |
| 209 | | | |
| 210 | | | |
| 211 | | | |
| 212 | | | |
| 213 | | | |
| 214 | | | |
| 215 | | | |
| 216 | | | |
| 217 | 1.43 | 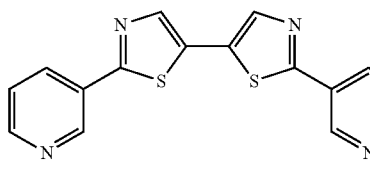 | |

| Ex. No. | logP [1] (HCOOH) | Formula | (M+) + 1 (LC/MS) |
|---|---|---|---|
| 218 | 0.89 | 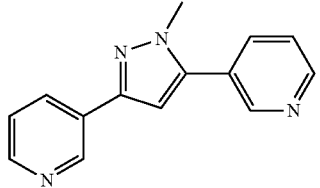 [SMILES: Cn1nc(-c2cccnc2)cc1-c1cccnc1] | |
| 219 | 0.92 | 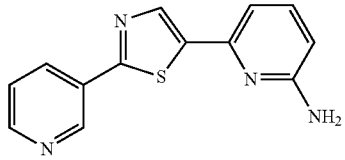 [SMILES: Nc1cccc(-c2cnc(-c3cccnc3)s2)n1] | |
| 220 | | | |
| 221 | 1.34 | 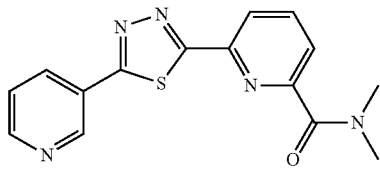 [SMILES: CN(C)C(=O)c1cccc(-c2nnc(-c3cccnc3)s2)n1] | |
| 222 | | | |
| 223 | 2.46 | 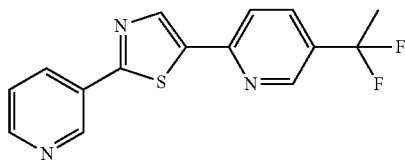 [SMILES: CC(F)(F)c1ccc(-c2cnc(-c3cccnc3)s2)nc1] | |
| 224 | 2.77 | 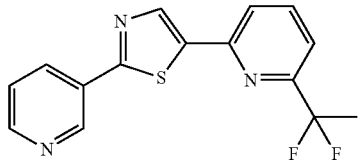 [SMILES: CC(F)(F)c1cccc(-c2cnc(-c3cccnc3)s2)n1] | |
| 225 | 2.08 | 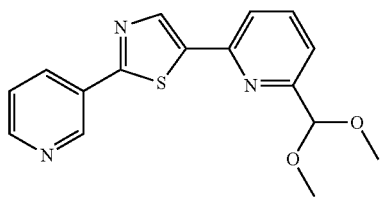 [SMILES: COC(OC)c1cccc(-c2cnc(-c3cccnc3)s2)n1] | 314.1 |
| 226 | 0.98 | 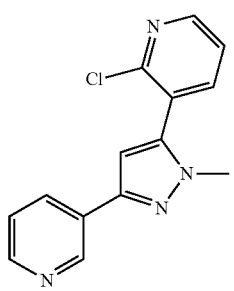 [SMILES: Cn1nc(-c2cccnc2)cc1-c1cccnc1Cl] | |

-continued

| Ex. No. | logP [1] (HCOOH) | Formula | (M+) + 1 (LC/MS) |
|---|---|---|---|
| 227 | 0.89 | | |
| 228 | 0.89 | | |
| 229 | 1.78 | | |
| 230 | | | |
| 231 | | | |
| 232 | | | |
| 233 | 2.69 | | |
| 234 | 2.93 | | |
| 235 | 2.38 | | |

-continued

| Ex. No. | logP [1] (HCOOH) | Formula | (M+) + 1 (LC/MS) |
| --- | --- | --- | --- |
| 236 | 2.38 | | |
| 237 | 2.05 | | |
| 238 | 2.53 | | |
| 239 | | | |
| 240 | | | |
| 241 | 2.07 | | |
| 242 | 1.61 | | |
| 243 | 1.67 | | |
| 244 | 1.77 | | |

-continued
| Ex. No. | logP [1] (HCOOH) | Formula | (M+) + 1 (LC/MS) |
|---|---|---|---|
| 245 | 1.46 | 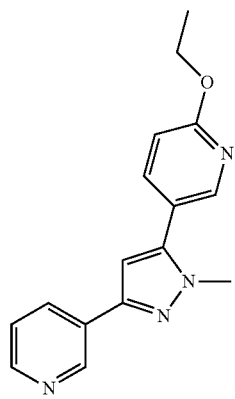 [SMILES: CCOc1ccc(-c2cc(-c3cccnc3)nn2C)cn1] | |
| 246 | 1.14 | 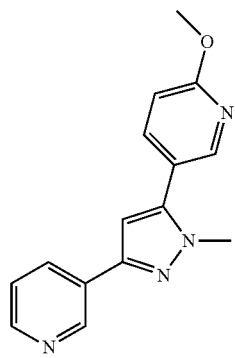 [SMILES: COc1ccc(-c2cc(-c3cccnc3)nn2C)cn1] | |
| 247 | 1.66 | 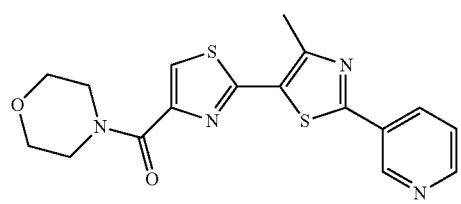 [SMILES: Cc1nc(-c2cccnc2)sc1-c1nc(C(=O)N2CCOCC2)cs1] | |
| 248 | 1.54 | 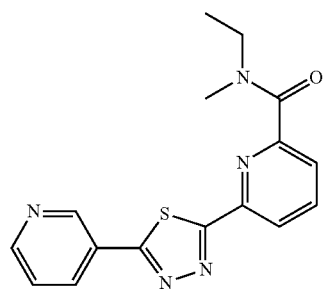 [SMILES: CCN(C)C(=O)c1cccc(-c2nnc(-c3cccnc3)s2)n1] | |
| 249 | 1.29 | 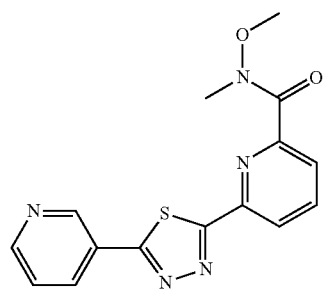 [SMILES: CON(C)C(=O)c1cccc(-c2nnc(-c3cccnc3)s2)n1] | |

| Ex. No. | logP [1] (HCOOH) | Formula | (M+) + 1 (LC/MS) |
|---|---|---|---|
| 250 | 1.29 | | |

1) Description of the method for determining the logP values (formic acid method)

The logP values given in the table were determined in accordance with EEC Directive 79/831 Annex V.A8 by HPLC (High Performance Liquid Chromatography) on a reversed-phase column (C18). Temperature: 55° C.

Mobile phases for the determination in the acidic range (pH 3.4):

Mobile phase A: Acetonitrile+1 ml of formic acid/litre.
Mobile phase B: water+0.9 ml of formic acid/litre.

Gradient: from 10% mobile phase A/90% mobile phase B to 95% mobile phase A/5% mobile phase B in 4.25 min.

Calibration was carried out using unbranched alkan-2-ones (having 3 to 16 carbon atoms) with known logP values (determination of the logP values by the retention times using linear interpolation between two successive alkanones). The lambda max values were determined in the maxima of the chromatographic signals using the UV spectra from 200 nm to 400 nm.

TABLE 2

| Ex. No. | NMR data (ppm) |
|---|---|
| 1 | $D_6$-DMSO: 2.75 (s, 3H), 7.55 (m, 1H), 7.65 (m, 1H), 7.95 (d, 1H), 8.75 (m, 1H), 8.7 (m, 1H), 9.15 (m, 3H), 9.2 (s, 1H) |
| 3 | $CD_3CN$: 2.5 (s, 3H), 7.15 (d, 1H), 7.3 (t, 1H), 7.45 (dd, 1H), 8 (d, 1H), 8.2 (d, 1H), 8.75 (m, 1H), 8.8 (d, 2H), 9.7 (s, 1H) |
| 5 | $D_6$-DMSO: 7.55 (m, 2H), 8.1 (m, 1H), 8.15 (m, 1H), 8.3 (m, 1H), 8.35 (m, 1H), 8.7 (m, 1H), 9.0 (d, 2H), 9.2 (s, 1H) |
| 6 | $CD_3CN$: 2.75 (s, 3H), 7.45 (m, 2H), 7.4 (m, 1H), 8.0 (m, 1H), 8.3 (m, 2H), 8.6 (m, 1H), 8.9 (m, 2H), 9.2 (m, 1H) |
| 7 | $D_6$-DMSO: 2.7 (s, 3H), 4.2 (t, 2H), 4.6 (t, 2H), 6.9 (t, 1H), 7.5 (dd, 1H), 8.3 (d, 1H), 8.55 (d, 2H), 8.65 (m, 1H), 9.1 (s, 1H) |
| 8 | $CD_3CN$: 2.75 (s, 3H), 4.2 (dd, 2H), 4.55 (dd, 2H), 7.45 (m, 1H), 7.8 (m, 2H), 7.9 (t, 1H), 8.3 (d, 1H), 8.65 (m, 1H), 9.2 (s, 1H) |
| 9 | $D_6$-DMSO: 7.65 (m, 1H), 7.7 (m, 1H), 8.45 (m, 1H), 8.55 (m, 1H), 8.8 (m, 1H), 9.1 (m, 2H), 9.3 (m, 2H) |
| 10 | $D_6$-DMSO: 7.6 (m, 2H), 8.25 (t, 1H), 8.45 (m, 2H), 8.55 (m, 1H), 8.75 (m, 1H), 9.05(d, 2H), 9.3 (s, 1H) |
| 21 | $CD_3CN$: 2.75 (s, 3H), 7.45 (m, 1H), 7.7 (d, 1H), 7.95 (d, 1H), 8.1 (m, 1H), 8.3 (m, 1H), 8.7 (m, 1H), 9.15 (s, 1H) |
| 22 | $D_6$-DMSO: 2.7 (s, 3H), 7 (s, 1H), 7.5 (t, 1H), 7.55 (m, 1H), 8.3 (d, 1H); 8.7 (m, 1H); 8.8 (s, 1H), 8.9 (m, 2H), 9.1 (s, 1H) |
| 49 | $D_6$-DMSO: 7.55 (m, 1H), 7.8 (d, 1H), 8.2 (m, 1H), 8.35 (m, 2H), 8.7 m, 2H), 9.2 (s, 1H) |
| 59 | $d_6$-DMSO: 2.90 (s, 3H), 4.00 (s, 6H), 7.55 (m, 1H), 7.89 (m, 1H), 8.35 (m, 1H), 8.70 (m, 1H), 9.04 (m, 1H), 9.18 (m, 1H) |
| 61 | $d_6$-DMSO: 2.80 (s, 3H), 3.45 (s, 3H), 4.60 (s, 2H), 7.55 (m, 1H), 7.72 (m, 1H), 8.35 (m, 1H), 8.70 (m, 1H), 8.84 (m, 1H), 9.15 (m, 1H) |
| 67 | $D_6$-DMSO: 4.2 (m, 2H), 4.6 (m, 2H), 6.9 (m, 1H), 7.5 (m, 1H), 8.15 (s, 1H), 8.3 (d, 1H), 8.55 (m, 2H), 8.7 (m, 1H), 9.15 (s, 1H) |
| 88 | $d_6$-DMSO: 7.58 (m, 1H), 7.68 (m, 1H), 8.30 (m, 1H), 8.45 (m, 1H), 8.72 (m, 1H), 9.05 (m, 4H), 9.25 (m, 1H) |

TABLE 2-continued

| Ex. No. | NMR data (ppm) |
|---|---|
| 89 | $d_6$-DMSO: 7.13 (m, 1H), 7.48 (m, 1H), 7.55 (m, 1H), 8.35 (m, 1H), 8.45 (m, 1H), 8.70 (m, 1H), 8.75 (m, 1H), 8.90 (m, 2H), 9.19 (m, 1H) |
| 97 | $d_6$-DMSO: 2.79 (s, 3H), 6.60 (m, 1H), 7.52 (m, 1H), 7.69 (m, 1H), 7.85 (m, 2H), 8.10 (m, 1H), 8.30 (m, 1H), 8.60 (m, 1H), 8.65 (m, 1H), 9.15 (m, 1H) |
| 148 | $D_6$-DMSO: 4.2 (m, 2H), 4.6 (m, 2H), 7.5 (m, 1H), 7.7 (d, 1H), 7.95 (t, 1H), 8.1 (d, 1H), 8.3 (m, 1H), 8.6 (s, 1H), 8.65 (m, 1H), 9.2 (s, 1H) |
| 149 | $D_6$-DMSO: 7.55 (m, 1H), 8.0-8.3 (m, 6H), 8.4 (m, 1H), 8.7 (m, 1H), 9.2 (s, 1H) |
| 150 | $d_6$-DMSO: 2.82 (s, 3H), 7.55 (m, 1H), 7.93 (m, 1H), 8.12 (m, 1H), 8.32 (m, 1H), 9.01 (m, 2H), 9.28 (m, 1H), 9.32 (m, 2H) |
| 151 | $d_6$-DMSO: 7.55 (m, 1H), 8.10 (m, 1H), 8.20 (m, 1H), 8.33 (m, 1H), 8.78 (m, 1H), 9.00 (m, 2H), 9.29 (m, 1H), 9.38 (m, 2H) |
| 152 | $d_6$-DMSO: 2.80 (s, 3H), 7.55 (m, 1H), 7.90 (m, 1H), 8.12 (m, 1H), 8.20 (m, 1H), 8.32 (m, 1H), 8.65 (m, 1H), 9.05 (m, 3H) |
| 153 | $d_6$-DMSO: 7.58 (m, 1H), 8.10-8.30 (m, 4H), 8.70 (m, 2H), 9.00 (m, 2H), 9.10 (m, 1H), 9.00 (m, 1H) |
| 155 | $d_6$-DMSO: 7.55 (m, 1H), 7.95 (m, 1H), 8.2 (m, 4H), 8.4 (m, 1H), 8.7 (m, 2H), 9.2 (s, 1H) |
| 157 | $d_6$-DMSO: 3.40 (s, 3H), 7.55 (m, 1H), 7.88 (m, 1H), 8.05 (m, 1H), 8.10 (m, 1H), 8.38 (m, 1H), 8.68 (m, 2H), 9.20 (m, 1H) |
| 160 | $D_6$-DMSO: 7.25 (d, 1H), 7.55 (t, 1H), 7.65 (dd, 1H), 8.45 (d, 1H), 8.75 (d, 1H), 8.85 (d, 1H), 8.95 (m, 2H), 9.2 (s, 1H) |
| 165 | $d_6$-DMSO: 7.60 (m, 1H), 8.27 (m, 1H), 8.42 (m, 1H), 8.47 (m, 1H), 8.56 (m, 1H), 8.78 (m, 1H), 9.05 (m, 2H), 9.17 (m, 1H) |
| 181 | $D_6$-DMSO: 3.15 (m, 2H), 3.55 (s, 3H), 4.5 (m, 2H), 7.55 (m, 1H), 7.7 (d, 1H), 7.85 (m, 1H), 8 (m, 1H), 8.35 (m, 1H), 8.6 (s, 1H), 8.7 (m, 1H), 9.2 (s, 1H) |
| 182 | $D_6$-DMSO: 7.55 (m, 1H), 8.05 (m, 1H), 8.15 (m, 1H), 8.25 (d, 1H), 8.4 (m, 1H), 8.7 (m, 2H), 9.2 (s, 1H), 9.7 (s, 1H) |
| 183 | $D_6$-DMSO: 7.55 (m, 1H), 8-8.1 (m, 4H), 8.35 (m, 1H), 8.7 (m, 2H), 9.2 (s, 1H) |
| 184 | $d_6$-DMSO: 3.35 (s, 3H), 7.55 (m, 1H), 7.98 (m, 1H), 8.25-8.40 (m, 3H), 8.70 (m, 1H), 8.75 (m, 1H), 9.20 (m, 1H) |
| 186 | $d_6$-DMSO: 2.88 (s, 3H), 7.62 (m, 1H), 7.97 (m, 1H), 8.27 (m, 1H), 8.70 (m, 1H), 9.05 (m, 4H) |
| 187 | $d_6$-DMSO: 6.60 (m, 1H), 7.55 (m, 1H), 7.85-7.95 (m, 3H), 8.10 (m, 1H), 8.35 (m, 1H), 8.70 (m, 3H), 9.20 (m, 1H) |
| 203 | $d_6$-DMSO: 2.05 (m, 2H), 4.00 (m, 2H), 4.20 (m, 2H), 5.52 (s, 1H), 7.50 (m, 2H), 7.99 (m, 2H), 8.33 (m, 1H), 8.60 (m, 1H), 8.70 (m, 1H), 9.20 (m, 1H) |
| 225 | $d_6$-DMSO: 3.40 (s, 6H), 5.30 (s, 1H), 7.45 (m, 1H), 7.55 (m, 1H), 7.9-8.0 (m, 2H), 8.38 (m, 1H), 8.60 (m, 1H), 8.68 (m, 1H), 9.20 (m, 1H) |

BIOLOGICAL EXAMPLES

Example No. 1

Myzus Test (Spray Treatment)
Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of leaves of Chinese cabbage (*Brassica pekinensis*) which are heavily infested by all stages of the green peach aphid (*Myzus persicae*) are sprayed with an active compound preparation of the desired concentration.

After the desired period of time, the effect in % is determined. 100% means that all aphids have been killed; 0% means that none of the aphids have been killed.

In this test, for example, the following compounds of the Preparation Examples show an activity of ≥80% at an application rate of 500 g/ha:

Ex. Nos. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 141, 142, 143, 144, 145, 146, 147, 148, 149, 150, 151, 152, 153, 154, 155, 156, 157. 158, 159, 160, 161, 162, 163, 164, 165, 166, 167, 168, 169, 170, 171.

In this test, for example, the following compounds of the Preparation Examples show an activity of ≥80% at an application rate of 100 g/ha:
Ex. No. 140

Example No. 2

*Meloidogyne* Test (Spray Treatment)
Solvent: 80 Parts by Weight of Acetone

To produce a suitable preparation of active compound, 1 part by weight of active compound is mixed with the stated amount of solvent and the concentrate is diluted with water to the desired concentration.

Containers are filled with sand, solution of active compound, *Meloidogyne incognita* egg/larvae suspension and lettuce seeds. The lettuce seeds germinate and plants develop. On the roots, galls are formed.

After the desired period of time, the nematicide action in % is determined using the formation of galls as a measure. 100% means that no galls have been found; 0% means that the number of galls on the treated plants corresponds to that of the untreated control.

In this test, for example, the following compounds of the Preparation Examples show, at an application rate of 20 ppm, an activity of ≥80%.
Ex. Nos. 5, 57, 58, 61, 104, 135

Example No. 3

*Tetranychus* Test, OP-Resistant (Spray Treatment)
Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of the leaves of beans (*Phaseolus vulgaris*) which are infested by all stages of the greenhouse red spidermite (*Tetranychus urticae*) are sprayed with an active compound preparation of the desired concentration.

After the desired period of time, the effect in % is determined. 100% means that all spidermites have been killed; 0% means that none of the spidermites have been killed.

In this test, for example, the following compounds of the Preparation Examples show an activity of ≥80% at an application rate of 100 g/ha:
Ex. No. 27

Example No. 4

*Boophilus microplus* Test (Injection)
Solvent: Dimethyl sulphoxide

To produce a suitable preparation of active compound, 1 part by weight of active compound is mixed with the stated amounts of solvent, and the concentrate is diluted with water to the desired concentration.

The solution of active compound is injected into the abdomen (*Boophilus microplus*), and the animals are transferred into dishes and stored in a climatized room. The activity is checked by examination for deposition of fertile eggs, After the desired period of time, the effect in % is determined. 100% means that none of the ticks has laid fertile eggs.

In this test, for example, the following compounds of the Preparation Examples show, at an application rate of 20 µg/animal, an activity of ≥80%:
Ex. No. 49

The invention claimed is:
1. A compound of formula (IB-1)

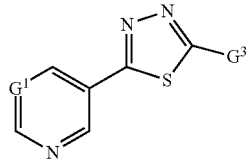

(IB-1)

in which
$G^1$ represents C-halogen and
$G^3$ represents optionally pyrimidinyl-substituted pyridyl or a salt, metal oxide or N-oxide thereof.
2. A compound of formula (IB-2)

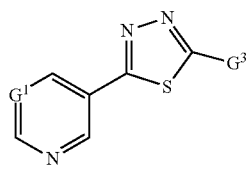

(IB-2)

in which
$G^1$ represents C—H and
$G^3$ represents in each case optionally pyrrolyl- or pyrimidinyl-substituted pyrazolyl, pyridyl or pyrimidinyl, or $C_1$-$C_4$-haloalkoxy-substituted phenyl;
or a salt, metal oxide or N-oxide thereof.

3. A composition comprising at least one compound according to claim 1 and one or more extenders, surfactants, or combinations thereof.

4. A composition comprising at least one compound according to claim 2 and one or more extenders, surfactants, or combinations thereof.

5. The compound of claim 1, wherein $G^1$ is C—F.

6. The compound of claim 2, wherein $G_3$ is phenyl substituted by $CF_3O$—.

* * * * *